United States Patent
Oliner et al.

(10) Patent No.: US 12,313,624 B2
(45) Date of Patent: May 27, 2025

(54) EX VIVO SYSTEMS AND METHODS FOR DETERMINING THE EFFECT OF A DRUG OR OTHER AGENT ON A TISSUE

(71) Applicant: Elephas Biosciences Corporation, Madison, WI (US)

(72) Inventors: Jonathan Daniel Oliner, Garrett Park, MD (US); Neil Anthony, Decatur, GA (US); Sean Caenepeel, Thousand Oaks, CA (US); Laura Catherine Funk Hrycyniak, Middleton, WI (US); John Rafter, Madison, WI (US); Tomasz Zal, Madison, WI (US)

(73) Assignee: Elephas Biosciences Corporation, Madison, WI (US)

( * ) Notice: Subject to any disclaimer, the term of this patent is extended or adjusted under 35 U.S.C. 154(b) by 406 days.

(21) Appl. No.: 17/834,263

(22) Filed: Jun. 7, 2022

(65) Prior Publication Data
US 2022/0326220 A1    Oct. 13, 2022

Related U.S. Application Data

(63) Continuation of application No. 17/566,154, filed on Dec. 30, 2021, now Pat. No. 11,366,101.
(Continued)

(51) Int. Cl.
*G06K 9/00* (2022.01)
*G01N 1/28* (2006.01)
(Continued)

(52) U.S. Cl.
CPC ......... *G01N 33/5011* (2013.01); *G01N 1/286* (2013.01); *G01N 1/42* (2013.01);
(Continued)

(58) Field of Classification Search
CPC . G06T 2207/30096; G06T 2207/30064; G06T 2207/20081; G06T 2207/20084;
(Continued)

(56) References Cited

U.S. PATENT DOCUMENTS

| 5,474,909 A | 12/1995 | Connors |
| 5,726,009 A | 3/1998 | Connors |

(Continued)

FOREIGN PATENT DOCUMENTS

| WO | 95/01455 | 1/1995 |
| WO | 2018/185760 | 10/2018 |

OTHER PUBLICATIONS

Holton AB, Sinatra FL, Kreahling J, Conway AJ, Landis DA, Altiok S. Microfluidic Biopsy Trapping Device for the Real-Time Monitoring of Tumor Microenvironment. PLoS One. Jan. 13, 2017;12(1):e0169797. doi: 10.1371/journal.pone.0169797. PMID: 28085924; PMCID: PMC5235371. (Year: 2017).*

(Continued)

*Primary Examiner* — Atiba O Fitzpatrick
(74) *Attorney, Agent, or Firm* — CASIMIR JONES, S.C.; Rikki A. Hullinger

(57) ABSTRACT

Provided are ex vivo systems and methods of predicting the response of a drug or other agent on a tissue. In some embodiments, the systems and methods comprise cutting a tissue into tissue fragments, adding a drug or other agent to the tissue fragments based on an estimated tumor content, and performing an ex vivo measurement on the tissue fragments.

16 Claims, 37 Drawing Sheets

Related U.S. Application Data

(60) Provisional application No. 63/236,282, filed on Aug. 24, 2021, provisional application No. 63/132,725, filed on Dec. 31, 2020.

(51) Int. Cl.
  *G01N 1/42* (2006.01)
  *G01N 33/50* (2006.01)
  *G01N 33/58* (2006.01)
  *G06T 7/00* (2017.01)

(52) U.S. Cl.
  CPC ....... *G01N 33/5014* (2013.01); *G01N 33/582* (2013.01); *G06T 7/0016* (2013.01); *G01N 2001/2873* (2013.01); *G06T 2207/10004* (2013.01); *G06T 2207/10024* (2013.01); *G06T 2207/10064* (2013.01); *G06T 2207/30024* (2013.01); *G06T 2207/30096* (2013.01)

(58) Field of Classification Search
  CPC .............. G06T 9/002; G06T 5/60; G01N 33/574–57496; G01N 2800/7028; G01N 2800/52; G01N 1/286; G01N 2001/2866; G01N 2001/2873; G01N 2001/288; G01N 2001/2886; G01N 33/4833; G01N 2015/1028; G01N 33/5008–5088; G01N 2500/00–20; G01N 29/4481; C12N 5/0693; C12N 5/0694; C12N 2502/30; A61P 35/00; A61P 35/02; A61P 35/04; G16H 20/10; C12Q 2600/136; A61B 5/4848; G06K 9/6256; G06K 9/6257; G06K 9/6259; G06V 10/70; G06V 10/82; G06V 10/774–7796; G06V 10/454; G06N 3/02–126; G06N 20/00–20; G06F 18/214–2155; G06F 7/023; G06F 40/16

See application file for complete search history.

(56) References Cited

U.S. PATENT DOCUMENTS

| | | | |
|---|---|---|---|
| 6,657,713 | B2 | 12/2003 | Hansen |
| 8,871,159 | B1 | 10/2014 | Apfel |
| 10,338,077 | B2 | 7/2019 | Iha et al. |
| 10,445,880 | B2 | 10/2019 | Boppart et al. |
| 10,564,100 | B1 | 2/2020 | Moroz et al. |
| 10,697,967 | B2 | 6/2020 | Liu et al. |
| 10,996,215 | B2 | 5/2021 | Trotter et al. |
| 11,254,913 | B1 | 2/2022 | Wardell |
| 2002/0142288 | A1 | 10/2002 | Kaultkiewicz et al. |
| 2005/0233309 | A1 | 10/2005 | Hankins |
| 2008/0008999 | A1* | 1/2008 | Hankins .................. G01N 1/31 435/7.1 |
| 2013/0149724 | A1* | 6/2013 | Chander ................ C12M 23/58 435/7.92 |
| 2016/0025701 | A1* | 1/2016 | Pratx .................. G01N 33/5044 435/35 |
| 2016/0102365 | A1 | 4/2016 | Ince |
| 2016/0274085 | A1 | 9/2016 | Nair |
| 2018/0209961 | A1 | 7/2018 | Schafer et al. |
| 2019/0011434 | A1* | 1/2019 | Hoffman ............ G01N 35/0099 |
| 2019/0024033 | A1* | 1/2019 | Chander ................ C12M 41/46 |
| 2019/0212325 | A1* | 7/2019 | Ballesteros Nobell ...................... C12N 5/0694 |
| 2019/0384047 | A1 | 12/2019 | Johnson |
| 2020/0224171 | A1 | 7/2020 | Straussman et al. |
| 2021/0208131 | A1* | 7/2021 | Kretzschmar ........ G06V 20/698 |
| 2023/0178239 | A1* | 6/2023 | Hause, Jr. .............. A61K 35/17 702/19 |

OTHER PUBLICATIONS

Zehir et al. Mutational Landscape of Metastatic Cancer Revealed from Prospective Clinical Sequencing of 10,000 Patients, Nat Med. Jun. 2017; 23(6): 703-713.

International Search Report & Written Opinion, International Patent Application No. PCT/US2021/065696, mailed Mar. 24, 2022, 9 pages.

EP Search Report, EP Patent Application No. 21916501.6, dated Oct. 21, 2024, 14 pages.

Martin Steve Z. et al. "Ex vivo tissue slice culture system to measure drug-response rates of hepatic metastatic colorectal cancer" BMC Cancer, vol. 19, No. 1, Dec. 1, 2019, 14 pages.

Zhang Wenhao et al. "Ex vivo treatment of prostate tumor tissue recapitulates in vivo therapy response" The Prostate, vol. 79, No. 4, Dec. 5, 2018, pp. 390-402.

Ashley L Beckwith et al. "Microfluidic Model for Evaluation of Immune Checkpoint Inhibitors in Human Tumors" Advanced Healthcare Materials, vol. 8, No. 11, May 6, 2019, 6 pages.

Cao Ruofan et al. "Multiphoton FLIM imaging of NAD (P) H and FAD with one excitation wavelength" Journal of Biomedical Optics, vol. 25, No. 01, Jan. 9, 2020, 17 pages.

\* cited by examiner

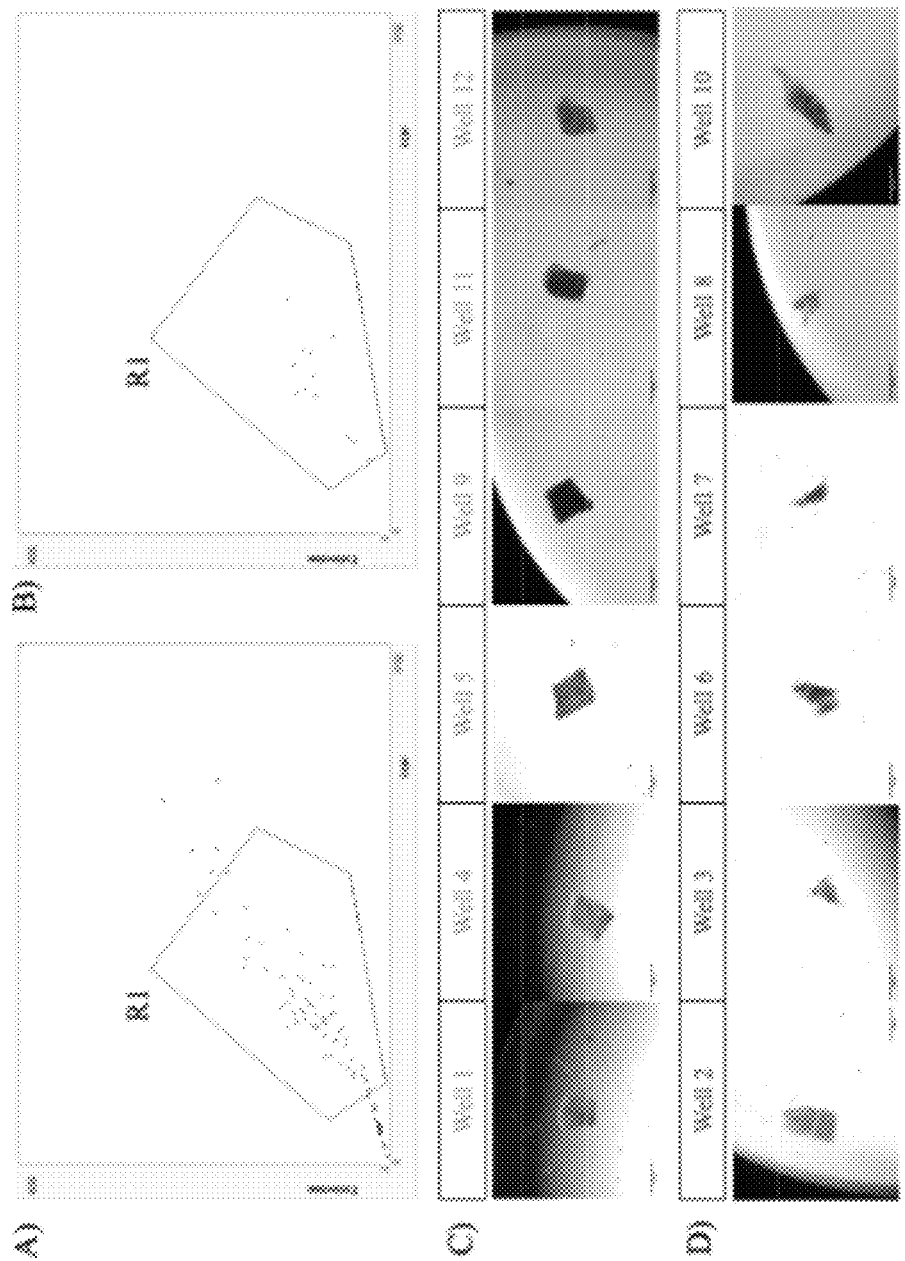
FIG. 7A-D

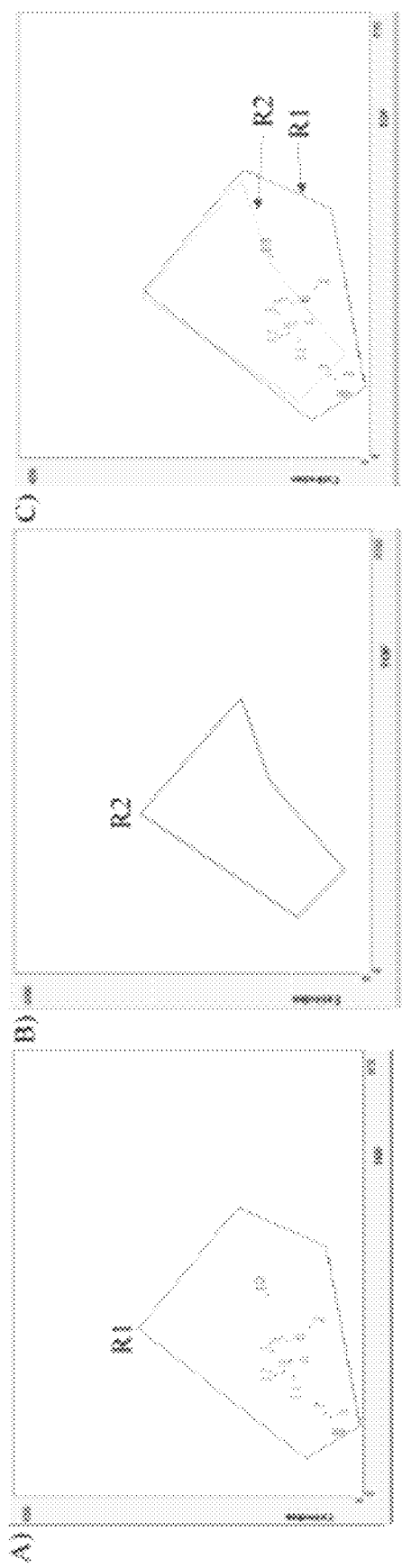
FIG. 8A-C

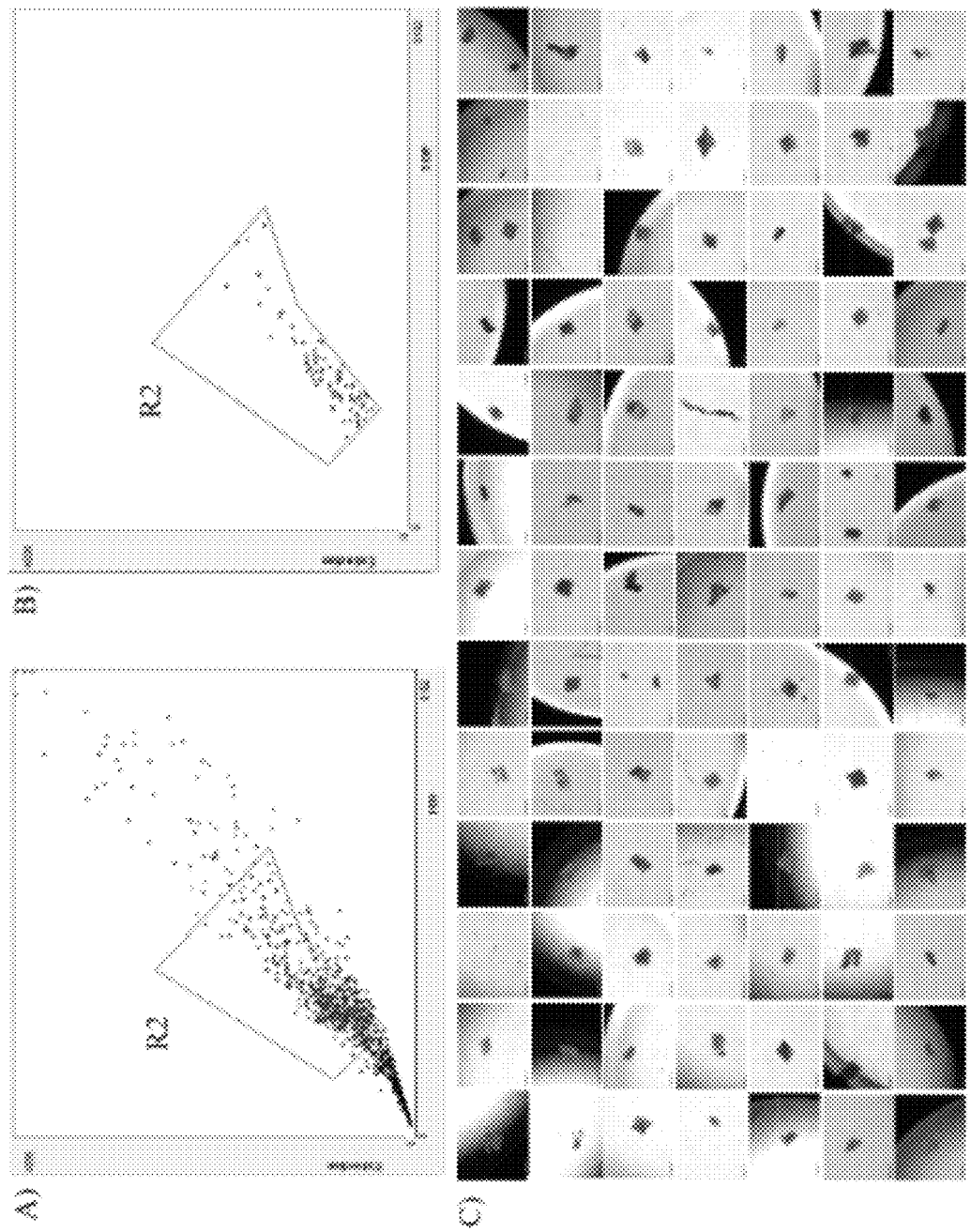
FIG. 9A-C

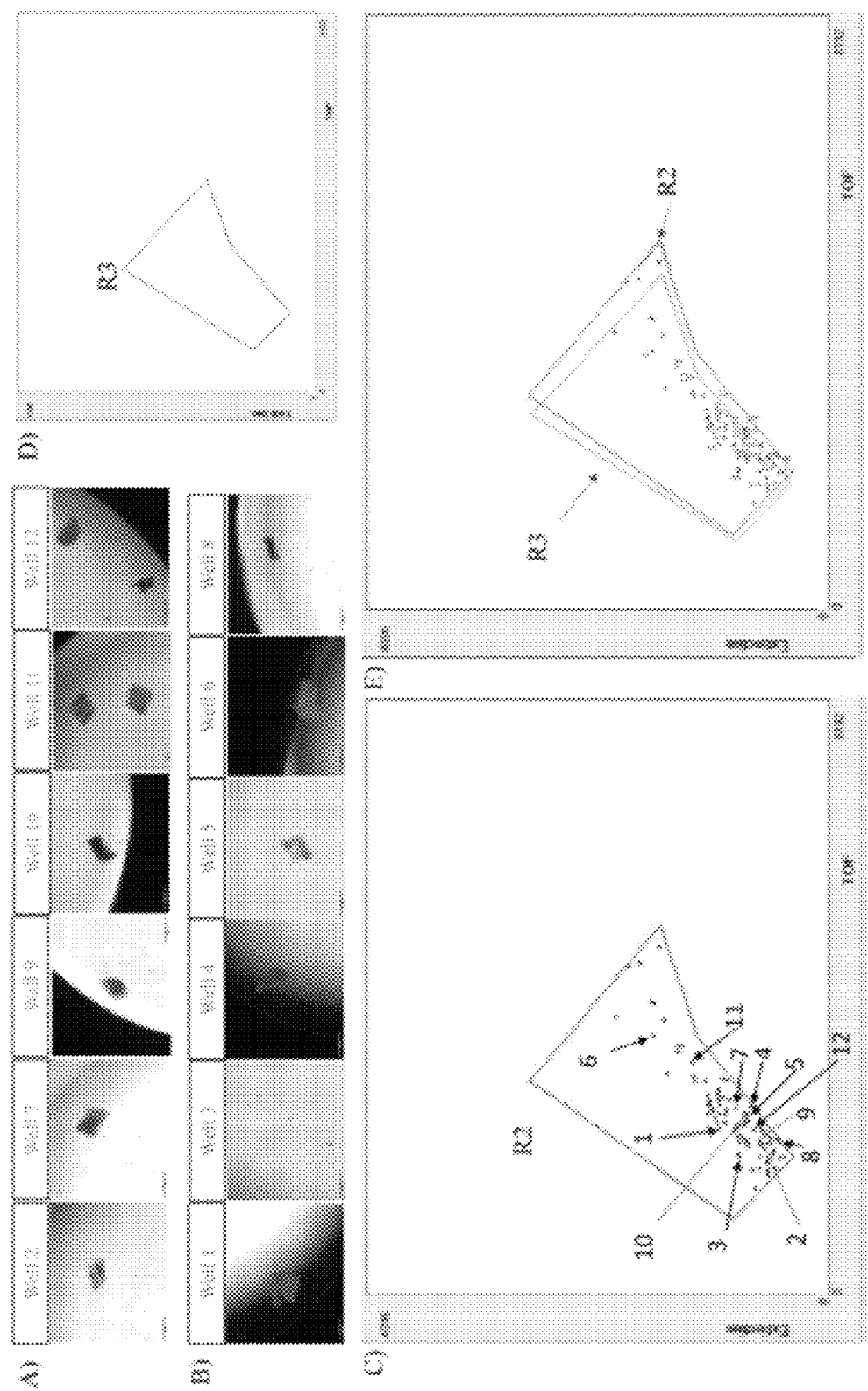
FIG. 10A-E

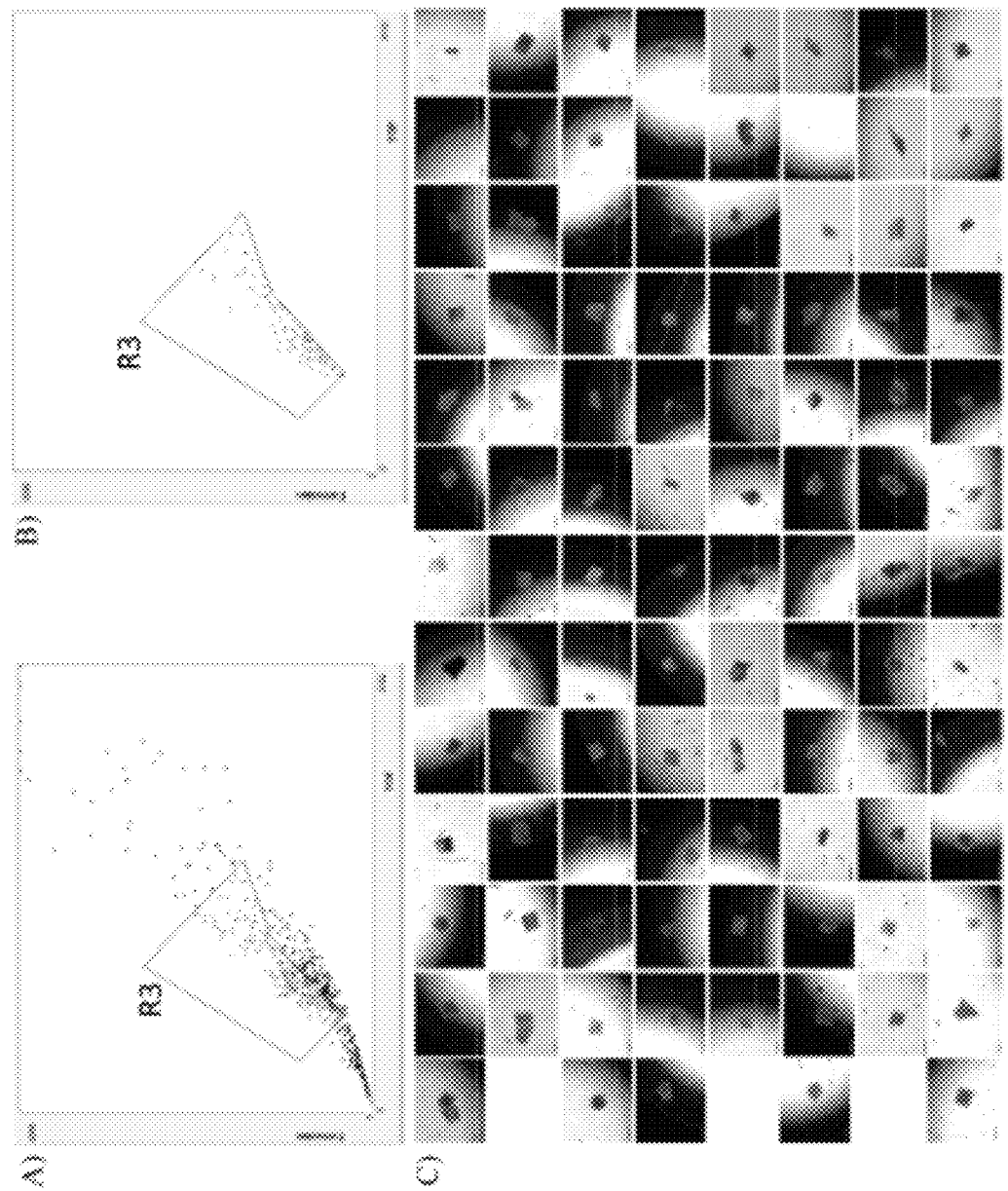
FIG. 11A-C

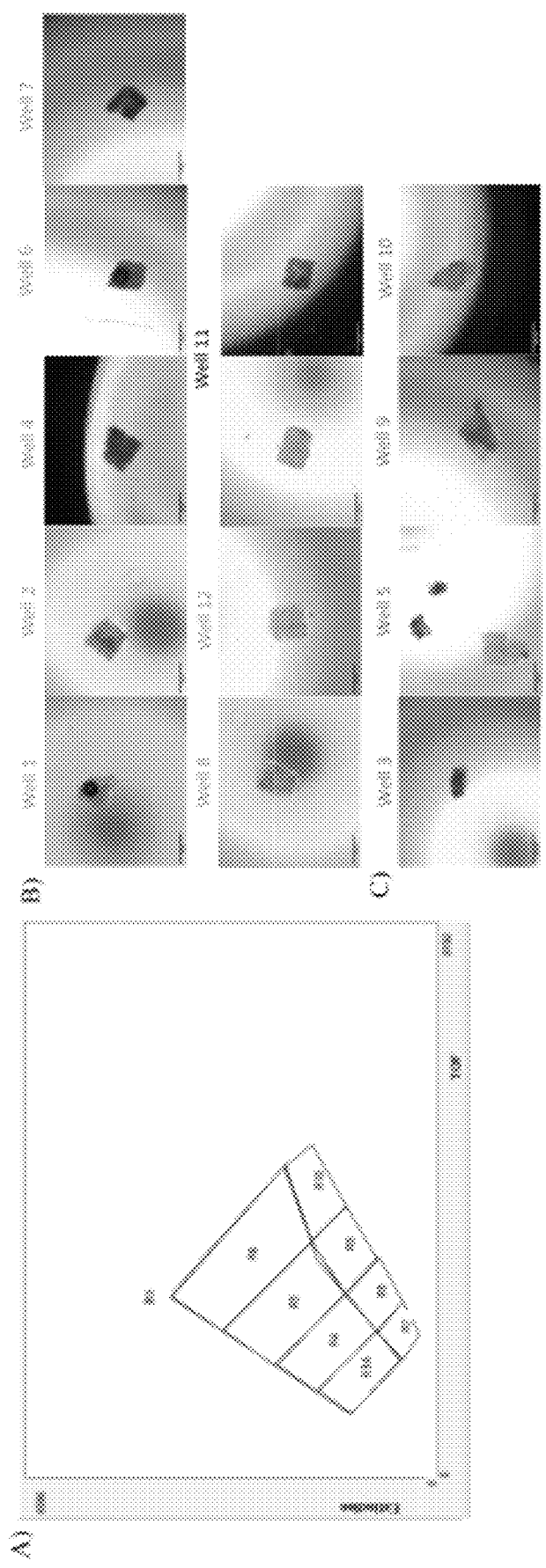
FIG. 12A-C

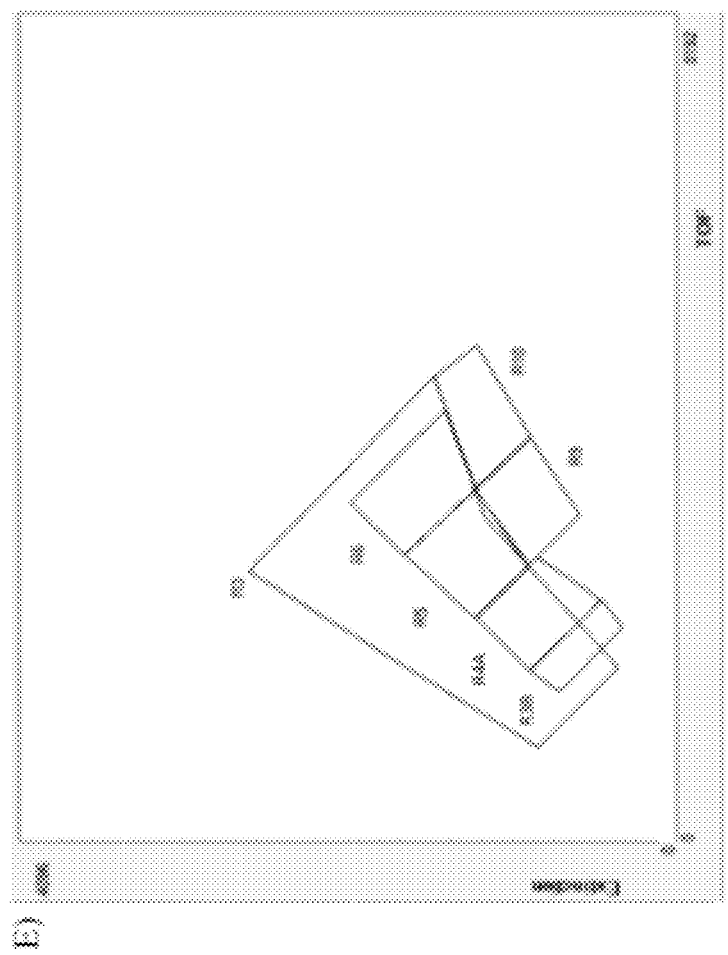
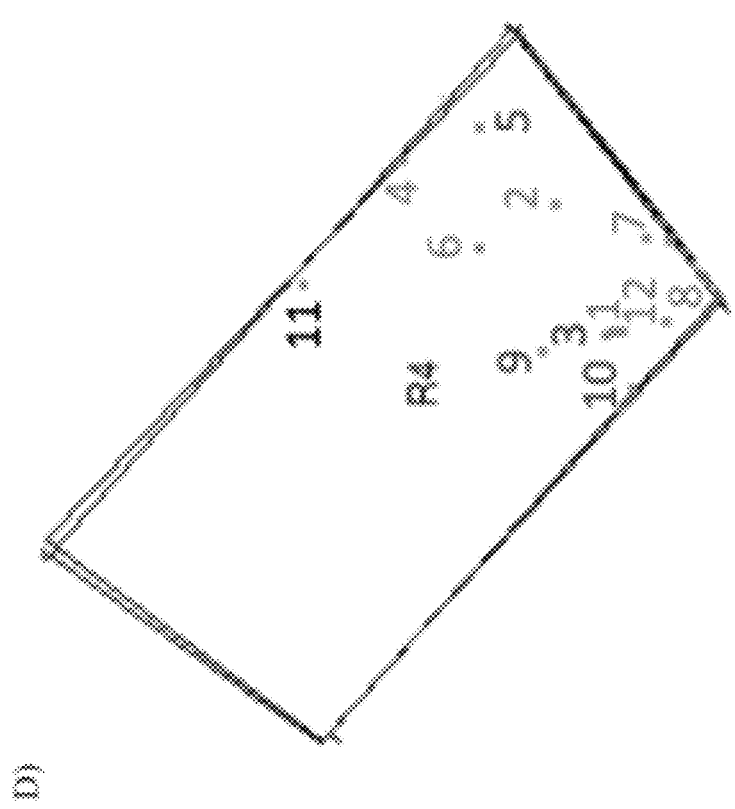
FIG. 12D-E

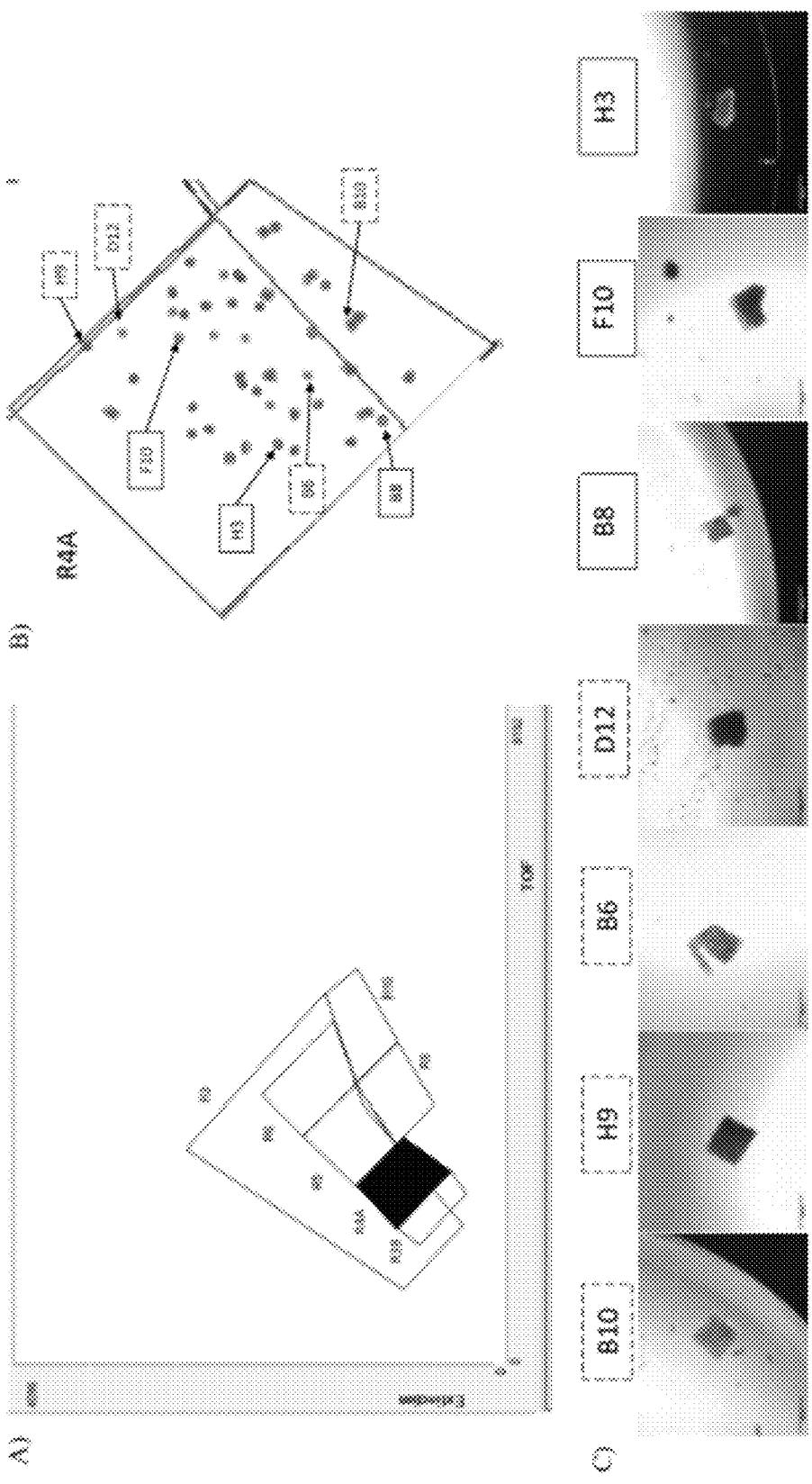
FIG. 13A-C

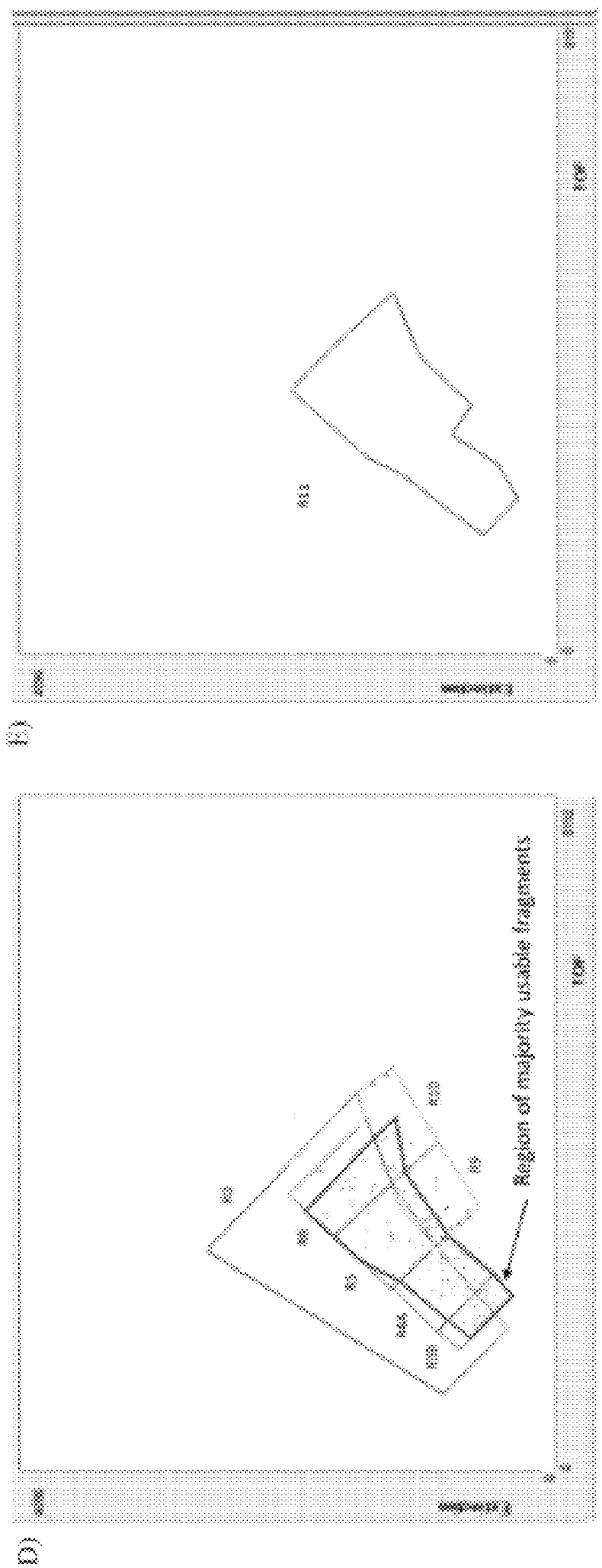
FIG. 13D-E

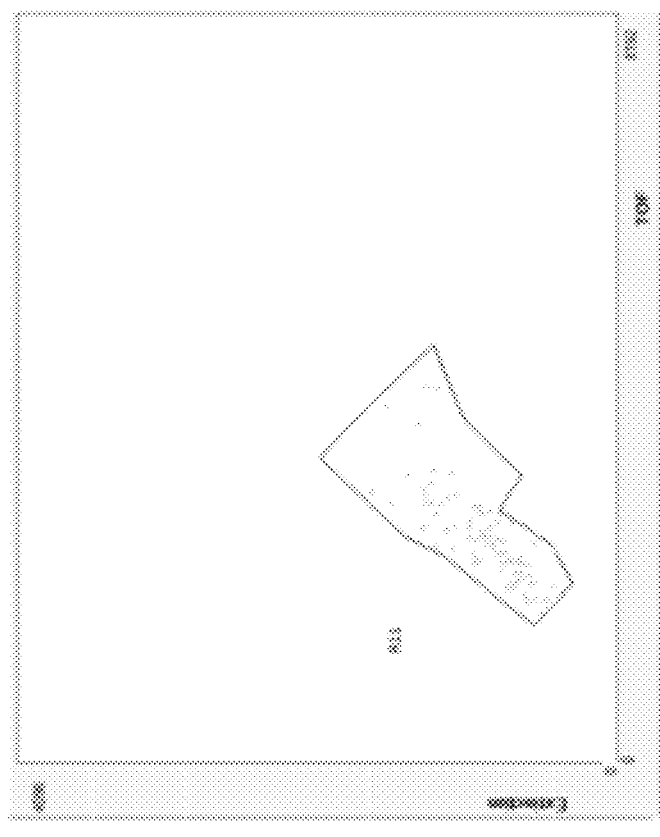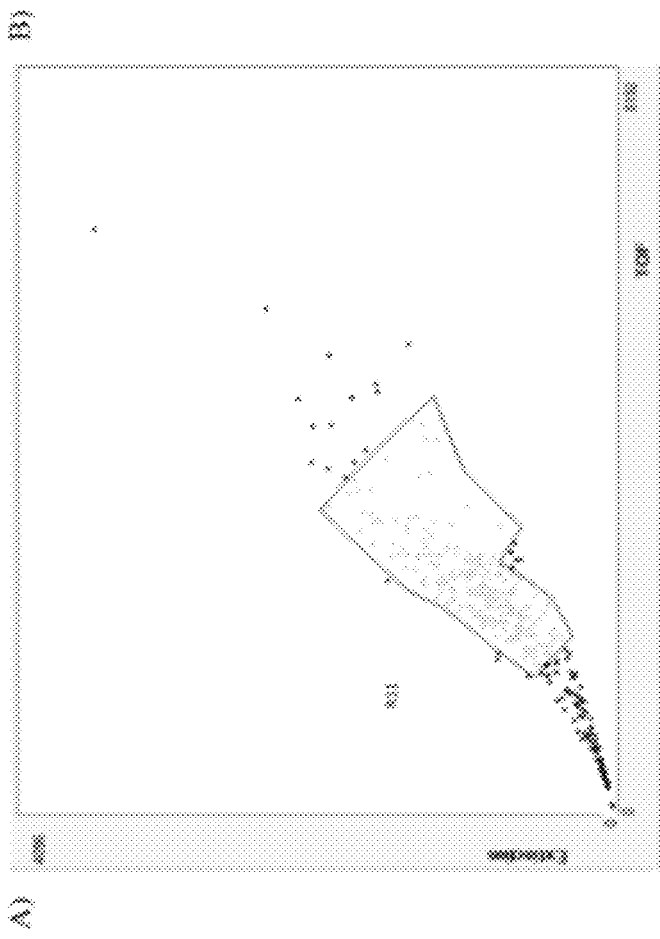
FIG. 14A-B

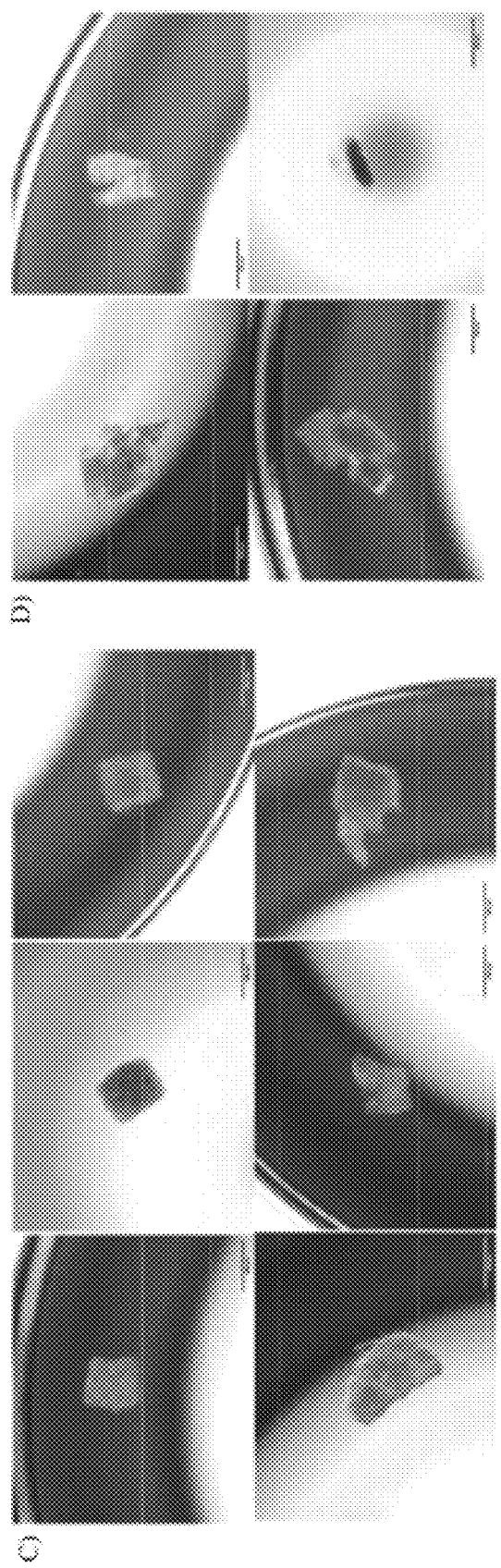
FIG. 14C-D

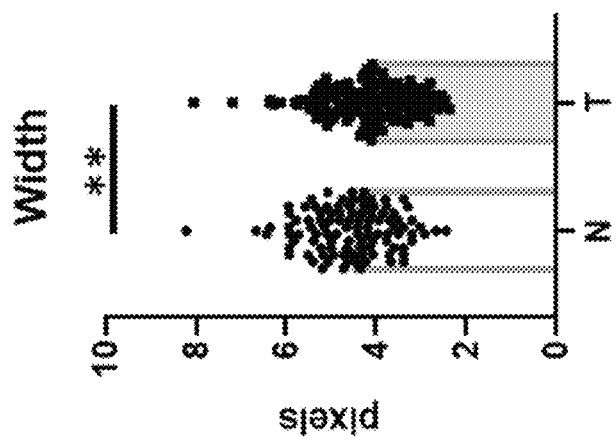
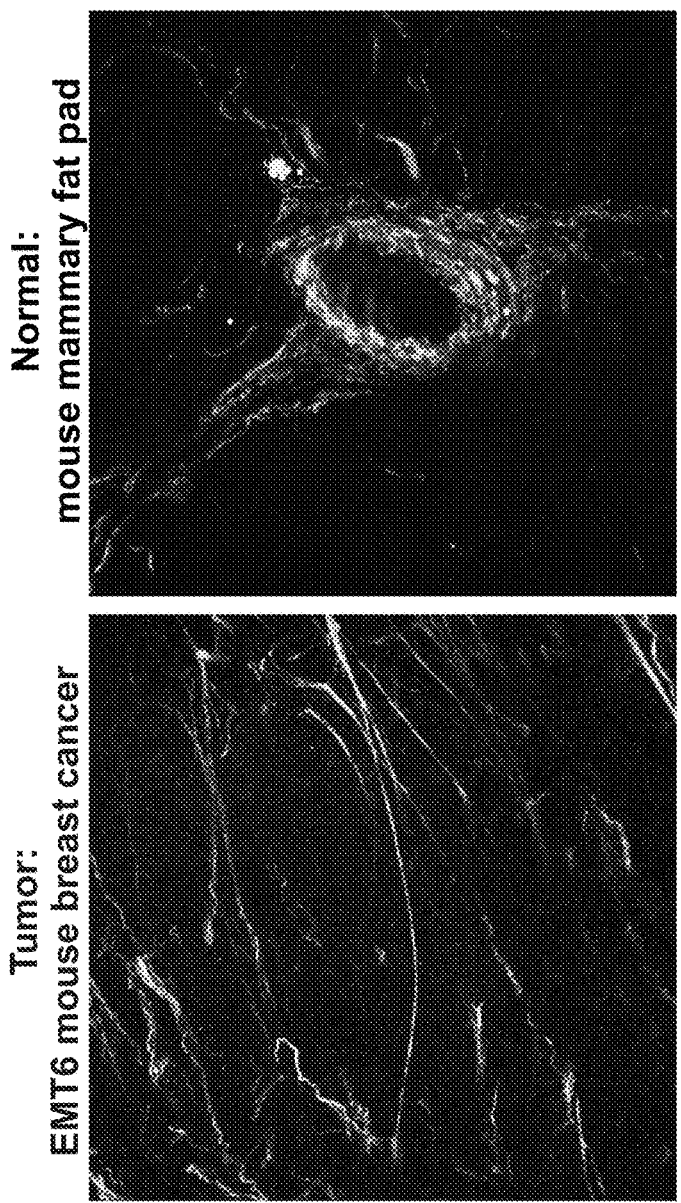
FIG. 17D
FIG. 17E

EX VIVO SYSTEMS AND METHODS FOR DETERMINING THE EFFECT OF A DRUG OR OTHER AGENT ON A TISSUE

The present application is a continuation of U.S. patent application Ser. No. 17/566,154, filed Dec. 30, 2021, which claims priority to U.S. Provisional Patent Application Ser. Nos. 63/132,725, filed Dec. 31, 2020 and 63/236,282, filed Aug. 24, 2021, the entire discloses of which are hereby incorporated by reference in their entireties.

FIELD

Provided herein are systems and methods for ex vivo determination of the effect of drugs or other agents on a tissue. In particular, provided herein are systems and methods for assessing the effects of drugs or other agents for treating cancer by assessing tissue ex vivo.

BACKGROUND

Predicting drug response in cancer patients remains a formidable challenge for the vast majority of oncology therapeutics. Given the considerable financial cost and significant adverse side-effects incurred with many therapies, progress on this front would provide meaningful benefit to patients. Although predictive biomarkers are available for several approved cancer therapeutics, only a small fraction of patients harbor tumors with these actionable biomarkers. Furthermore, of those individuals who receive biomarker guided therapies, only a subset will derive clinical benefit from treatment (Zehir et al. Nat Med. 2017 June; 23(6): 703). Technologies exist to perform chemosensitivity tests on a patient's tumor ex vivo in order to assess the efficacies of drug or drug combinations on the tumor. However, each such technology has its own drawbacks, which has greatly restricted their clinical utility or commercial success. Conventional studies based on two-dimensional (2D) cell monolayer models are limited in that the three-dimensional tissue architecture is lost. Further, in 2D monolayer models, tumor cells are expanded significantly in culture before initiating drug treatment, which can result in clonal selection/expansion. Three-dimensional culture systems based on spheroid or organoid model are closer mimics of the tumor in its native milieu but even such systems do not completely retain the stromal architecture. Tumor tissue fragments are the closest ex vivo replica of native tumor, but its applicability has been severely limited by the difficulties in establishing reliable and consistent culture.

BRIEF DESCRIPTION

Some embodiments relate to an ex vivo method of determining the effect of a drug or an agent on a tissue, the method comprising: cutting a tissue into tissue fragments; sorting the tissue fragments based on a characteristic (e.g., an optical characteristic) of the tissue fragments and dispensing a controlled number of tissue fragments into the chambers of a culture platform after sorting; imaging the tissue fragments which are dispensed into the chambers of the culture platform to estimate one or more of tumor content or cell viability of the tissue fragments; adding a drug or an agent to the tissue fragments and determining the effect of the drug or the agent on the tissue fragments based on data from one or more ex vivo measurements performed on the tissue fragments. In some embodiments, the drug or the agent is added to the tissue fragments based on one or more of the estimated tumor content or cell viability. In some embodiments, the data from the one or more ex vivo measurements is analysed based on one or more of the estimated tumor content or cell viability.

Some embodiments relate to a method of predicting the clinical responsiveness of a subject to a drug or an agent, the method comprising: a) providing tissue fragments, wherein the tissue fragments are generated from a tissue which is obtained from a subject; b) imaging the tissue fragments to estimate one or more of tumor content or cell viability of the tissue fragments; c) adding a drug or an agent to the tissue fragments; d) performing one or more ex vivo measurements on the tissue fragments that are treated with the drug or the agent; and e) predicting the clinical responsiveness of the subject to the drug or the agent based on data obtained from the one or more ex vivo measurements performed on the tissue fragments. In some embodiments, the drug or the agent is added to the tissue fragments based on one or more of the estimated tumor content or cell viability. In some embodiments, the data from the one or more ex vivo measurements is analysed based on one or more of the estimated tumor content or cell viability.

Some embodiments relate to a method of treatment of a subject, the method comprising: receiving a predicted clinical responsiveness of a subject to a drug or an agent and treating the subject based on the predicted clinical responsiveness, wherein the steps to generate a predicted clinical responsiveness of a subject to a drug or an agent comprises: a) generating tissue fragments from a tissue obtained from the subject; b) sorting the tissue fragments based on an optical characteristic of the tissue fragments; b) treating the sorted tissue fragments ex-vivo with a drug or an agent based on one or more of an estimated tumor content or an estimated cell viability of the tissue or the tissue fragments; b) obtaining an ex vivo tissue parameter data from an ex vivo tissue parameter measurement performed on the tissue fragments treated with the drug or the agent; and c) generating a predicted clinical responsiveness of the subject to the drug or the agent based on the ex vivo tissue parameter data.

Some embodiments relate to a system comprising one or more or all of: a tissue cutting system configured to cut a tissue into tissue fragments; a sorter configured to sort the tissue fragments based on a characteristic (e.g., optical characteristic) of the tissue fragments and dispense the tissue fragments into regions (e.g., chambers) of a culture platform; an imaging system configured to image the tissue fragments; and an incubator configured to house the culture platform.

DESCRIPTION OF THE FIGURES

FIG. 7A-D shows arbitrary initial gate setting for sorting. A) sorting gate; B) fragments dispensed from gate R1. For A) and B), each dot represents a fragment; C) dispensed fragment with sharp edge(s) and the desired 300 μm size in one of the two dimensions; D) distorted or undesirable fragments. Image scale bar=300 μm.

FIG. 8A-C shows gate optimization R1 to R2. A) Locations of fragments dispensed in FIG. 7B inside gate R1; B) gate R2 was made by excluding undesirable fragments from gate R1; C) comparison between gates R1 and R2. For A) and C), each dot represents a fragment FIG. 9A-C shows fragments sorted using gate R2. A) sorting profile; B) locations of fragments dispensed inside gate R2; C) Images of dispensed fragment from gate R2. Image scale bar=300 μm. For A) and B), each dot represents a fragment. The FIG. 9A shows the tissue fragments falling inside the gate R2 and those falling outside the gate.

FIG. 10A-E shows gate optimization of R2 to R3. A) Representative images of fragments dispensed from gate R2 with sharp edge(s) and 300 μm size in one of the two dimensions; B) Distorted or undesired fragments dispensed from gate R2; C) Locations of representative fragments with sharp edges and ~300 μm size in at least one of the two dimensions (2, 7, 9, 10, 11, 12) shown in FIG. 10A and the undesired fragments (1, 3, 4, 5, 6, 8) shown in FIG. 10B, inside gate R2. D) Gate R3 was made by excluding majority of the undesired fragments from gate R2. E) Comparison between gate R2 and R3.

FIG. 11A-C shows fragments sorted using gate R3. A) sorting profile; B) Locations of fragments dispensed inside gate R3; C) Images of dispensed fragment from gate R3. Image scale bar=300 μm. For A) and B), each dot represents a tissue fragment.

FIG. 12A-E shows gate R3 optimization through subdivision. A) shows gate R3 compartmentalized into gates R3A, R4 to R8; B) Images of useable dispensed fragments using gate R4; C) Images of undesirable dispensed fragments using gate R4; D) sorting profile using gate R4. E) Modified compartmentalized gates. For B) and C), fragment locations were marked in D). Image scale bar=300 μm.

FIG. 13A-E shows modified compartmentalized gate R3. A) Layout of modified compartmentalized COPAS gate R3; B) sorting profile using refined gate R4A (marked in black in FIG. 13A); C) Images of dispensed fragments (useable fragments (broken box) and undesirable fragments (solid box)) using refined gate R4A; D) Region where majority of useable fragments are located; E) Refined gate R11.

FIG. 14A-D shows fragments sorted using gate R11. A) Sorting profile; B) Locations of fragments dispensed inside gate R11. Representative images of dispensed fragments from gate R11 that are useable (C) and undesirable (D) for downstream experiments. Image scale bar=300 μm.

FIG. 17A-E show intrinsic, tissue fluorescence imaging used to distinguish tumor from normal tissue. FIG. 17A shows images of tumor tissue and normal tissue by fluorescence imaging of NAD(P)H using multi-photon fluorescent lifetime imaging microscopy (MP-FLIM). The figure shows the intrinsic contrast arising from the amplitude of NAD (P)H short lifetime component (a1). FIG. 17B shows the mean lifetime (tm) and short lifetime component (a1) in tumor and normal tissue respectively. Also shown are the values of mean tm (tm mean) and mean a1 (a1 mean) in tumor and normal tissue respectively. FIG. 17C shows the image entropy of NAD(P)H intensity quantified utilizing entropy parameters (median entropy and entropy skewness) in tumor and normal tissue respectively. FIG. 17D shows second harmonic generation (SHG) images of tumor and normal tissue respectively. FIG. 17E shows quantification of width for a second harmonic generation structure, indicating the differences in normal (N) versus tumor (T).

FIG. 18A shows NAD(P)H fluorescence (live cells) in a tissue fragment; FIG. 18B shows propidium iodide (PI) fluorescence (dead cells) as ground truth, in the same tissue fragment; FIG. 18C shows artificial intelligence (AI) based segmentation of the images in FIGS. 18A and 18B, where the cell and the cell nuclei shapes were segmented based on the combined fluorescence signals. FIG. 18D shows determination of PI-trained NAD (P)H intensity threshold for viability assessment of cells within tissue fragments.

FIG. 19A shows reduced viability when tissue fragments were cultured in conditions of hyperoxia and FIG. 19B shows increased number of live cells and reduced number of dead cell when tissue fragments were cultured in conditions of hypoxia (5% oxygen) compared to those cultured in ambient oxygen concentration.

FIG. 21A shows ATP luminescence as a measure of cell viability, FIG. 21B shows the number of live and dead cells, and FIG. 21C shows the percentage of dead cells, at Day 0 and at Day 3 respectively.

DETAILED DESCRIPTION

Figure 1A:
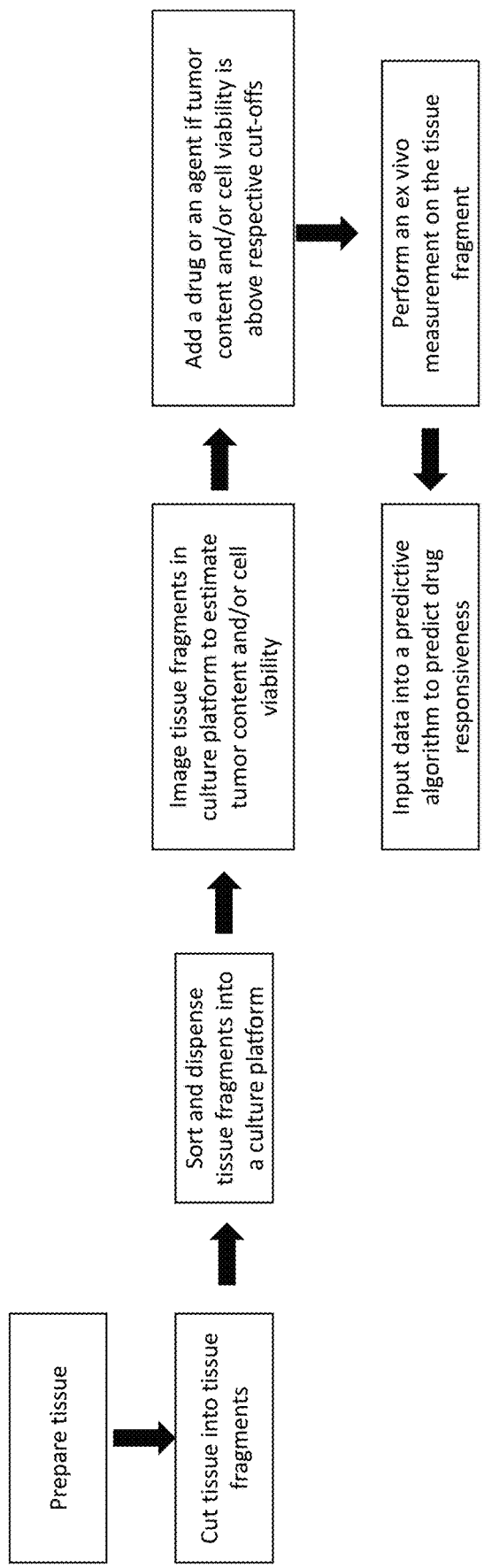
FIG. 1A-B represent functional block diagram of the workflow for determining the effect of a drug or an agent on a tissue.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

The phrase "and/or," as used herein in the specification and in the claims, should be understood to mean "either or both" of the elements so conjoined, e.g., elements that are conjunctively present in some cases and disjunctively present in other cases.

"Subject" as used herein is any mammalian or non-mammalian subject. The subject may be a primate or a non-primate subject. In some embodiments, the subject is suspected of or diagnosed with cancer. In some embodiments, the subject is a human subject. The cancer can be any solid or hematologic malignancy. The cancer can be of any stage and/or grade. Non-limiting examples of cancer include cancers of head & neck, oral cavity, breast, ovary, uterus, gastro-intestinal, colorectal, pancreatic, prostate, brain and central nervous system, skin, thyroid, kidney, bladder, lung, liver, bone and other tissues.

"Tissue" as used herein is a biological material obtained from a subject. In some embodiments, the tissue contains or is suspected of containing tumor cells (also referred to as a tumor containing tissue). The terms tumor cells, cancerous cells, and malignant cells have been used interchangeably. In some embodiments, the tissue is a solid tumor tissue. The tissue can be obtained from any organ or site in the body of the subject where a cancer has originated or where the cancer has metastasized to.

A tissue can be obtained from a subject by any approach known to a person skilled in the art. The tissue can be obtained by surgical resection, surgical biopsy, investigational biopsy, bone marrow aspiration or any other therapeutic or diagnostic procedure performed on a subject suspected of or diagnosed with cancer. While the tissue is expected to be a tumor cell containing tissue, there is no way of knowing the exact tumor content until the tissue has undergone pathology assessment, such as by hematoxylin and eosin (H & E) staining. Further, owing to the inherent heterogeneity of the tumor tissue, different fragments cut from the same tissue (tissue fragments) often have highly variable tumor content, and some tissue fragments may not have any tumor cells (or nearly zero tumor content). In such scenarios, determination of ex vivo drug response is not reliable and often does not yield statistically significant data. For example, if the tissue lacks an adequate number of malignant cells, that tissue may not adequately represent the response of the subject's tumor to the drug or the agent. Estimation of tumor content upfront on a live tissue fragment ex vivo, such as by a non-destructive imaging method, followed by addition of a drug or an agent to the imaged tissue fragment based on the estimated tumor content and/or analysis of the effect of the drug or the agent on the tissue fragments based on the estimated tumor content, were found to overcome the challenge. For example, a drug (or any other agent) is added if the estimated tumor content is above a threshold. In other embodiments, a tissue fragment may be included into or excluded from drug response analysis based on the tumor content of the tissue fragment. In still other embodiments, the data generated from one or more ex vivo measurements performed on the tissue fragments (for determination of drug response) may be normalized based on an upfront tumor content estimation of the tissue fragments. Further, lack of adequate number live or viable cells (such as viable tumor cells or immune cells) also gives rise to inconsistent data that confounds subsequent analysis. For example, addition of a drug to a tissue fragment that lacks an adequate number of viable tumor cells will not provide any analyzable insight into the functional response of the tumor to the drug. In some embodiments, an upfront determination of cell viability of the tissue fragments addresses the confounders arising out of these variabilities. For example, based on an upfront assessment, a drug (or any agents being tested) will be added if the tissue or the tissue fragments are determined to have adequate numbers of viable cells (such as viable tumor cells and/or viable immune cells). This will ensure that for each drug or agent being tested, a pre-determined number of replicates can be maintained, at each drug concentration being tested. For example, while doing a drug exposure-response study, it is important to ensure that every well of a well-plate is relevant (for example, the tissue fragment or fragments contained therein are determined to have adequate tumor content and cell viability), to ensure that a dose-response curve can be generated for calculating a EC50 or IC50. In some embodiments, a tissue fragment may be included into or excluded from drug response analysis based on the cell viability of the tissue fragment. In some embodiments, the data generated from one or more ex vivo measurements performed on the tissue fragments (for drug response analysis) may be normalized with respect to the cell viability of the tissue fragments.

Warm ischemia time as used herein refers to the time a tissue is at body temperature after blood supply has been cut-off, until it is excised from the body and placed at room temperature. Cold ischemia time as used herein refers to the time a tissue is at room temperature until it is placed in a suitable medium (such as, one of a transport medium, a preservation medium or a culture medium).

The term "cryopreservation" means preservation of a biological material (such as tissue or tissue fragment) at a temperature below the freezing temperature (such as at sub-zero temperature). A "cryopreserved tissue" or a "cryopreserved tissue fragment" refers to a tissue or a tissue fragment respectively, that has been preserved at temperature below the freezing temperature (such as at sub-zero Celsius temperature).

The terms "cryopreservation medium", or "freezing medium", refer to a medium in which a biological material is immersed before cryopreservation or freezing, or to medium which can be used to treat the biological material prior to freezing. A cryopreservation medium contains one or more cryoprotectants. In certain embodiments, a cryopreservation medium may be a freezing solution, a vitrification solution, and/or a mixture of such solutions. In certain embodiments, the cryopreservation medium refers to a medium for storing or freezing a biological material at a sub-zero Celsius temperature to sustain the viability of the tissue or the tissue fragments at that temperature.

A sub-zero Celsius temperature (or sub-zero temperature) is any temperature below 0° C., such as less than about −10° C., less than about −20° C., less than about −50° C., less than about −100° C., less than about −120° C., less than about −150° C. and so on. In some embodiments, sub-zero temperature is a temperature of liquid nitrogen, such as the boiling temperature of liquid nitrogen at atmospheric pressure. In some embodiments, sub-zero temperature is a temperature between about 0° C. and about −200° C. In some embodiments, sub-zero temperature is a temperature of about −196° C.

The term "hypothermic preservation" or "hypothermal preservation" mean preservation at a temperature below the physiological temperature (which is about 37° C.) but above the temperature of freezing, wherein biological processes are slowed down, thus allowing prolonged storage of a biological material. In some embodiments, hypothermic preservation is performed at temperatures between about 0° C. and about 10° C. A "hypothermally preserved tissue" or a "hypothermally preserved tissue fragment" refers to a tissue or a tissue fragment respectively, that has been preserved under hypothermic conditions. The terms "hypothermic preservation" and "cold preservation" have been used interchangeably. Similarly, the terms "hypothermic transport" and "cold transport" have been used interchangeably The term "hypothermic preservation medium" means a preservation composition that would allow the biological material to withstand a temperature below the physiological temperature, such as a temperature below 10° C. to sustain its viability at such temperature.

As used in one or more embodiments, preserving tissue or tissue fragments mean maintaining the tissue or tissue fragments under conditions wherein the viability of cells in the tissue or tissue fragments in sustained.

Tumor content is an ex vivo measure of tumor cells within the tissue or a tissue fragment generated from the tissue. The measure can be a qualitative determination or a quantitative determination of tumor cells or of tumor cell-containing regions of the tissue fragment. In some embodiments, tumor content is a fraction or a percentage of tumor cells within the tissue fragment. In some embodiments, tumor content is the number of tumor cells within the tissue fragment. Estimation of tumor content is performed on live tissue fragments, such as tissue fragments that have not been subjected to any tissue fixation techniques (such as formalin treatment) known to a person of ordinary skill in the art or not been stored under any condition or for any duration of time to significantly reduce the number of viable cells. Estimation of tumor content is done non-destructively, such as by imaging the tissue fragments. In some embodiments, by imaging the tissue fragments, an estimation of tumor content is done for each individual tissue fragment or for the entire tissue from which the tissue fragments are cut. In some embodiments, the estimation of tumor content is done by imaging individual cells within the tissue fragment. In some embodiments, the imaging is done at a plurality of focal planes at different depths within the tissue fragment. In some embodiments, estimation of tumor content is done without the addition of an exogenous label to the tissue fragment. Estimation of tumor content by imaging tissue fragments can be performed before drug or agent addition, and, if desired or required, at multiple timepoints after drug or agent addition. In some embodiments, an estimation of tumor content is done by enumerating the tumor cells. In some embodiments, an estimation of tumor content is done by determining the tissue area containing tumor cells. In some embodiments, an estimation of tumor content is done by determining the histology (such as tissue architecture, extracellular matrix (ECM) organization, stromal texture, cellular organization, cell morphology etc.) of live tissue fragments. In some embodiments, the histology of live tissue fragments is determined by imaging the live tissue fragments, utilizing the intrinsic emission from endogenous fluorophores like reduced forms of nicotinamide adenine dinucleotide or nicotinamide adenine dinucleotide phosphate (collectively called NAD(P)H) and/or second harmonic generation (SHG) arising from other endogenous molecules such as tissue collagen. In some embodiments, histology is determined manually. In some embodiments, the histology is determined by applying one or more machine learning algorithms such as on the images of live tissue fragments. In some embodiments, tumor content is estimated by evaluating the NAD(P)H intensity and/or lifetime composition images indicative of the cellular and/or tissue morphology, including but not limited to cell sizes and shapes, nuclei sizes and shapes, nucleus to cytoplasm area or volume ratios. In some embodiments, estimation of tumor content is provided by a determination of cellular organization or spatial heterogeneity within tissue fragments. Tissue fragments or regions of tissue fragments with cancerous cells are expected to be less ordered compared to tissue fragments or regions thereof, containing normal cells. In some embodiments, tumor content is estimated by quantifying a local entropy parameter of tissue fragments, such as by an analysis of images of tissue fragments. In some embodiments, an entropy parameter is a median entropy or an entropy skewness. In some embodiments, a tissue fragment or a region of a tissue fragment containing tumor cells have a higher median entropy compared to a tissue fragment or a region of a tissue fragment containing normal cells. In some embodiments, the entropy distribution is more negatively skewed in tumor cell-containing regions of the tissue fragment compared to normal regions. In some embodiments, the tumor content is determined from one or more components of the extracellular matrix (ECM), such as from an assessment of the collagen fibers. For example, a region containing tumor cells is characterized by a narrower width of collagen fibers compared to a region of normal cells.

In some embodiments, immune content is the number, fraction or percentage of immune cells (such as T-cells, natural killer cells, macrophages and the like) within the tissue or tissue fragment. In some embodiments, estimation of immune content is done by imaging the tissue fragment. In some embodiments, estimation of immune content is done without the addition of an exogenous label to the tissue fragment.

In some embodiments, a viability assessment is examining the tissue or tissue fragments for estimating the number, fraction or percentage of live and/or dead cells (such as tumor cells and/or immune cells). In some embodiments, a viability assessment is performed by imaging live tissue fragments. In some embodiments, viability assessment is performed by imaging live tissue fragments without the addition of an exogenous label. As used herein, "viable tumor content" is a measure of viable tumor cells, such as the number, fraction or percentage of viable tumor cells. As used herein, "viable immune content" is the measure of viable immune cells, such as the number, fraction or percentage of viable immune cells (such as T-cells or macrophages).

Cell viability is a measure of viable cells within the tissue or the tissue fragment. In some embodiments, cell viability is determined by imaging tissue fragments. In some embodiments, cell viability is determined by imaging the tissue fragments, from the intrinsic contrast provided by one or more endogenous labels.

A live tissue or a live tissue fragment is one in which the cells are viable. In some embodiments, a live tissue or a live tissue fragment is one in which the viability of cells is not significantly altered compared to tissue that is freshly excised from the subject. In some embodiments, a live tissue or a live tissue fragment is one which has not been subjected to any tissue fixation techniques (such as formalin fixation). According to some embodiments, viable cells are cells with an intact cell membrane. According to some embodiments, the cell membranes of viable cells are largely impermeable to certain viability test molecules such propidium iodide, 7-AAD and the like.

An exogenous label can be any agent that enhances the contrast during imaging. A skilled artisan can envisage multiple types of exogenous labels depending on the modality of imaging, non-limiting examples of which can include an optical label (e.g., a fluorescent label), a magnetic label, an acoustic label and the like. In some embodiments, the exogenous label is a fluorescent label. An exogenous label is one that is added to a tissue fragment. In contrast, an endogenous or intrinsic (used interchangeably) label is a naturally occurring molecule in the tissue fragment or originating from the tissue fragment. An endogenous label (used interchangeably with endogenous molecule) is an intrinsic, naturally occurring molecule within the tissue or the tissue fragment, which enhances the contrast while imaging the tissue fragments. In some embodiments, the endogenous label is an intrinsic fluorescent molecule (called an endogenous fluorophore) present within the tissue or the tissue fragment. An endogenous fluorophore is a naturally occurring fluorescent molecule in the tissue or the tissue fragment. Non-limiting examples of endogenous fluorophores include NADH (reduced form of nicotinamide adenine dinucleotide), NADPH (reduced form of nicotinamide adenine dinucleotide phosphate), flavins and flavin derivatives (such as flavin adenine dinucleotide (FAD)), aromatic amino acids such as tryptophan, tyrosine and the like. Other non-limiting examples of endogenous labels include second harmonic generation (SHG) structures like collagen, which are responsible for non-linear optical signals like second harmonic generation.

A drug is an anti-cancer drug or a combination of anti-cancer drugs or a combination of one or more anti-cancer drugs with a suitable adjuvant. In some embodiments, the anti-cancer drug is a targeted anti-cancer agent, such as a targeted antibody (such as anti-her2 antibody), an antibody fragment, bispecific antibody (such as bispecific T cell engager or BiTe), antibody-drug conjugates (such as trastuzumab emtansine) or a targeted small molecule (e.g., protein inhibitor, such as kinase inhibitor). In some embodiments, the anti-cancer drug is a cytostatic or cytotoxic agent, non-limiting examples of which include adriamycin, gemcitabine, palbociclib, docetaxel, fulvestrant, alpelisib, trametinib, cisplatin, carboplatin, oxaliplatin, exemestane, everolimus, vinorelbine, olaparib, capecitabine, cyclophosphamide, methotrexate, fluorouracil, mitomycin C, temozolomide, cetuximab, leucovorin, topotecan, irinotecan and any combination thereof. In some embodiments, the anti-cancer drug is an immunotherapeutic agent or drug, non-limiting examples of which include an immune checkpoint inhibitor or an immunostimulatory agent. In some non-limiting embodiments, the immunotherapeutic drug includes nivolumab, ipilimumab, pembrolizumab, atezolizumab, and any combination thereof. In some embodiments, the drug is an interfering RNA, such as small interfering RNA (siRNA) or short hairpin RNA (shRNA). In some embodiments, a drug can be a biological agent such as an oncolytic virus (such as talimogene laherparepvec) or a cellular therapy (such as chimeric antigen receptor (CAR)-T cell).

An "agent" refers to any compound, material, substance, or condition that provides a potential therapeutic benefit, either alone, or in combination with other therapeutic approaches. Agents need not be drugs. Agents include, but are not limited to, food and food products or components, endogenous molecules (e.g., gene expression products or hormones that are artificially induced), metabolites, radiation, heat, cold, oxygen or other gases, and the like.

A clinical parameter is an in-vivo parameter that provides an outcome of an anti-cancer treatment in a subject, that is a subject's actual clinical responsiveness to an anti-cancer treatment. In some embodiments, the clinical parameter is a tumor parameter, such as the size or metabolic activity of the tumor. In some embodiments, the clinical parameter is determined by a radiological assessment of the subject, such as by one or more of positron emission tomography (PET) scan, computerized tomography (CT) scan, magnetic resonance imaging (MRI) or the like. In some embodiments, the clinical parameter provides an outcome according to RECIST or modified RECIST criteria. In some embodiments, the clinical parameter provides a responsiveness on a continuous scale. In some embodiments, the clinical parameter is one or more of overall survival, disease free survival or progression free survival of the subject. Various other clinical parameters can be envisaged depending on the cancer type. In some embodiments, the clinical parameter is a biomarker (e.g., prostate-specific antigen (PSA) or other soluble factors). In some embodiments, the clinical parameter is minimum residual disease. In some embodiments, measuring clinical parameters comprises measuring factors such as cytokines. In some embodiments, a clinical parameter is circulating tumor DNA (ct-DNA) or circulating tumor cells (CTC). In some embodiments, clinical parameter measurement comprises the measurement of one or more clinical parameters. The clinical parameter can be measured at any timepoint after the initiation of the anti-cancer treatment. In some embodiments, the clinical parameter is measured at physician-determined intervals during or after the completion of the anti-cancer treatment. In some embodiments, the clinical parameter is measured after the completion of at least one cycle of the anti-cancer treatment. In some embodiments, an anti-cancer treatment comprises applying or administering a drug or other agent to or into the subject.

A tissue parameter is an ex vivo parameter of the tissue fragments obtained from an ex vivo measurement performed on the tissue fragments. In some embodiments, an ex vivo tissue parameter measurement is performed by imaging the tissue fragments. In some embodiments, an ex vivo tissue parameter includes genomic, transcriptomic or proteomic parameter of the tissue fragments. The phrases "tissue parameter" and "ex vivo tissue parameter" have been used interchangeably. An ex vivo parameter of the tissue fragments can be a cell parameter of the tissue fragments, an extracellular parameter of the tissue fragments or a combination of a cell parameter and an extracellular parameter of the tissue fragments. A "cell parameter" is any genomic, transcriptomic, proteomic, morphological, metabolic, functional, locational or dynamic parameter of a cell within a tissue fragment or an intracellular organelle thereof. Non-limiting examples of cell parameter include viability, motility, cell membrane permeability, DNA content and localization, cell death, metabolic activity, mitochondrial membrane potential, lipid molecule orientation in cell membrane, cellular activation state, cell proliferation, cell morphology, cell volume, cell size, or proximity and/or position of cells relative to each other. In some embodiments, the step of measuring a cell parameter comprises determining a cell type identity. The cell can be a tumor cell or a non-tumor cell (such as a stromal cell, an immune cell or any other cells within the tissue fragment). In some embodiments, the cell is a tumor cell. According to the various embodiments of the disclosure, measuring a cell parameter can comprise measuring one or more cell parameters of one cell, measuring one or more cell parameters of a plurality of cells (such as a plurality of tumor cells), or measuring one or more cell parameters of a plurality of cells of different types (such as a tumor cell and a non-tumor cell). In some embodiments, the measurement of cell parameter includes measurement of live/dead state of a tumor cell. In some embodiments, cell parameter includes activation state of an immune cell, such as a T-cell. In some embodiments, a cell parameter is measured by imaging. In some embodiments, the step of measuring a cell parameter comprises imaging the cells within a tissue fragment. In some embodiments, the step of measuring a cell parameter comprises imaging individual cells within a tissue fragment. In some embodiments, the cell parameter is measured by addition of an exogenous label to the tissue fragment. In some embodiments, the cell parameter is measured without the addition of an exogenous label to the tissue fragment, such as by imaging endogenous labels. In some embodiments, a tissue parameter is used to evaluate the effect of a drug or an agent on a subject's tissue.

An "extracellular parameter" is a parameter of the extracellular stroma, extracellular stromal components, secreted factors (such as cytokines) and the like. Non-limiting examples of extracellular stromal components include various proteins (such as collagen, elastin, fibronectin and others), proteoglycans, polysaccharides and the like. In some embodiments, an extracellular parameter is measured by imaging.

An ex vivo measurement performed on the tissue fragments (or an ex vivo tissue parameter measurement) can be a kinetic, non-destructive assessment of the tissue fragments treated with a drug or an agent, while the tissue fragments are still in culture. The ex vivo tissue parameter measurement can be a terminal assessment, performed on the tissue fragments on the termination of culture. Ex vivo tissue parameter measurement can be performed on live, intact tissue fragments, fixed tissue fragments, cell suspensions obtained from dissociated tissue fragments, secretions of cells of the tissue fragments and the like. Non-limiting examples of ex vivo tissue parameter measurement include imaging of live tissue fragments, flow cytometry analysis performed on cell suspensions obtained from dissociated tissue fragments, analysis of cytokine and other secreted factors etc.

In some embodiments, measuring a tissue parameter comprises measuring a cell parameter, measuring a plurality of cell parameters, measuring a cell parameter and an extra-cellular parameter or measuring one or more cell parameters and one or more extracellular parameters.

A data can be a structured data (such as a numeric data) or an unstructured data (such as an image). The data obtained from one or more ex vivo measurements performed on the tissue fragments is also referred to as a tissue parameter data or an ex vivo tissue parameter data. A tissue parameter data is obtained from an ex vivo tissue parameter measurement performed on a tissue fragment. In some embodiments, an ex vivo tissue parameter data comprises one or more cell parameter data. In some embodiments, an ex vivo tissue parameter data comprises one or more cell parameter data and one or more extracellular parameter data. The phrases "tissue parameter data" and "ex vivo tissue parameter data" have been used interchangeably. A cell parameter data is obtained from a cell parameter measurement. An extracellular parameter data is obtained from an extracellular parameter measurement. For example, if the cell parameter is cell viability, a cell parameter data can be the number or fraction of viable cells, or if the cell parameter is metabolic activity, the cell parameter data can be the ratio of fluorescence intensity of NAD(P)H to FAD. In some embodiments, an ex vivo tissue parameter data generated by microscopy is used alone or in combination with other data generated through microscopy for the purpose of auto-identifying cells (e.g. immune cells, cancer cells, epithelial cell and the like), determining the metabolic health of those cells (e.g. alive and healthy, apoptotic, dead or dying) and the tissue architecture (e.g. heavily structured with extracellular matrix elements, necrotic, degree of perfusion, and the like). A clinical parameter data is obtained from a clinical parameter measurement. Unless specifically mentioned, "data" can include singular or plural referents.

A cohort is a group of subjects sharing a common clinical feature. In some embodiments, the subjects within a cohort are suspected of or diagnosed with cancer. In some embodiments, all subjects within a given cohort are suspected of or diagnosed with the same cancer type. A training cohort is a group of subjects whose data (such as clinical parameter data and/or tissue parameter data) is used to train a predictive algorithm. A validation cohort is an independent group of subjects whose data (such as clinical parameter data and/or tissue parameter data) is used to validate the predictive algorithm. Clinical responsiveness of a subject to a drug or an agent provides an evaluation of the subject's responsiveness to the drug or the agent. In some embodiments, the clinical responsiveness can be a binned responsiveness such as a complete clinical response, a partial clinical response, a stable disease, or a progressive disease. In some embodiments, the clinical responsiveness is a continuous scale of responsiveness. An actual clinical responsiveness is an evaluation of a subject's clinical responsiveness after treatment of the subject with a drug or an agent based on an in-vivo measurement (such as a clinical parameter measurement) performed on the subject. A predicted clinical responsiveness is a prediction of a subject's clinical responsiveness based on an ex vivo measurement (such as an ex vivo tissue parameter measurement) performed on tissue fragments of the subject, wherein the tissue fragments are treated ex vivo with the drug or the agent.

Tissue fragments are obtained by cutting a tissue obtained from a subject. In some embodiments, the size of each tissue fragment is equal to or less than 1000 µm (such as 1000 µm, 500 µm, 450 µm, 400 µm, 350 µm, 300 µm, 250 µm, 200 µm, 100 µm or 50 µm) in at least one dimension. In some embodiments, the size of each tissue fragment is between 50 µm and 1000 µm in least one dimension. In some embodiments, the size of each tissue fragment is between 100 µm and 500 µm in at least one dimension. In some embodiments, the size of each tissue fragment is between 150 µm and 350 µm in at least one dimension. In some embodiments, the size of each tissue fragment is between 50 µm and 500 µm in at least two dimensions. In some embodiments, the size of each tissue fragment is between 150 µm and 350 µm in two dimensions. In some embodiments, the size of each tissue fragment is between 50 µm and 500 µm in all three dimensions. In some embodiments, the size of each tissue fragment is between 150 µm and 350 µm in all three dimensions. In some embodiments, the size of each tissue fragment is about 300 µm in any two dimensions and about 100 µm in the third dimension. In some embodiments, the size of each tissue fragment is about 300 µm in all three dimensions. In some embodiments, the tissue fragments are substantially cubical in shape. In some embodiments, the tissue fragments are uniform in size. As used herein, uniform means substantially uniform wherein the size of the tissue fragments are within ±20% of one another, in at least one dimension.

In some embodiments, the tissue, after being obtained from the subject, is first cut into tissue fragments. In some embodiments, the tissue fragments are placed in a suitable medium for extended preservation of cell viability, such as for transportation to a laboratory, where further processing of the tissue fragments takes place (such as sorting, imaging, culture etc.). In some embodiments, the tissue fragments are preserved under hypothermic preservation conditions. In some embodiments, the tissue fragments are preserved under cryopreservation conditions (such as at sub-zero temperature). In some embodiments, the tissue fragments are thawed for subsequent processing on reaching the destination site, such as a laboratory, where subsequent processing of the tissue fragments take place. In some embodiments, the tissue fragments are preserved under conditions, wherein after thawing, the viability of cells in the tissue fragments is not significantly reduced. In some embodiments, preservation of the tissue fragments under cryopreservation or hypothermic preservation conditions allows the tissue fragments to be stored for extended periods of time without significant reduction in cell viability or alterations in its metabolic profile. This allows great flexibility in the workflow and logistics. For example, it obviates any restriction of distance between the source site of tissue (such as a hospital) and the destination site (such as a laboratory) or of time elapsed between excision of the tissue and initiation of culture.

In some embodiments, the tissue is placed in a suitable medium for preservation before it is cut into tissue fragments. In some embodiments, the tissue is maintained under hypothermic preservation conditions in a suitable hypothermic preservation medium or under cryopreservation conditions in a suitable cryopreservation medium. In some embodiments, the hypothermally preserved or the cryopreserved tissue is transported to a destination site, such as the laboratory for further processing. In some embodiments, the tissue is cut into tissue fragments after transportation. In some embodiments, a cryopreserved tissue is thawed before being cut into tissue fragments.

A gel matrix can comprise a synthetic, a semi-synthetic or a natural component. In some embodiments, a gel matrix comprises at least one synthetic polymer or co-polymer, non-limiting examples of which includes poly(ethylene glycol) (PEG), poly(hydroxyethyl methacrylate) (PHEMA), poly(vinyl alcohol) (PVA), poly(acrylic acid) (PAA), poly (lactic acid), poly(caprolactone), poly(methycrylic acid) (PMMA), poly(lactic-co-glycolic acid) (PLGA), polyhydroxybutyric acid-valeric acid, poly(ethylene glycol)-diacrylate, poly(ethylene glycol)-vinyl sulfone and the like. In some embodiments, the polymers or co-polymers are further functionalized A gel precursor is a component that forms the gel matrix under suitable conditions of gelation. The gel precursor can be in any physical form such as in liquid or in solid form. In some embodiments, the gel matrix is formed by a covalent cross-linking of the gel precursors, while in some other embodiments the gel matrix is formed by a physical aggregation of the gel precursors. In some embodiments, depending upon the tissue type the percentages of the gel precursors and/or gelation conditions can be varied to obtain gel matrices of varying mechanical stiffness. In some embodiments, a gel matrix is formed when the gel precursor is irradiated with a light source. In some embodiments a gel matrix is formed when the gel precursor is subjected to a temperature change. While a skilled artisan can envisage multiple types of suitable gel matrices and gelation conditions, preferably the process of gelation to form the gel matrix should be fast and under conditions that cause minimal damage to the tissue or tissue fragments and that are inert to biological molecules. Further, the process of gelation and/or the gel matrix should not significantly alter the biological behavior of the cells in the tissue fragment. In some embodiments, gelation to form the gel matrix happens in less than 5 min (such as 4 min, 3 min, 2 min, 1 min or 30 second).

In some embodiments, the gel precursor is a PEG polymer such as a linear or a branched PEG polymer. A particularly suitable functionalized polymer can be, for example, a multi-arm, branched PEG polymer, such as a four-arm or an eight-arm PEG with terminal hydroxyl (—OH) groups that is functionalized with norbornene. In some embodiments, gelation to form the gel matrix happens in the presence of a suitable cross-linker such as a di-thiolated molecule (e.g., bi-functional PEG-dithiol). In some embodiments gel formation happens when the norbornene-functionalized multi-arm PEG polymer and bi-functional PEG-dithiol are irradiated with a light source. In some embodiments, the gel matrix further comprises an exogenous optical label, such as a fluorescent label. The fluorescent label can be covalently attached to the gel matrix or non-covalently embedded into the gel matrix.

A sacrificial casing is a casing that holds the tissue during cutting. In some embodiments, the tissue encapsulated within the gel matrix is contained within the sacrificial casing. In some embodiments, the sacrificial casing is formed of a material that can be cut with a cutting mechanism. Non-limiting examples of materials of the sacrificial casing include polypropylene, wax, silicone (such as Polydimethylsiloxane (PDMS)) and various thermoplastic elastomers. The material should preferably be biocompatible and non-toxic to avoid damaging or altering the tissue properties. In some embodiments, the sacrificial casing further comprises an exogenous label, such as a fluorescent label. In some embodiments, the sacrificial casing comprises a hollow cavity to house the tissue within. In some embodiments, the sacrificial casing comprises a groove to hold the tissue.

A culture platform is any suitable culture device or system for culturing tissue fragments. Non-limiting examples of a culture platform include a well-plate or a fluidic device. In some embodiments, the culture platform comprises an oxygen-permeable material. Various types of oxygen-permeable materials may be employed. In some embodiments, the oxygen-permeable material comprises a fluoropolymer, non-limiting examples of which include FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof. In some embodiments, the oxygen-permeable material comprises cyclic olefin polymer (COP) and cyclic olefin copolymers (COC). In some embodiments, the oxygen-permeable material comprises a silicone material (e.g., polydimethylsiloxane (PDMS)). In some embodiments, the culture platform is formed of extremely thin sections of one or more oxygen-permeable material. In some embodiments, regions of culture platform include chambers of the culture platform. Chambers of the culture platform can be wells of a well-plate or channels of a fluidic device. In some embodiments, the culture platform is configured for perfusion culture. In some embodiments, the culture platform is configured for non-perfused, static culture. In some embodiments, the culture platform is formed of a material that is optically transparent, thereby allowing optical investigation of the tissue fragments while the tissue fragments are within the chambers of the culture platform.

Imaging the tissue fragments can be performed with one or more imaging modalities. In some embodiments, at least one imaging modality of the one or more imaging modalities is configured for imaging with spatial resolution equal to or less than 20 μm (such about 20 μm, 10 μm, 5 μm, 2 μm, 1 μm, 0.5 μm, 0.2 μm, 0.1 μm and the like) in a 3-dimensional array of points (voxels). In some embodiments, at least one imaging modality is configured for imaging with spatial resolution less than or equal to 2 μm. In some embodiments, at least one imaging modality is configured for imaging with submicron level spatial resolution (such as 0.1 to 0.999 μm) in a 3-dimensional array of points. In some embodiments, the imaging modality is configured to image at different depths of the tissue fragments. In some embodiments, at least one imaging modality is configured for non-destructive imaging of the tissue fragments. In some embodiments, at least one imaging modality is configured to image live tissue fragments (such as tissue fragments that have not been subjected to any tissue fixation techniques or not been stored under any condition or for any duration of time to significantly reduce the number of viable cells). In some embodiments, at least one imaging modality is configured to image unstained tissue fragments (e.g., tissue fragments which do not contain any exogenous label). In some embodiments, one or more imaging modalities are part of an imaging system. In some embodiments, the imaging system comprises at least two imaging modalities.

In some embodiments, at least one imaging modality is configured for interferometric imaging. In some embodiments, imaging is performed with an imaging device configured for optical coherence tomography (OCT). In some embodiments, the OCT imaging device is configured for imaging with a spatial resolution less than 2 μm. While different types of high-resolution OCT approaches can be contemplated, in some embodiments, the imaging device is configured for full-field OCT (FF-OCT). In some embodiments, the imaging device is configured for OCT acquired using a scanned beam of light. In some embodiments, an imaging device configured for FF-OCT comprises an interferometer (e.g., Linnik, Mirau, Michaelson type), a light source of low temporal coherence (e.g., LED, thermal light, tungsten filament lamp and the like) and a detector (e.g., CCD, CMOS and the like). The FF-OCT imaging device is configured to obtain 2-dimentional (2D) images at different depths. In some embodiments, one or more system components of the FF-OCT imaging device can be displaced to move the focal plane at different depths within the sample in order to obtain 2D images at different depths.

In some embodiments, at least one imaging modality is configured for fluorescence imaging. In some embodiments, the imaging modality is configured for multiphoton excitation (either 2 or 3 photon excitation) of fluorescence molecules to accomplish imaging or confocal fluorescence imaging or imaging employing the use of a scanned plane of light (using 1, 2, or 3 photon excitation of fluorescent molecules). In some embodiments, the imaging modalities configured for fluorescence imaging comprises a light source (e.g., laser such as a pulsed laser employing a Titanium Sapphire gain medium and optics to generate and ultrafast pulse, or a picosecond pulsed laser, or any ultrafast pulsed laser of pulse duration 30 to 500 fs), a scanner (e.g.

one or more galvanometer mirror(s), or a rotating polygon mirror, or a resonant galvanometer mirror, and the like), and a detector (e.g., a charge coupled device (CCD), a CMOS based detector, an avalanche photodiode or a photomultiplier tube (PMT, or a hybrid PMT) and the like). In some embodiments, the fluorescence imaging modality comprises a light source configured to excite with an excitation wavelength in the range of preferably between 600 to 1700 nm. In some embodiments, the fluorescence imaging modality is configured for imaging with micron (e.g., 1 to 20 µm) and/or submicron (e.g., 100-999 nanometer, that is 0.1 to 0.999 µm) level spatial resolution in a 3-dimensional array of points (voxels). In some embodiments, the fluorescence imaging modality is configured to detect intrinsic emission (such as autofluorescence of molecules naturally present in biological tissue, that is endogenous labels). In some embodiments, the imaging modality is configured to detect second harmonic scattered light generated by components in the tissue fragments. In some embodiments, second harmonic scattered light is generated as the components interact with ultrafast pulsed laser light (30 to 500 fs) or pulsed laser light of picosecond pulse duration which subsequently propagate both through the sample and which are scattered back towards the excitation laser source. In some embodiments the imaging modality is configured to measure the fluorescence lifetime of intrinsic fluorescent labels using one or more approaches (hereafter Fluorescent Lifetime Imaging or FLIM) (e.g., time correlated single photon counting, frequency domain methods, gated detection of photons, and the like). In some embodiments the imaging modality is configured to detect the polarization of emitted and scattered fluorescent light. In some embodiments, excitation light, which is circularly or elliptically polarized is used to perform Mueller matrix imaging. In some embodiments the generated images are deconvolved to enhance image resolution.

Figure 1B:
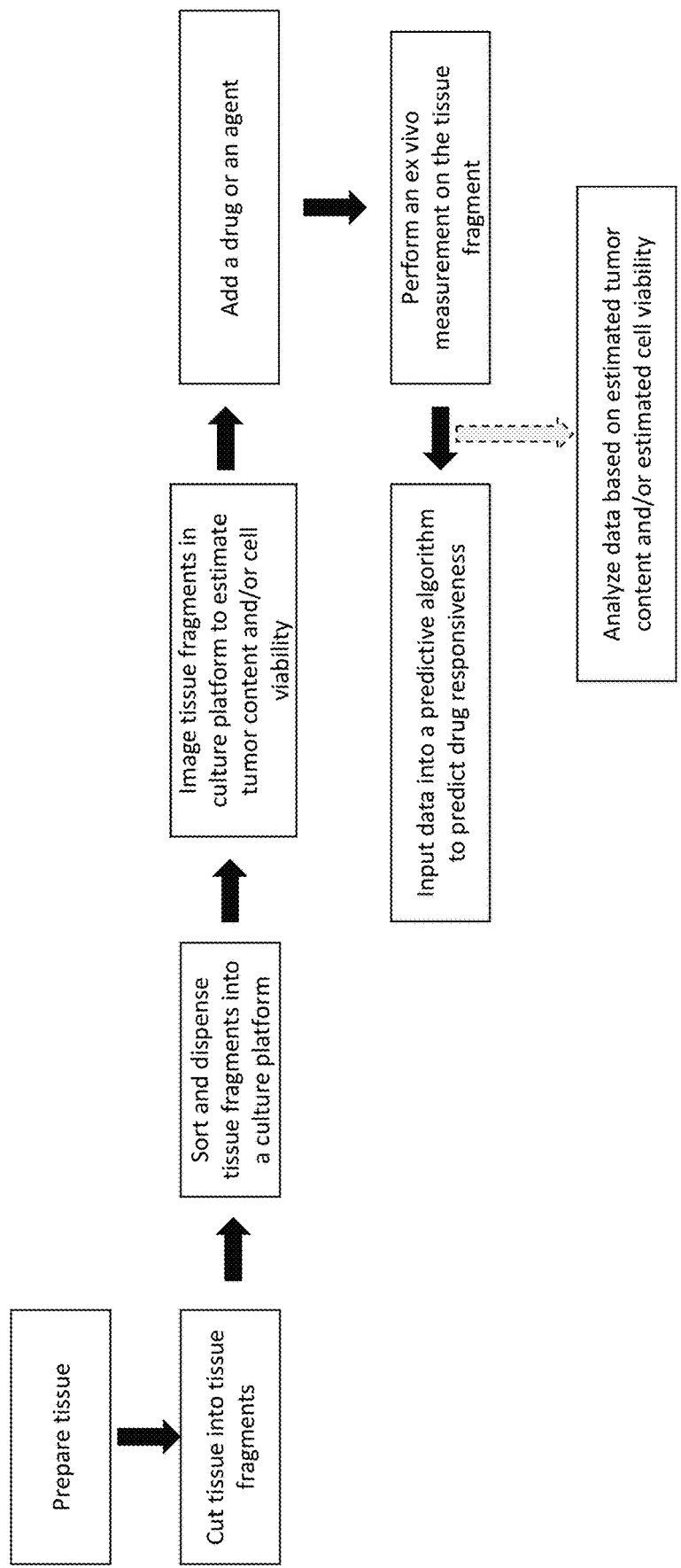

Some embodiments relate to an ex vivo method of determining the effect of a drug or an agent on a tissue, the method comprising: cutting a tissue into tissue fragments; sorting the tissue fragments based on a characteristic (e.g., an optical characteristic) of the tissue fragments and dispensing a controlled number of tissue fragments into the chambers of a culture platform after sorting; imaging the tissue fragments which are dispensed into the chambers of the culture platform to estimate one or more of tumor content or cellular viability of the tissue fragments; adding a drug or an agent to the tissue fragments and determining the effect of the drug or the agent on the tissue fragments based on data from one or more ex vivo measurements performed on the tissue fragments. In some embodiments, the drug or the agent is added to the tissue fragments based on one or more of the estimated tumor content or cell viability (such as shown in FIG. 1A). In some embodiments, the data from the one or more ex vivo measurements is analysed based on one or more of the estimated tumor content or cell viability (such as shown in FIG. 1B).

Figure 4A:
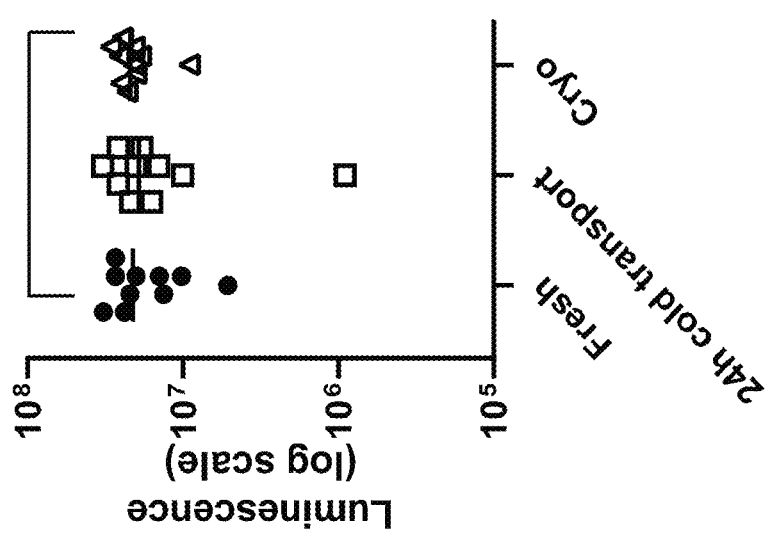
FIG. 4A shows cell viability in tumor fragments maintained under hypothermal (cold) preservation condition, cryopreservation condition, and in fresh tissue fragments. Cryo: cryopreservation. Cold transport: simulated cold transport condition, wherein the tumor fragments are maintained under conditions of hypothermal preservation. Fresh: tissue fragments not subjected to any preservation conditions.
Figure 4B:
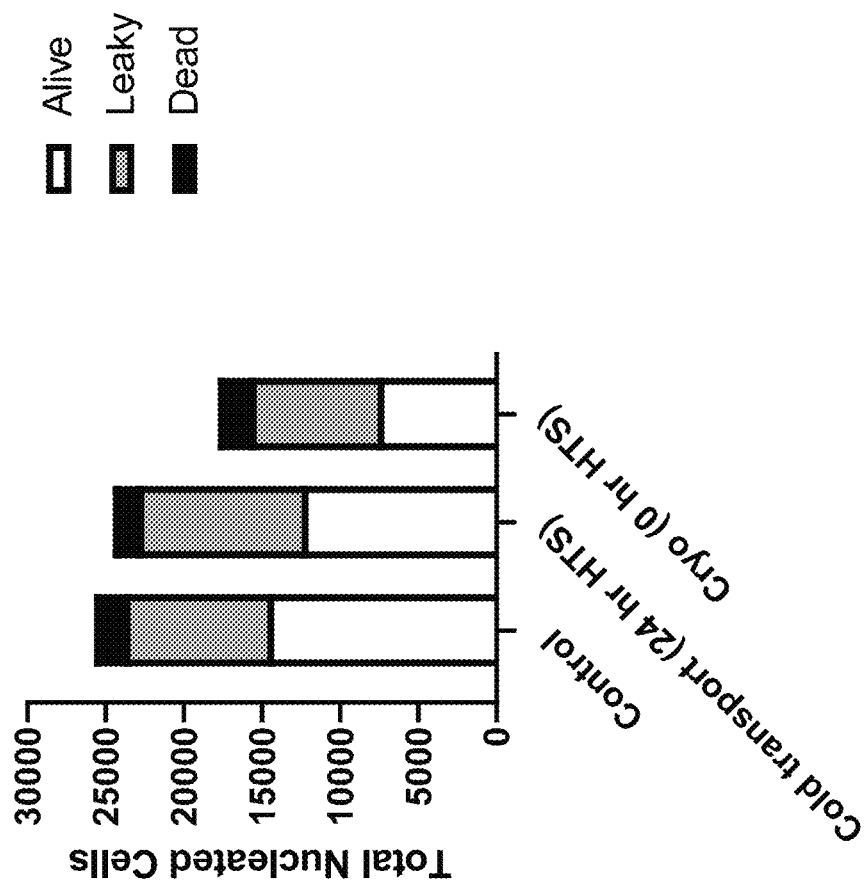
FIG. 4B shows the numbers of live, dead and leaky nucleated cells in control (fresh) tissue fragments, tissue fragments maintained under hypothermic conditions (Cold transport) and cryopreservation conditions (Cryo).
Figure 4C:
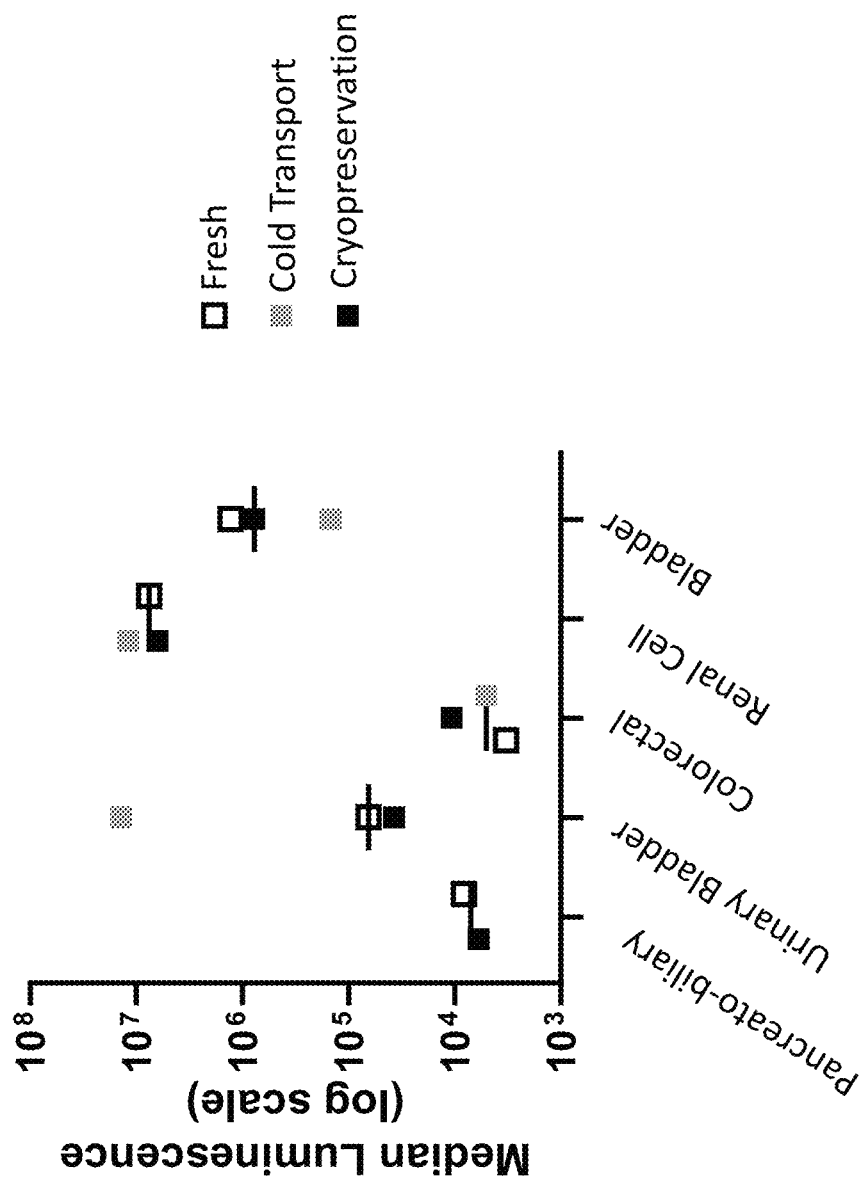
FIG. 4C shows cell viabilities in human tissue fragments maintained under hypothermal preservation condition (cold transport), cryopreservation condition (cryo), and in fresh tissue fragments (fresh). Five different tumor types from five different patients were selected.

In some embodiments, the tissue after being removed from the subject (such as by biopsy), or tissue fragments, are placed in a suitable medium for preservation. The tissue or the tissue fragments can be subjected to cryopreservation or hypothermic preservation conditions. The viability of cells in the tissue fragments are not significantly altered after hypothermal preservation compared to the viability of cells in fresh tissue fragments (as shown in FIG. 4A-C). This was observed in both mouse (FIG. 4A) and human (FIG. 4C) tumor tissue samples. In some embodiments, the tissue or the tissue fragments are cryopreserved. In some embodiments, the tissue or the tissue fragments are maintained under cryopreservation conditions for an extended period of time, such as for 24 hours or more. The cryopreserved tissue or the tissue fragments are then thawed for subsequent processing. In some embodiments, even if cryopreservation causes some reduction in the number of live cells (FIG. 4B), there are still adequate numbers of live cells for subsequent studies, such as functional assessment of drug response.

In some embodiments, the tissue is cut into tissue fragments after being excised from the subject (such as by surgical excision). In some embodiments, the step of cutting the tissue into tissue fragments is performed at or close to the source site of the tissue (e.g., the hospital where the tissue is excised from the subject). In some embodiments, the tissue fragments are placed in a suitable medium (such as a hypothermic preservation medium or a cryopreservation medium). In some embodiments, the hypothermally preserved or the cryopreserved tissue fragments are transported to a destination site (e.g., a laboratory where the tissue is further processed). In some embodiments, cryopreserved tissue fragments are thawed (such as at 37° C.) before performing the subsequent processes (such as sorting, imaging, culturing etc.). In some embodiments, after cutting, the tissue fragments are preserved under cryopreservation condition at temperature between about −120° C. and about −200° C. In some embodiments, the tissue fragments are preserved or stored under cryopreservation conditions for at least 24 hours (such as for 24 hours, 48 hours, 72 hours or more). This ensures that tissue fragments obtained from the tissue of a patient can be stored for extended periods of time, for future assessment.

Figure 5B:
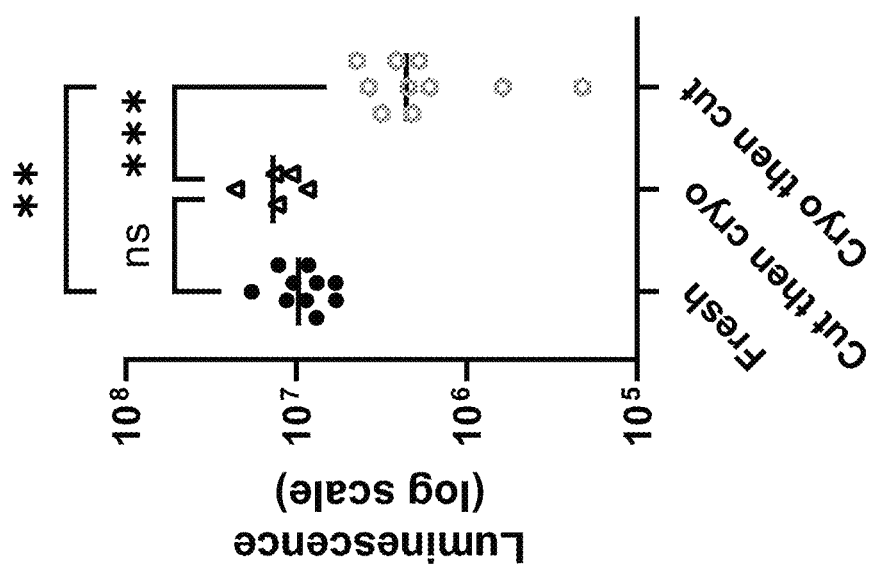
FIG. 5B shows comparison of cell viability under conditions where tissue was cut into tissue fragments prior to cryopreservation (cut then cryo) versus cryopreservation of tissue prior to cutting (cryo then cut). The two conditions were further compared to fresh tissue fragments (fresh).

It was found that when tissue (such as surgically excised tissue) was first cut into tissue fragments and the tissue fragments were transported or preserved under hypothermic preservation condition (such as between 0° C. and 10° C.), the viability of cells was higher, compared to when the bulk tissue was hypothermally preserved before cutting. For example, in FIG. 5A, the viability of cells in the "cut then cold transport" group was higher than in the "cold transport then cut" group. Similarly, as shown in FIG. 5B, when tissue was first cut into tissue fragments and the tissue fragments were cryopreserved (cut then cryo), the viability of cells was higher compared to the condition when the bulk tissue was cryopreserved before cutting (cryo then cut).

The step of cutting can be manual, semi-automated or automated. Various suitable cutting devices may be employed for cutting the tissue. In some embodiments, the cutting device is configured to cut the tissue precisely and with minimal mechanical damage to the tissue or the tissue fragments. In non-limiting examples, cutting devices comprises a knife, a blade, a wire, a scalpel, a laser, and the like. In some embodiments, the cutting device comprises a plurality of blades. In some embodiments, the cutting device comprises a coated wire, such as a diamond particle coated steel wire (such as a diamond wire). In some embodiments, the cutting device comprises uniformly spaced wires (such as diamond wires or naked steel wired). In some embodiments, the cutting device comprises a cutting component. In some embodiments, the cutting component comprises at least one cutting member such as a knife, a blade, a wire, a scalpel, a laser, and the like. In some embodiments, the cutting device comprises three cutting components to cut the tissue in three dimensions, wherein each cutting component cuts the tissue in one dimension. The cutting device is configured to accurately and precisely cut a tissue into tissue fragments of a defined size. In some embodiments, the cutting device is configured to cut the tissue into tissue fragments based on a size input received from the user (user-defined). In some embodiments, the user-defined size input is based on physical properties of the tissue such as mechanical stiffness, frangibility and the like. In some embodiments, the cutting device is configured to cut the tissue into tissue fragments based on a pre-defined size input. In some embodiments, the cutting device is configured to cut the tissue into tissue fragments automatically and repeatedly until the entire tissue is cut into tissue fragments. In some embodiments, the cutting device is configured to cut the tissue into tissue fragments that are equal in size. As used herein, equal means substantially equal wherein the sizes of the tissue fragments are within ±20% of one another, in at least one dimension. In some embodiments, depending on the firmness of the tissue, the cutting device or components thereof are vibrated or rotated at user-defined or pre-defined frequency. The fragmentation settings of the cutting device such as thickness of tissue fragment, frequency, amplitude, speed etc. are user-defined or pre-defined.

Figure 6B:
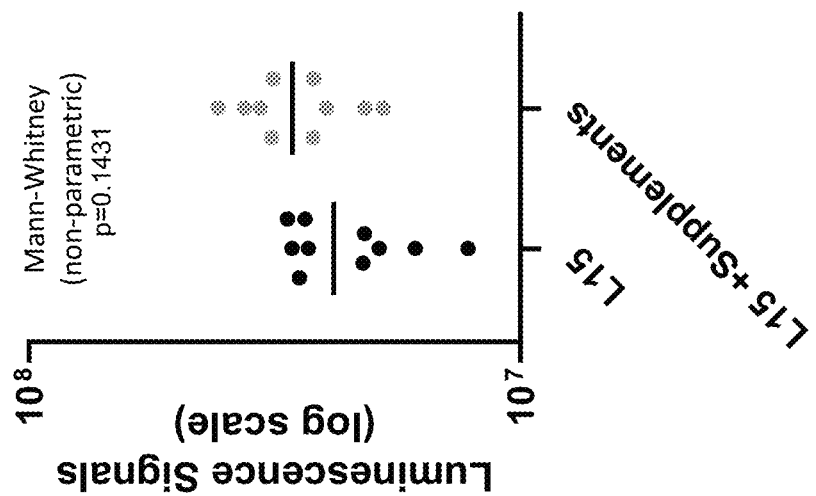
FIG. 6B shows viability of tissue fragments cut under condition where cutting medium (with oxygenation of cutting medium) was supplemented with glutathione and HEPES buffer (L15+Supplements) versus tissue fragments cut under condition where cutting medium (with oxygenation) was not supplemented with glutathione and HEPES buffer (L15).
Figure 6A:
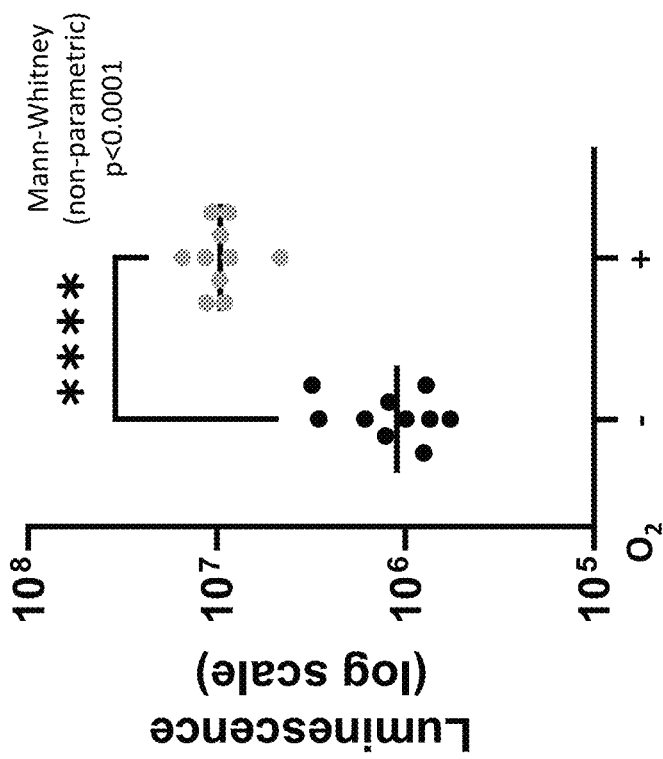
FIG. 6A shows viability of tissue fragments cut under condition where cutting medium was oxygenated during tissue cutting process ($O_2+$) versus viability of tissue fragments cut under condition where excess oxygen was not provided during the tissue cutting process ($O_2-$). On the x-axis, $O_2$ (−) denotes cutting condition where oxygen was not bubbled through cutting medium and $O_2(+)$ denotes cutting condition where oxygen was bubbled through the cutting medium.

In some embodiments, the tissue is cut under conditions of high oxygen concentration, that is an oxygen concentration greater than ambient oxygen concentration (such as greater than 21% or greater than 30% or greater than 50% or greater than 70%, or greater than 90% and the like). In some embodiments, the tissue is cut into tissue fragments in an oxygenated cutting medium. In some embodiments, this was achieved by bubbling $O_2$ through the medium used for cutting (or the cutting medium). It was found that oxygenated cutting medium ($O_2$ medium) was better than non-oxygenated cutting medium (non-$O_2$ medium) in preserving viability of the tissue fragments (FIG. 6A). In some embodiments, the cutting buffer is further supplemented with additives such as glutathione to protect the tissue and the tissue fragments from oxidative damage (FIG. 6B).

In some embodiments, the tissue is prepared before cutting. In some embodiments, the tissue is encapsulated in a gel matrix. In some embodiments, the tissue is encapsulated in a suitable adhesive or sealant. In some embodiments, the step of cutting comprises cutting the tissue encapsulated in the gel matrix. In some embodiments, the gel matrix is labelled with a fluorescent label. In some embodiments, the tissue is contained within a sacrificial casing. In some embodiments, the sacrificial casing is labelled with a fluorescent label. While the gel matrix, the sacrificial casing, or both help to hold and stabilize the tissue during cutting, it is preferable not to have any trace of either during culture of the tissue fragments since residual gel matrix or residual sacrificial casing can interfere with nutrient availability, drug response and/or downstream analysis of the tissue fragments. In some embodiments, residual gel matrix, residual sacrificial casing or both are removed before the tissue fragments are dispensed into the chambers of the culture platform. In some embodiments, the step of cutting comprises driving the sacrificial casing containing the tissue towards the cutting component of the cutting device or driving the cutting component of the cutting device towards the sacrificial casing containing the tissue, wherein the cutting device cuts the tissue into tissue fragments by cutting through the sacrificial casing. In some embodiments, the tissue is further encapsulated in a gel matrix.

Some embodiments relate to sorting and selecting tissue fragments that are suitable for culture and drug response assessment. In some embodiments, sorting is done with an optical sorter for examples as described in US patent publication U.S. Pat. No. 6,657,713B2, herein incorporated by reference in its entirety. The optical sorter comprises an illumination source. In some embodiments, the illumination source comprises one or more lasers. The optical sorter further comprises a detector (e.g., photodiode, photomultiplier tube, charged-coupled device (CCD) camera and the like) and a flow cell. A flow cell comprises a fluidic path through which the tissue fragments pass. The light from the illumination source is directed towards one or more sensing zones within the flow cell.

Figure 2:
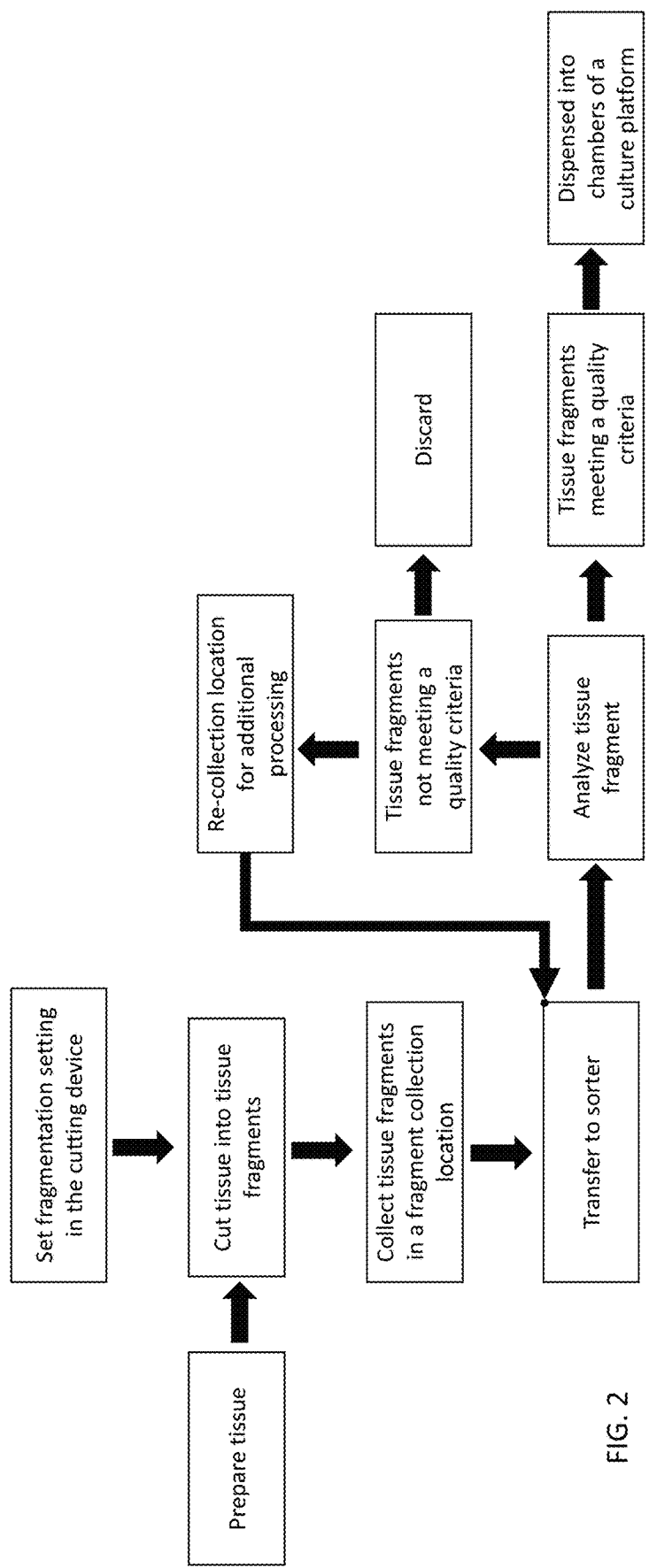
FIG. 2 represents a flow diagram of the workflow involving fragmentation and sorting according to an embodiment.

In some embodiments, after cutting, the tissue fragments are automatically directed for sorting. In some embodiments, the tissue fragments are directed for sorting in a user-driven manner. In some embodiments, after cutting, the tissue fragments are collected in a fragment collection location. In some embodiments, the tissue fragments are collected in a fluid (such as buffer or culture medium) in the fragment collection location. In some embodiments, a transferring device, such as an autosampler, aspirates the tissue fragments from the fragment collection location and transfers them into the sorter. In some embodiments, the transfer to the sorter occurs through an in-line filtration element. The tissue fragments are sorted based on a characteristic of the tissue fragments. In some embodiments, the tissue fragments are sorted based on an optical characteristic of the tissue fragments. An optical characteristic can include one or more of fluorescence, reflectance, absorbance or light scattering. In some embodiments, the tissue fragments are suspended in a suitable fluid (such as a buffer or a culture medium) and passed through one or more light beams (such as laser beam) traversing the flow cell. In some embodiments, the tissue fragments are passed in a single file. As each tissue fragment passes through the light beam (e.g., in the sensing zone), an optical signal, indicative of an optical characteristic of the tissue fragment, is detected. The detector signals are processed and used to operate a suitable flow diverting means (e.g., a fluidic switch) that is located downstream from the sensing zone. In some embodiments, the optical characteristic is indicative of one or more of size of the tissue fragment, integrity of the tissue fragment, presence or tissue debris or presence of an exogenous agent (such as an exogenous label, traces of residual gel matrix etc.) within the tissue fragments. In some embodiments, sorting removes one or more of residual gel matrix, residual sacrificial casing, tissue debris, disintegrated tissue fragments or tissue fragments not meeting a size criterion. Based on the optical characteristic, a tissue fragment is either dispensed into the chamber of a culture platform or directed into a waste disposal. In some embodiments, based on the optical characteristic, the tissue fragment can also be directed to a third or re-collection location for additional processing, inspection, or recovery. In some embodiments, the process of sorting comprises analyzing each tissue fragment based on a characteristic (e.g., an optical characteristic) of the tissue fragment, dispensing into chambers of a culture platform the tissue fragments meeting a quality criterion and discarding the tissue fragments not meeting the quality criterion (FIG. 2). In some embodiments, the tissue fragments not meeting the quality criterion (undesirable fragments) are directed for additional processing. In some embodiments, the quality criterion is based on one or more of, tissue fragment size, presence of tissue debris, damaged tissue, presence of exogenous agents (e.g., contaminants such as residual sacrificial casing or residual gel matrix). In some embodiments, the tissue fragments that are dispensed into the chambers of the culture platform meet one or more criteria selected from desired size, integrity (tissue fragments that are not damaged or folded), absence of multiplets and the absence of exogenous agents. "Multiplets" as used herein, mean multiple independent tissue fragments clumped together and flowing as a group in the flow cell, or uncut or partially cut fragments constituting two or more adjacent pieces of tissue that would have otherwise been cut into independent fragments but remained together. Absence of multiplets further ensures that a controlled number of tissue fragments can be dispensed into the chambers of the culture platform.

In some embodiments, the step of dispensing the tissue fragments into the chambers of a culture platform comprises dispensing a controlled number of tissue fragments into each chamber of a culture platform. In some embodiments, the step of dispensing the tissue fragments into the chambers of a culture platform comprises dispensing one tissue fragment into each chamber of a culture platform. In some embodiments, the step of dispensing the tissue fragments into the chambers of a culture platform comprises dispensing more than one tissue fragment into each chamber of a culture platform. In some embodiments, the tissue fragments which are dispensed into the chambers of the culture platform are further embedded in a gel matrix. In some embodiments, the tissue fragments are dispensed into chambers of the culture platform, wherein the chambers are pre-filled with a gel precursor. In some embodiments, a gel precursor is added to a chamber after one or more tissue fragments are dispensed into it. In some embodiments, the gel precursor is subjected to suitable conditions of gelation to form a gel matrix, wherein the tissue fragment or fragments are embedded within the gel matrix. In some embodiments, the gel precursors are photo-polymerizable and the step of gelation comprises photo-irradiation of the gel precursors containing the tissue fragment or fragments therein.

In some embodiments, the tissue fragments which are dispensed into the chambers of the culture platform after sorting (or sorted tissue fragments) meet the required size criteria and are free of one or more of exogenous agents (such as residual gel matrix, residual sacrificial casing), tissue debris, disintegrated tissue fragments, multiplets or tissue fragments not meeting a size cut-off. The gating strategies used for sorting have been shown in FIG. 7-FIG. 14. These tissue fragments are useable for further downstream processes or are the useable tissue fragments. As used herein, free means substantially free. As understood by a person of ordinary skill, even if sorting does not completely remove the above stated components (such as residual gel matrix, sacrificial casing, tissue debris, disintegrated tissue fragments), their levels are reduced substantially such that the downstream processes performed on the tissue fragments (e.g., culture or tissue parameter measurement) are not affected. The step of dispensing the tissue fragments into chambers of a culture platform or directing them into waste disposal or for additional processing can be done by diverting the flow of the fluid containing the tissue fragments in a controlled manner. Various suitable flow diverting means can be contemplated for diverting the flow in a controlled manner, while ensuring minimal damage to the tissue fragments. Such methods may include the use of suitable fluid switches and other valves. In some embodiments, the tissue fragment is sorted again after the step of additional processing.

In some embodiments, the steps of cutting, sorting and dispensing the tissue fragments into the chambers of a culture platform happen within a closed system. This ensures maximum sterility of the tissue fragments throughout the entire process. In some embodiments, the process of cutting is performed in one system and the tissue fragments are sorted in a separate system.

Figure 15:
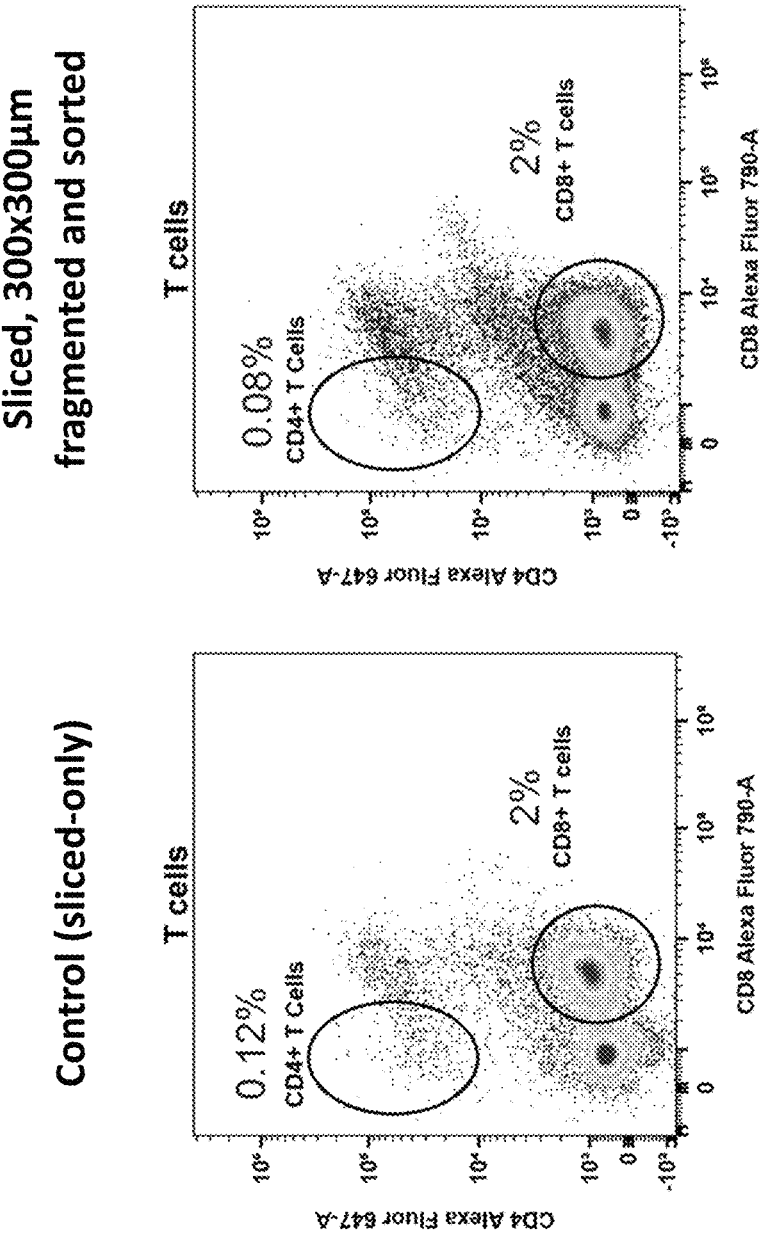
FIG. 15 shows effect of cutting and sorting of tissue fragments on the number of tumor infiltrating lymphocytes (TIL).

In some embodiments, the optical characteristic is fluorescence. As the tissue encapsulated within a gel matrix (and optionally contained within the sacrificial casing) is cut into tissue fragments, a fraction of the tissue fragments, particularly the ones cut from the periphery, contains residual portions of the gel matrix or the sacrificial casing or both. In some embodiments, the gel matrix, the sacrificial casing or both are labelled with a fluorescent label. As the tissue fragments pass through the laser beam, they are sorted based on the fluorescence of the fluorescent label. The tissue fragments in which the fluorescence of the fluorescent label is not detected are dispensed into the chambers of a culture platform. The tissue fragments in which the fluorescence of the fluorescent label is detected are directed into a waste disposal or to a re-collection location for additional processing. In some embodiments, the step of additional processing includes removal of one or more of damaged portions of the tissue fragments, multiplets, traces of residual gel matrix or residual sacrificial casing. As shown in FIG. 15, the steps of cutting and sorting preserve the content of tumor infiltrating lymphocytes (TIL). The numbers of CD4+ and CD8+ T cells were not significantly altered in tissue fragments that were cut and sorted according to one or more embodiments cited herein, compared to control tissue that were not subjected to these processes.

In some embodiments, the step of imaging the tissue fragments to estimate the tumor content is performed after the tissue fragments are sorted and dispensed into the chambers of the culture platform (that is, on sorted tissue fragments). In some embodiments, the step of imaging the tissue fragments comprise optically interrogating each chamber of the culture platform to image the tissue fragment or fragments contained therein. In some embodiments, imaging is done with an imaging device configured for one or more of FF-OCT or spectral OCT, or an imaging device configured for fluorescence imaging, fluorescence lifetime imaging, transmitted light imaging, or reflected light imaging. In some embodiments, the imaging device is configured for imaging with micron (e.g., 1 to 20 µm) level spatial resolution in a 3-dimensional array of points and/or a sub-micron level spatial resolution. In some embodiments, the imaging device is configured for imaging with a spatial resolution equal to or less than 10 µm (such about 10 µm 5 µm, 2 µm, 1 µm, 0.5 µm, 0.2 µm, 0.1 µm and the like). In some embodiments, the imaging device is configured for imaging with a spatial resolution equal to or less than 5 µm (such about 5 µm, 2 µm, 1 µm, 0.5 µm, 0.2 µm, 0.1 µm and the like). In some embodiments, the imaging device is configured for imaging with a spatial resolution equal to or less than 2 µm (such about 2 µm, 1 µm, 0.5 µm, 0.2 µm, 0.1 µm and the like).

In some embodiments, the estimation of tumor content is done by imaging live tissue fragments, without the addition of an exogenous fluorophore. In some embodiments, the step of imaging comprises imaging live tissue fragments using one or more of fluorescence emission, fluorescence lifetime, fluorescence lifetime composition, or second harmonic imaging of one or more endogenous labels. In non-limiting examples, the endogenous label is NAD(P)H, FAD, collagen, or other second harmonic generating molecules. In some embodiments, fluorescence lifetime composition refers to the composition of one or more populations of an endogenous fluorophore distinguished by fluorescence lifetimes. In some embodiments, fluorescence lifetime composition refers to the relative compositions of one or more populations of an endogenous fluorophore distinguished by fluorescence lifetimes. In some embodiments, the fluorescence lifetime composition of NAD(P)H is the composition of a short fluorescence lifetime component (with lifetime between about 0.2 and 1 nanoseconds (ns)) and a long fluorescence lifetime component (with lifetime between about 1 and 5 ns). In some embodiments, the fluorescence lifetime composition of NAD(P)H is expressed as the percentage of the short fluorescence lifetime component with respect to the total fluorescence lifetime components of NAD(P)H.

In some embodiments, the method comprises imaging the live tissue fragments without the addition of an exogenous label to obtain label-free, live tissue images. In some embodiments, the estimation of tumor content comprises a histologic assessment of the label-free, live tissue image, wherein the step of histologic assessment comprises identifying regions of tumor cells and normal cells within the live tissue fragments.

Figure 16:
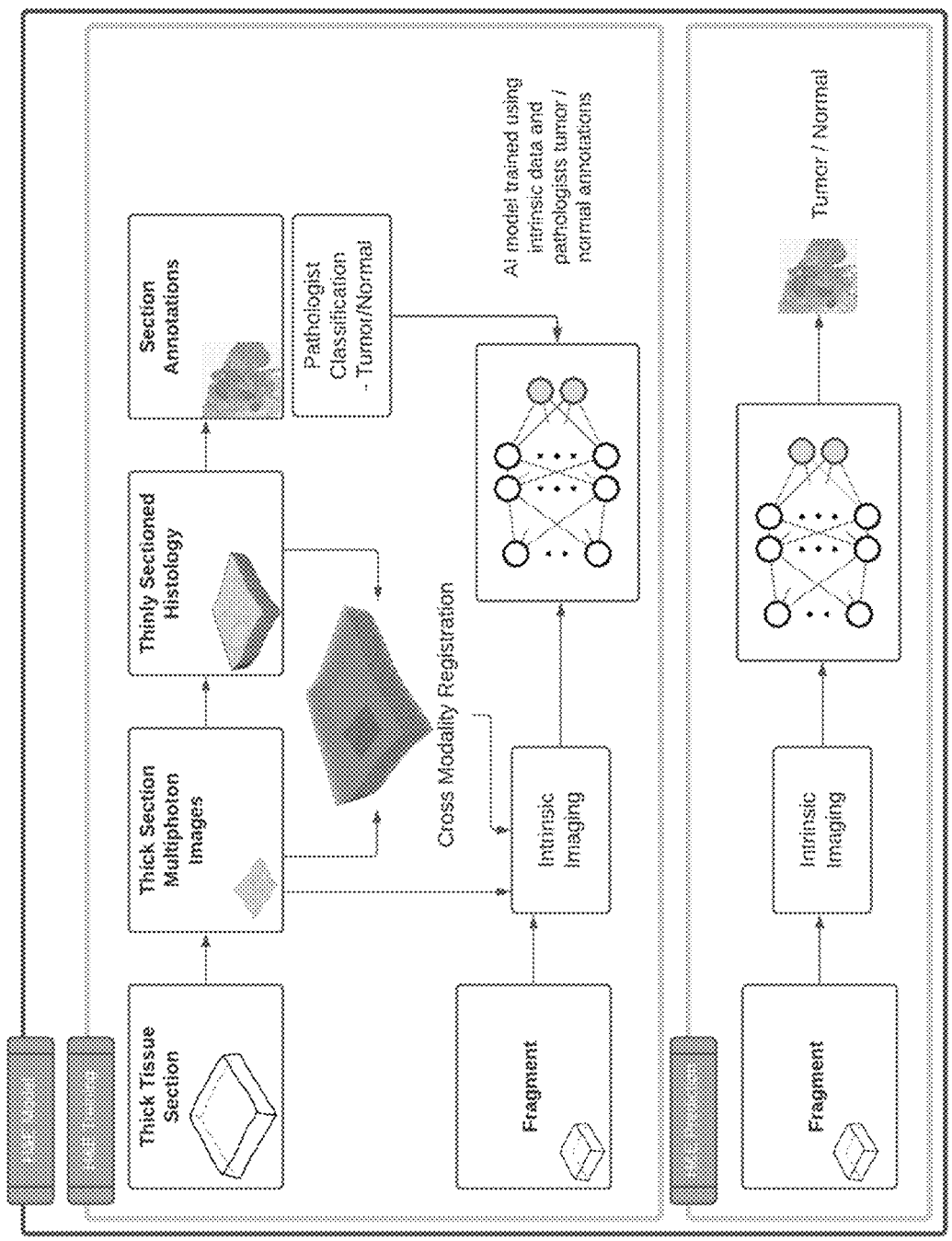
FIG. 16 shows a representative diagram for developing a machine learning algorithm (AI model) for identifying regions of tumor cells and normal in label-free images of live tissue fragments.

"Live tissue images" as used herein, are images of live tissue or live tissue fragments. In some embodiments, the images are obtained by non-linear microscopy methods, based on techniques such as multi-photon fluorescence (e.g., 2- or 3-photon imaging), second harmonic generation and others. In some embodiments, the live tissue images are label-free (exogenous label-free), fluorescence images obtained from the emission of endogenous tissue fluorophores (such as NAD(P)H, FAD, elastin etc.), fluorescence lifetime of endogenous fluorophores, and/or second harmonic generation arising from endogenous molecules like, collagen. The histological assessment can be done manually or can be done in an automated or a semi-automated manner using image processing software. In some embodiments, the step of histologic assessment of label-free, live tissue images comprises applying a machine learning algorithm on the label-free, live tissue images to identify regions of tumor cells and normal cells, wherein the machine learning algorithm is trained on a plurality of training tissue images (such as shown in FIG. 16). The training tissue images comprise label-free, live tissue images and matched, annotated, stained tissue images.

In some embodiments, the image processing software executes the trained, machine learning algorithm, such as based on deep neural network. In non-limiting embodiments, the stained tissue images can be hematoxylin and eosin (H&E) stained, trichrome stained, or labelled with immunohistochemical (IHC) stains. In some embodiments, the stained tissue images are manually annotated (such as by one or more trained pathologists), to identify regions of normal cells (normal) and regions of tumor cells (tumor). The pathologist annotated stained tissue images constitute the ground truth for training the algorithm. From each live tissue fragment that is imaged to produce a live tissue image, a plurality of tissue sections is cut, which are subsequently stained, imaged and annotated, to produce matched, annotated, stained tissue images. In some embodiments, training the algorithm further comprises cross-modality image registration of label-free, live tissue images of tissue fragments and stained tissue images of matched tissue sections. The training tissue images are generated from a training set of tissue fragments. In some embodiments, the training set of tissue fragments is different from the tissue fragments on which the effect of a drug or an agent is determined. In some embodiments, the training set of tissue fragments are of the same tissue type as the tissue fragment on which the effect of the drug or the agent is determined. For example, for determining the ex vivo drug efficacy on a tissue fragment cut from a lung tumor tissue, the machine learning algorithm for estimating tumor content will be trained on a training set of tissue fragments, also obtained from lung tumor tissue. In some embodiments, the algorithm executed on the image processing software may be used to automatically identify or segment regions of interest within the live tissue images. In some embodiments, the algorithm may be used to perform histopathological assessment of the live tissue fragment, such as by identifying histological features indicative of tumor and normal in the live tissue images. In some embodiments, the algorithm may further be used to virtually or digitally stain the live tissue images.

In some embodiments, as shown in FIG. 16, for training the model (correlative histology model), live tissue fragments (such as belonging to training set of tissue fragments), of thickness between about 100 µm and about 1 mm, are imaged using intrinsic (exogenous label-free) multi-photon microscopy. Multiple fields of view (FOV) are imaged in three dimensions and stitched to generate a section of data over a reasonable range of the tissue fragment. The tissue fragment is then thinly sectioned (serial sectioning) as per standard histological processes and stained (e.g., using H&E). All the stained sections are then imaged on a standard brightfield slide scanner. The stained, serial sections are then registered to each other to generate a volume (termed as the 3-D volume) that represents the original 3-dimensional tissue fragment as closely as possible. Cross-modality registration is performed between the multiphoton intrinsic section and the 3-D volume. The section of histology data (from the stained tissue sections) that matches the section of multiphoton data are presented to pathologists for annotations that form tumor/normal labels for model training Multiple datasets generated from intrinsic data (label-free, live tissue image) and the stained, annotated images from matched tissue sections are used as inputs to the machine learning models. For correlative histology model prediction, intrinsic multiphoton imaging data from live tissue fragments are acquired. The machine learning algorithm is used to predict tumor and normal (or the tumor/normal probability).

In some embodiments, the step of imaging for estimation of tumor content comprises one or more of fluorescence emission or fluorescence lifetime imaging of an endogenous fluorophore, wherein the step of estimation of tumor content comprises quantifying the spatial heterogeneity of the endogenous fluorophore using one or more entropy parameters. In some embodiments, the step of estimation of tumor content comprises quantifying the spatial heterogeneity of fluorescence intensities of the endogenous fluorophore, using one or more entropy parameters. In some embodiments, the endogenous fluorophore is NAD(P)H. Non-limiting examples of entropy parameters include median entropy, entropy skewness, kurtosis, and standard deviation. The entropy parameters are differentiated between a tissue fragment or a region of tissue fragment containing tumor cells versus a tissue fragment or a region of tissue fragment containing normal cells (FIG. 17C, Table 1). In some embodiments, a tissue fragment or a region of a tissue fragment containing tumor cells have a higher median entropy compared to a tissue fragment or a region of a tissue fragment containing normal cells. In some embodiments, a tissue fragment or a region of a tissue fragment containing tumor cells have an entropy distribution that is more negatively skewed compared to a tissue fragment or a region thereof containing normal cells.

Figures 17A, 17B:
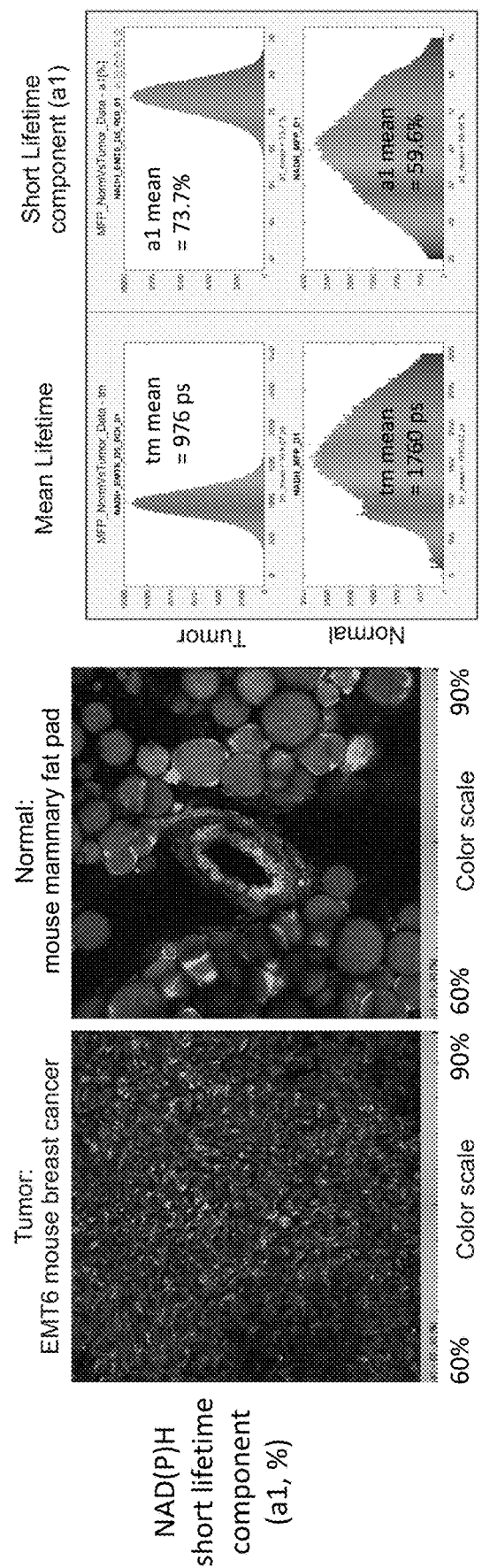
Figure 17C:
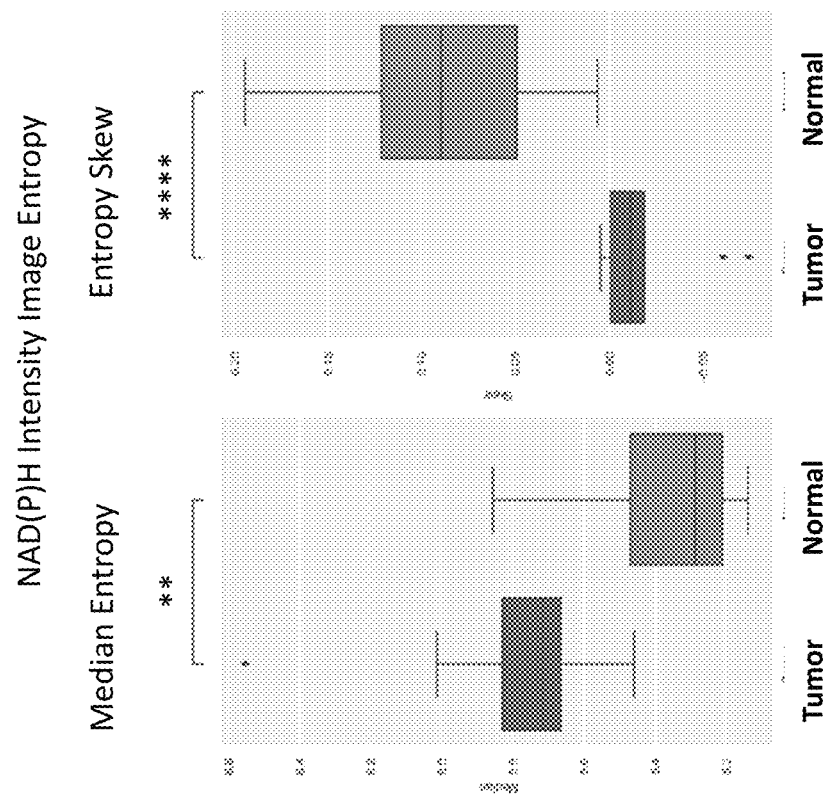

In some embodiments, as shown in FIG. 17A-B, the step of imaging comprises fluorescence lifetime imaging of NAD(P)H, and wherein the step of estimation of tumor content comprises quantifying the mean lifetime (tm) of NAD(P)H and/or the mean amplitude of the short fluorescence lifetime component (a1 mean) of NAD(P)H. In some embodiments, the mean tm (or tm mean) is higher in a tissue fragment or a region of a tissue fragment containing normal cells compared to a tissue fragment or a region thereof containing tumor cells. In some embodiments, the mean amplitude of the short lifetime component (or a1 mean) is higher in a tissue fragment or a region of a tissue fragment containing tumor cells compared to a tissue fragment or a region thereof containing normal cells.

In some embodiments, the step of imaging comprises second harmonic generation (SGH) imaging of a second harmonic generation (SHG) structure such as an ECM fiber, and wherein the step of estimation of tumor content comprises determination of a fiber parameter of the SGH structure. In some embodiments, the fiber parameter is fiber width, fiber straightness or fiber length. In some embodiments, the fiber parameters of a SHG structure are differentiated in a tissue fragment or a region of a tissue fragment containing tumor cells compared to a tissue fragment or a region of a tissue fragment containing normal cells. In some embodiments, a tissue fragment or a region of a tissue fragment containing tumor cells is characterized by narrower width, greater straightness and/or greater average length of collagen fibers compared to a tissue fragment or a region thereof containing normal cells (FIG. 17D). A "second harmonic generation structure" or "SHG structure" used herein is an endogenous molecule (such as an ECM component) that gives rise to second harmonic generation. Non-limiting examples of SGH structure include collagen, myosin etc.

In some embodiments, the step of adding a drug or an agent to the tissue fragments comprises adding a drug or an agent based on the estimated tumor content. In some embodiments, adding a drug or an agent based on the estimated tumor content comprises adding a drug or an agent to a tissue fragment based on the estimated tumor content of that tissue fragment. For example, a drug or an agent is added to a tissue fragment if the estimated tumor content of said tissue fragment is equal to or greater than a cut-off. In some embodiments, adding a drug or an agent based on the estimated tumor content comprises adding a drug or an agent to the tissue fragments contained within a chamber of a culture platform based on the estimated tumor content of a minimum number of tissue fragments within that chamber. For example, a drug or an agent is added to the tissue fragments contained within a chamber if the estimated tumor content of a minimum number of tissue fragments within that chamber is equal to or greater than a cut-off. In some embodiments, adding a drug or an agent based on the estimated tumor content comprises adding a drug or an agent to the tissue fragments based on the estimated tumor content of the tissue (which in turn is obtained by imaging the tissue fragments and estimating the tumor content of the tissue fragments cut from said tissue). For example, a drug or an agent is added if a minimum number of chambers contain a tissue fragment or fragments with tumor content equal to or greater than a cut-off. Hence, in some embodiments, the upfront estimation of tumor content is utilized for determining whether or not to add the drug or the agent to the tissue fragments.

In some embodiments, the cut-off for tumor content (or the tumor content cut-off) is based on the number or percentages of malignant cells. In some embodiments, the tumor content cut-off is based on one or more surrogate parameters of tumor content such as an entropy parameter (such as the median entropy, entropy skewness etc.), an ECM fiber parameter (such as width, straightness and average length of SHG structures like collagen fibers), one or more fluorescence parameters of an endogenous fluorophore (such as fluorescence lifetime and/or emission intensity of one or more lifetime components of NAD(P)H) etc.

Figure 3:
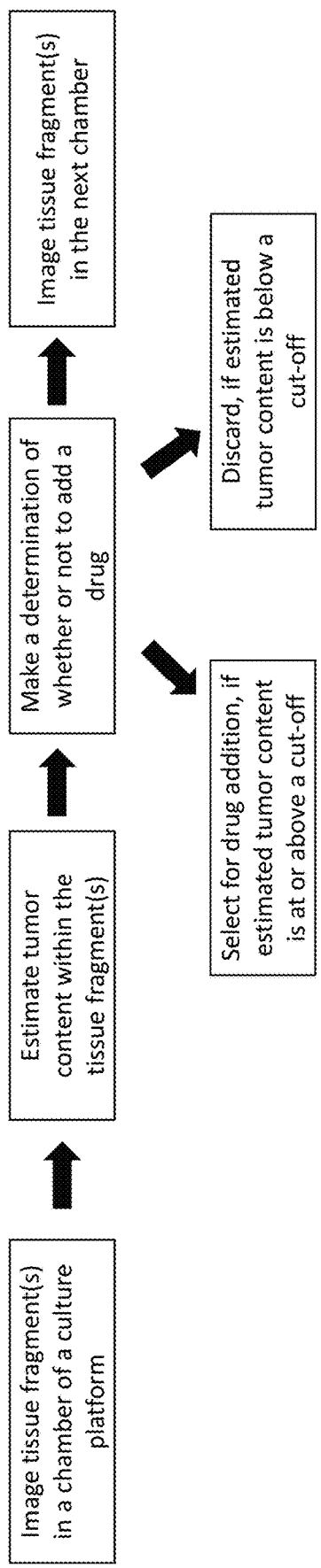
FIG. 3 represents a flow diagram of the workflow involving tumor content estimation and drug or other agent addition based on the estimated tumor content according to an embodiment.

In some embodiments, the step of adding a drug or other agent based on the estimated tumor content comprises imaging a tissue fragment in a chamber of a culture platform to estimate the tumor content of the tissue fragment, selecting the tissue fragment for drug or other agent addition if the estimated tumor content is at or above a cut-off and discarding the tissue fragment if the estimated tumor content is below a cut-off, and imaging a tissue fragment in the next chamber of the culture platform to estimate the tumor content (such as shown in FIG. 3). The cut-off can be a pre-defined cut-off (wherein the cut-off is pre-set and remains constant irrespective of tissue variables such as warm and cold ischemic times, size, nature, type, metabolic status, immune content etc. of the tissue fragments, type of drug or other agent to be added, culture condition, culture time and the like) or a user-defined cut-off (wherein the user sets the cut-off depending upon one or more tissue variables as stated above). In some embodiments, the cut-off (such as based on the percentage of tumor cells) is 1%. In some embodiments, the step of drug or other agent addition is automatic if the estimated tumor content exceeds the cut-off. In some embodiments, the step of drug or other agent addition is user-defined. In some embodiments, the drug or other agent is added to a tissue fragment if the percentage of tumor cells within the tissue or the tissue fragment is at least 1% (such as 1% or 5%, or 6% or 7% or 10% or 20% or 50%, 70%, 75%, 80%, 85%, 90%, 95%, 100% and the like). In some embodiments, the drug or other agent is added to a tissue or a tissue fragment if the percentage of tumor cells within the tissue fragment is at least at least 5%, for example the percentage of tumor cells within the tissue fragment is 1% or 5%, or 6% or 7% or 10% or 20% or 50%, 70%, 75%, 80%, 85%, 90%, 95% and the like.

Some embodiments further comprise estimating an immune content of each tissue fragment. In some embodiments, the drug (e.g., an immunomodulator) or other agent is added if the estimated immune content is equal to or greater than a cut-off (such as an immune content cut-off). In some embodiments, the drug or other agent is added if immune cells (such as cytotoxic T cells, effector T cells, NK cells and the like) are detected in the tissue fragment.

Figures 18A, 18B, 18C, 18D:
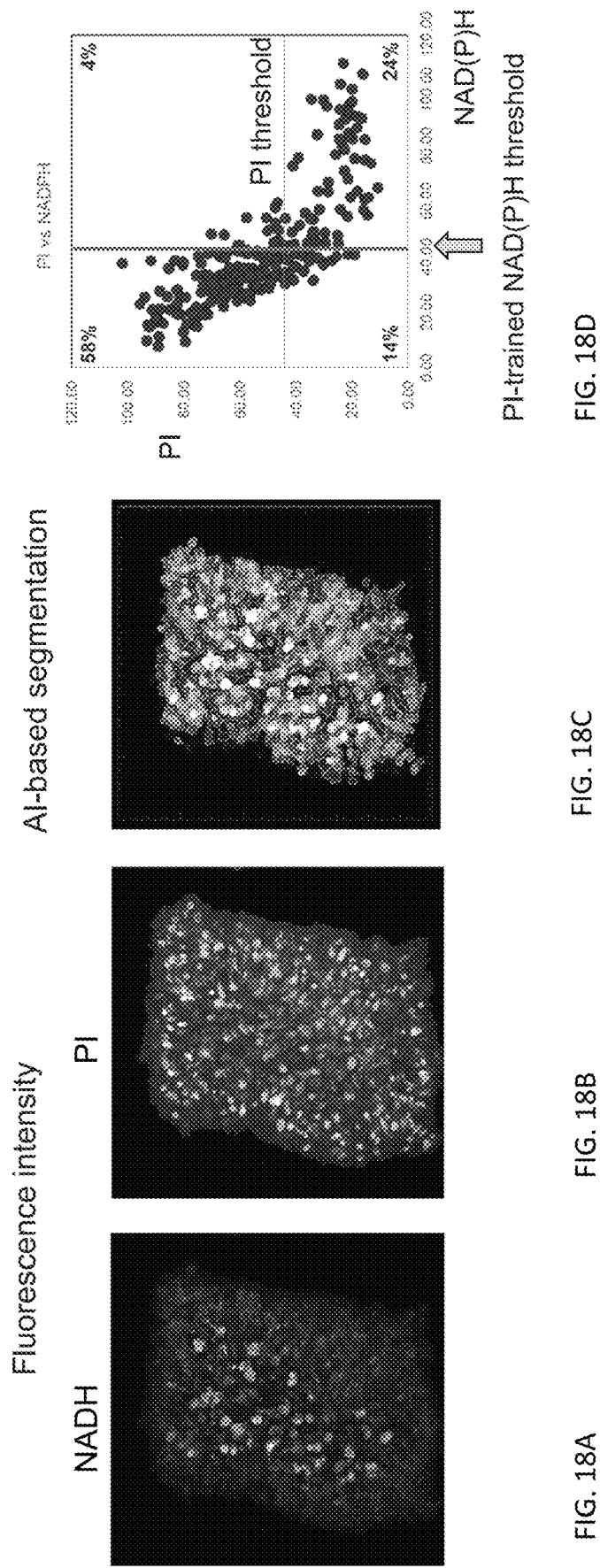
FIG. 18A-D show label-free imaging of NAD(P)H fluorescence emission intensity for distinguishing live from dead cells in live tissue fragments.

Some embodiments comprise performing a viability assessment of the tissue fragments to determine the cell viability. In some embodiments, the step of adding a drug or an agent to a tissue fragment comprises adding the drug or the agent if the cell viability is equal to or greater than a cut-off (cell viability cut-off). In some embodiments, viability assessment comprises imaging the tissue fragments. In some embodiments, viability assessment comprises imaging the tissue fragments to detect one or more signals (such as one or more optical signals) from an endogenous molecule, which is indicative of cell viability. In some embodiments, the cell viability cut-off is determined from one or more signals from the endogenous molecule. In some embodiments, the step of viability assessment comprises imaging the tissue fragments to measure the fluorescence emission intensity and/or the fluorescence lifetime of an endogenous fluorophore. In some embodiments, the endogenous fluorophore is indicative of live or viable cells. In some embodiments, the greater the number of live cells, greater is the emission intensity of the endogenous fluorophore (such as NAD(P)H fluorescence shown in FIG. 18A). In some embodiments, the cell viability cut-off is determined from the fluorescence emission intensity of the endogenous fluorophore. In some embodiments, the method further comprises adding the drug or the agent if the fluorescence intensity of the endogenous fluorophore is greater than an intensity threshold. In some embodiments, the cell viability cut-off is provided by the intensity threshold of the endogenous fluorophore. In some embodiments, the intensity threshold is determined using a training set of tissue fragments labelled with an exogenous label that stains dead cells (such as PI fluorescence shown in FIG. 18B). The exogenous label for dead cells serves as the ground truth. In some embodiments, the intensity threshold of the endogenous fluorophore is trained on the intensity of the exogenous label for dead cells. In some embodiments, the steps to train the intensity threshold of the endogenous fluorophore comprises determining first an intensity threshold of the exogenous label. In some embodiments, an intensity threshold of the endogenous fluorophore is set such that >90% of the exogenous label-high cells (identified by the intensity threshold of the exogenous label) are excluded by the intensity threshold of the endogenous fluorophore (FIG. 18C-D). In some embodiments, the endogenous fluorophore is NAD(P)H. In some embodiments, the exogenous label is propidium iodide (PI), which stains the nucleus of dead cells. In some embodiments, the training set of tissue fragments is different from the tissue fragments on which the effect of the drug or the agent is determined. In some embodiments, the training set of tissue fragments is of the same tissue type as the tissue fragments on which the effect of the drug or the agent is determined. In some embodiments, the intensity threshold of the endogenous fluorophore is determined before each experiment, wherein the training set of tissue fragments and the tissue fragments on which the effect of the drug or the agent is determined, are cut from the same tissue.

In some embodiments, the drug or the agent is added if there are sufficient numbers or percentages of viable cells (or cell viability is equal to or greater than a cut-off) as determined from the intensity threshold of the endogenous fluorophore. In some embodiments, the viability assessment is performed by imaging the tissue fragments. In some embodiments, if a tissue fragment is estimated to have viable cells (or cell viability is equal to or greater than a cut-off), a drug or an agent is added to the tissue fragment. In some embodiments, where a chamber contains more than one tissue fragment, if a minimum number of tissue fragments within the chamber is estimated to have viable cells (or have cell viability equal to or greater than a cut-off), a drug or an agent is added to the tissue fragments contained within that chamber. In some embodiments, if a minimum number of chambers contain tissue fragments with viable cells (or with cell viability equal to or greater than a cut-off), a drug or an agent is added to the tissue fragments.

In some embodiments, the step of adding a drug or other agent to the tissue fragments comprises adding different dilutions of the drug or other agent to different tissue fragments. In some embodiments, the drug is a combination of two or more drugs. In some embodiments, the two or more drugs (or agents) are added concurrently. In some embodiments, the two or more drugs (or agents) are added sequentially. In some embodiments, the drug or the combination of drugs is added with a suitable adjuvant or excipient. In some embodiments, the drug (or agent) is added in a single bolus dose, while in some other embodiments, the drug (or agent) is added in smaller doses at defined intervals. In some embodiments, the step of adding a drug (or an agent) to the tissue fragments comprises adding different drugs or drug combinations (or different agents or different combinations of agents) to different tissue fragments.

In some embodiments, the tissue fragments are cultured. The tissue fragments are cultured in any suitable culture medium. The tissue fragments are cultured in the presence of the drug or the agent. In some embodiments, the tissue fragments are cultured for at least 12 hours (such as for 12 hours or 24 hours, or 48 hours, or 72 hours, or 96 hours, or 120 hours or the like). The tissue fragments lack a functional blood supply and lymphatic vasculature. The tissue fragments are cultured under conditions of optimum oxygen concentration, such as depending upon the tissue type. In some embodiments, the tissue fragments are cultured under conditions of high oxygen concentration. In some embodiments the tissue fragments are cultured under conditions of at least 20% oxygen (such as 20%, or 30% or 40% or 50% or 60% or 70% or 80% and the like).

Figure 19A:
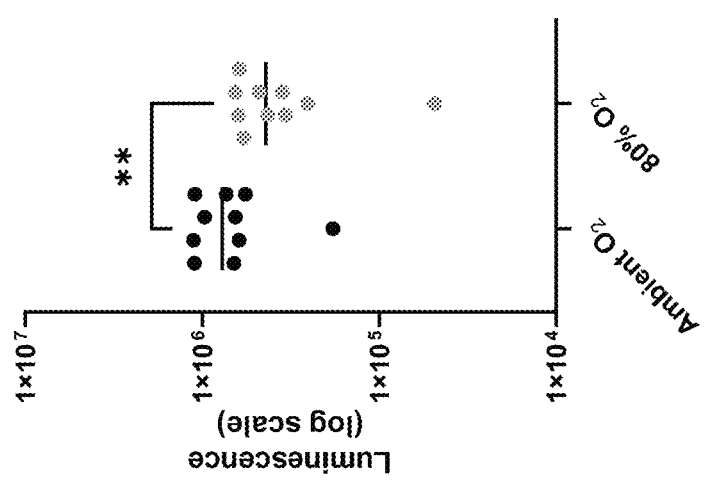
FIGS. 19A and 19B show the effect of optimum oxygen concentration during culture of tissue fragments.
Figure 19B:
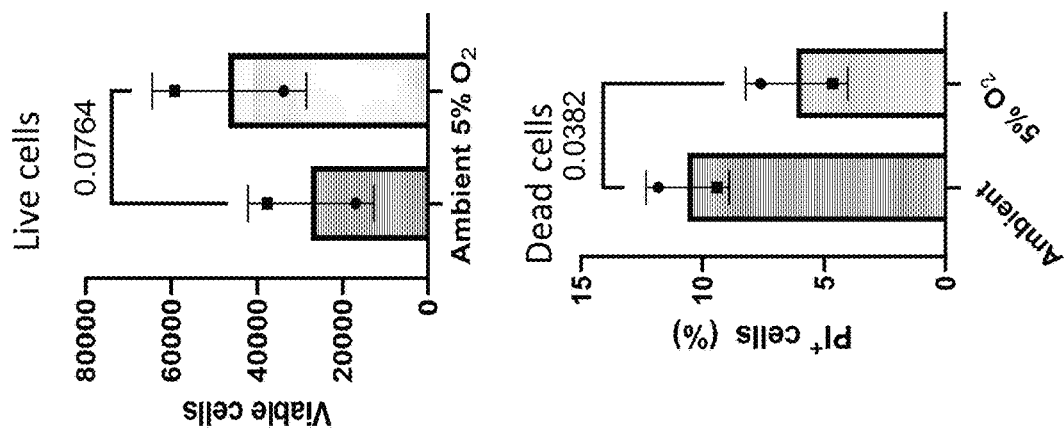
Figure 20:
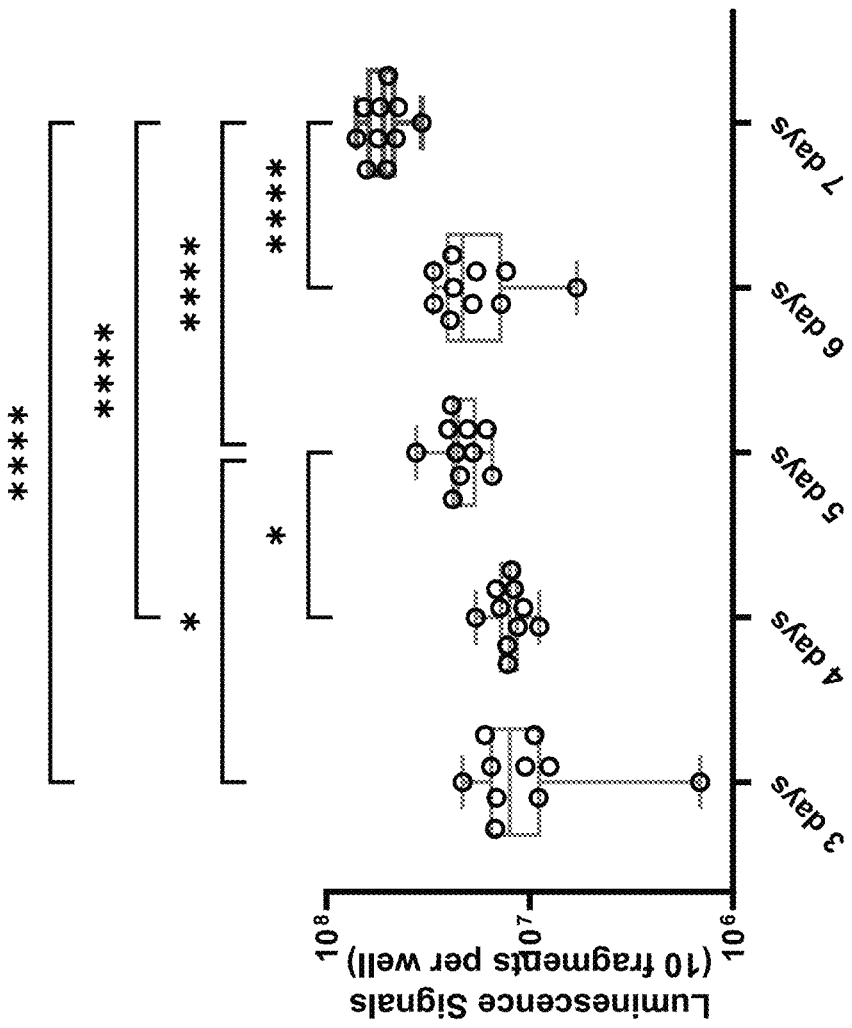
FIG. 20 shows the viability of tissue fragments (expressed as luminescence signal on the Y-axis) maintained in culture for 7 days. Each data point represents signal from one well containing 10 fragments each.
Figure 21A:
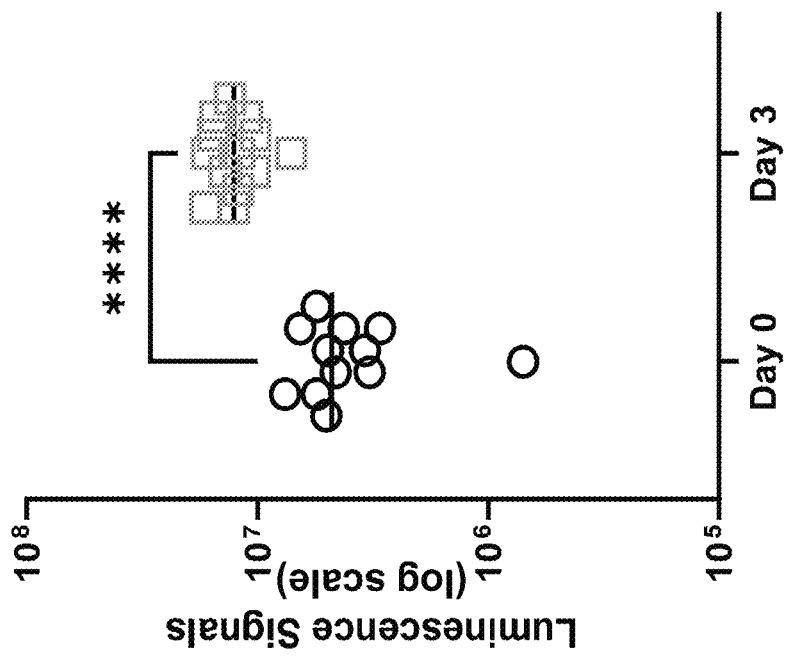
FIG. 21A-C show cell recovery at Day 3 of culture (compared to Day 0).
Figure 21C:
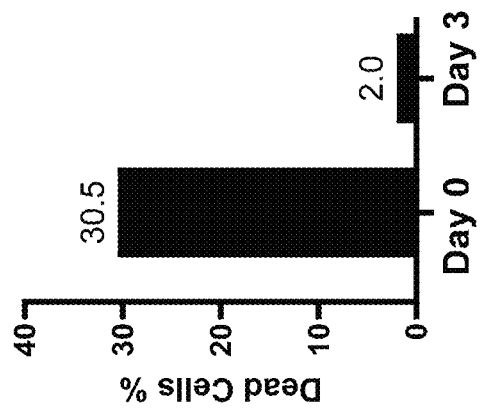
Figure 21B:
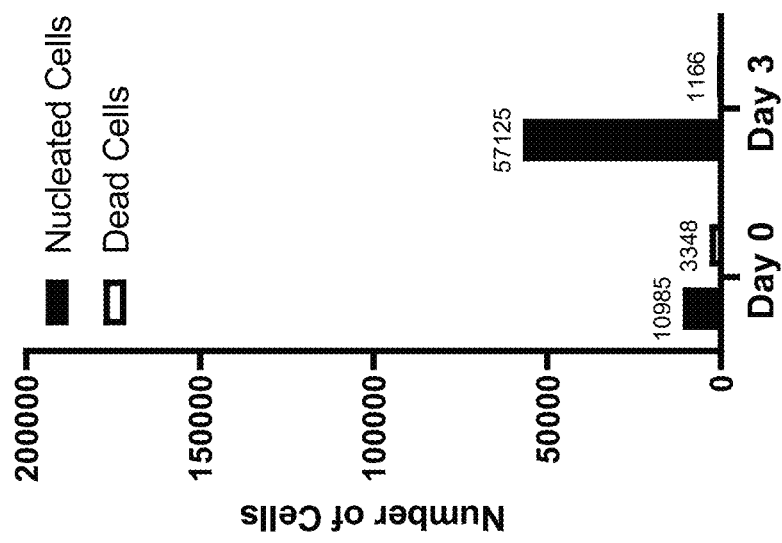

In some embodiments, for certain tissue types, the cell viability is reduced under conditions of hyperoxia (such as shown in FIG. 19A). In some embodiments, the tissue fragments are cultured under conditions of hypoxia (such as at oxygen concentrations less than 20%, such as 15% or 10% or 5%). In some embodiments, cell viability was increased and dead cell numbers were reduced in tissue fragments cultured under conditions of hypoxia (e.g., 5% oxygen) compared to tissue fragments cultured in ambient oxygen (FIG. 19B). In some embodiments, the tissue fragments are perfusion cultured, wherein the culture media is perfused continuously or intermittently. In some embodiments, the tissue fragments are cultured under condition where the culture medium is changed at pre-defined intervals (e.g., every 12 hours, 24 hours and the like) or at intervals depending upon the status of the tissue fragments and/or the culture medium. In some embodiments, the tissue fragments are cultured under non-perfused conditions. In some embodiments, the tissue fragments are cultured utilizing inserts. Inserts are support structures within chambers of the culture platform on which the tissue fragments are positioned during culture. Positioning the tissue fragments on the inserts allow culture medium to perfuse around the tissue fragments, thereby enhancing oxygen and nutrient availability to the tissue fragments. A person of ordinary skill in the art can envisage inserts of various size, material and property, depending on the size, type and/or other properties of the tissue fragments. In some embodiments, the inserts comprise stainless steel mesh structures. In some embodiments, the inserts are detachably placed within the chambers of the culture platform. In some embodiments, the tissue fragments are cultured on a culture platform made of an oxygen-permeable material. In some embodiments, the culture platform comprises an oxygen-permeable base. In some embodiments, the tissue fragments are cultured under stationary condition of the culture platform. In some embodiments, the tissue fragments are cultured under dynamic condition of the culture platform, wherein the culture platform is subjected to motion such as rocking motion, orbital motion and the like. One or more methods described in the embodiments described herein helped to maintain the tissue fragments in culture for more than 3 days (such as for more than 5 days) without any loss in cell viability (FIG. 20). In some embodiments, the tissue fragments were maintained in culture for up to 7 days without any loss in cell viability. In some embodiments, cell viability and cell number improved after 1 day in culture. In some embodiments, cell viability and cell number on day 3 of culture were significantly higher than that on day 0, and the percentage of dead cells was also less at day 3 compared to day 0 (FIG. 21A-C). In some embodiments, the timing of drug addition depends on the drug class. In some embodiments, a drug or an agent is added to a tissue fragment after the tissue fragment is cultured for a duration of time (such as for 5 hours, 10 hours, 12 hours or 24 hours and the like). In some embodiments, particularly where the drug or the agent is a cytotoxic chemotherapeutic, this time period allows the tissue fragments to recover (such as from one or more processes of cutting, sorting etc.), as seen from increase in cell viability and live cell numbers. In some embodiments, for an immunomodulator drug or agent, the additional recovery time is not required and the drug or the agent is added on day 0 of culture.

In some embodiments, the status of the tissue fragments and/or the culture medium is monitored using a sensor. In some embodiments, the culture platform comprises one or more sensors. In some embodiments, one or more sensors monitor one or more characteristics of the culture medium, non-limiting examples of which include dissolved oxygen status, pH, lactate concentration, glucose concentration and the like. In some embodiments, based on an input from one or more sensors, a culture condition is optimized or varied. A culture condition includes one or more of oxygen concentration, timing of culture medium change, perfusion rate, motion of the culture platform or the like.

In some embodiments, the culture platform is housed within an incubator during culture of the tissue fragments. In some embodiments, the incubator is configured to maintain the tissue fragments at a temperature, humidity and oxygen concentration that is suitable for culture. In some embodiments, the incubator is configured to maintain the tissue fragments at a temperature of about 37° C., with about 5% $CO_2$ and under humidified conditions. In some embodiments, the incubator is configured to maintain the tissue fragments under suitable oxygen concentration, for example the incubator is configured to maintain the tissue fragments under optimal and controlled oxygen concentration equal to or greater than 5%, 10% or 20% (such as 5%, 10%, 20%, or 30% or 40% or 50% or 60% or 70% or 80% and the like).

In some embodiments, the step of performing an ex vivo measurement on the tissue fragments comprises measuring an ex vivo tissue parameter. In some embodiments, the step of performing an ex vivo measurement on the tissue fragments comprises imaging the tissue fragments for measuring an ex vivo tissue parameter. In some embodiments, the ex vivo tissue parameter is a cell parameter. In some embodiments, the ex vivo tissue parameter is an extracellular parameter. In some embodiments, measuring an ex vivo tissue parameter comprises measuring a cell parameter. In some embodiments, measuring an ex vivo tissue parameter comprises measuring a cell parameter and an extracellular parameter. In some embodiments, the ex vivo tissue parameter is measured once or at multiple timepoints after drug or other agent addition. In some embodiments, the ex vivo tissue parameter is measured while the tissue fragments are in culture, such as in the presence of a drug or an agent. In some embodiments, the ex vivo tissue parameter is measured at various timepoints while the tissue fragments are in culture. In some embodiments, the ex vivo tissue parameter is measured once before the termination of culture. In some embodiments, the ex vivo tissue parameter is measured after the termination of culture. In some embodiments, one or more cell parameters are measured of tumor cells in the tissue fragment. In some embodiments, one or more cell parameters are measured of tumor cells and non-tumor cells (e.g., immune cells, stromal cells) in the tissue fragment. In some embodiments, the step of cell parameter measurement comprises imaging individual cells within each tissue fragment. In some embodiments, the step of imaging comprises imaging with one or multiple imaging modalities. In some embodiments, the step of imaging comprises imaging with a fluorescence imaging modality. In some embodiments, measuring a cell parameter comprises measuring one or more of fluorescence intensity, fluorescence lifetime or fluorescent polarization from endogenous fluorophores, exogenous fluorophores or both. In some embodiments, the measurement of cell parameter comprises imaging the intrinsic fluorescence of the cells (such as the fluorescence from endogenous fluorophores). In some embodiments, intrinsic cellular fluorescence comprises cellular autofluorescence that arises due to one or more endogenous fluorophores such as NADH (reduced form of nicotinamide adenine dinucleotide), NADPH (reduced form of nicotinamide adenine dinucleotide phosphate), flavins and flavin derivatives (such as flavin adenine dinucleotide (FAD)), aromatic amino acids such as tryptophan, tyrosine and the like. In some embodiments, cell parameter is a cellular metabolic activity obtained from a ratio of the fluorescence intensity of NAD(P)H to that of FAD. In some embodiments, the cell parameter is a measure of the fluorescent lifetime of NAD(P)H. In some embodiments the cell parameter is a measure of the fluorescent lifetime of FAD. In some embodiments, an extracellular parameter is a measure of the intensity and/or polarization of scattered light generated by collagen. In some embodiments, the step of cell parameter measurement comprises imaging fluorescently labelled cells. In some embodiments, cell parameter measurement is performed by labelling cells with live/dead cell labels. In some embodiments, cell parameter measurement is performed by labelling cells with morphological labels, for example one or more labels to stain the nucleus, cytoskeleton, mitochondria, endoplasmic reticulum, plasma membrane and the like. In some embodiments, cell parameter measurement is performed by labelling cells with a functional or a metabolic label. In some embodiments, measuring at least one ex vivo tissue parameter comprises measuring one or more cell parameter and optionally one or more extracellular parameters.

Figure 23B:
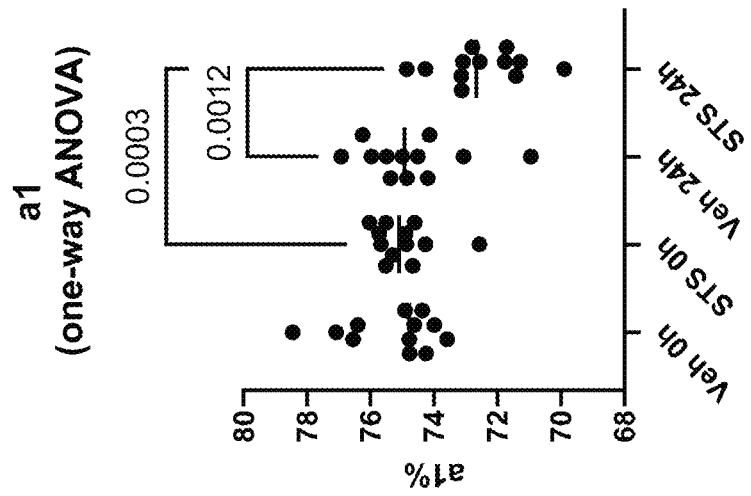
FIG. 23B shows the fluorescence intensity of the short lifetime component of NAD(P)H (measured as the amplitude (a1) of the short lifetime component) in tissue fragments treated with vehicle (Veh) and staurosporine (STS), at 0 and 24 hours respectively.
Figure 23A:
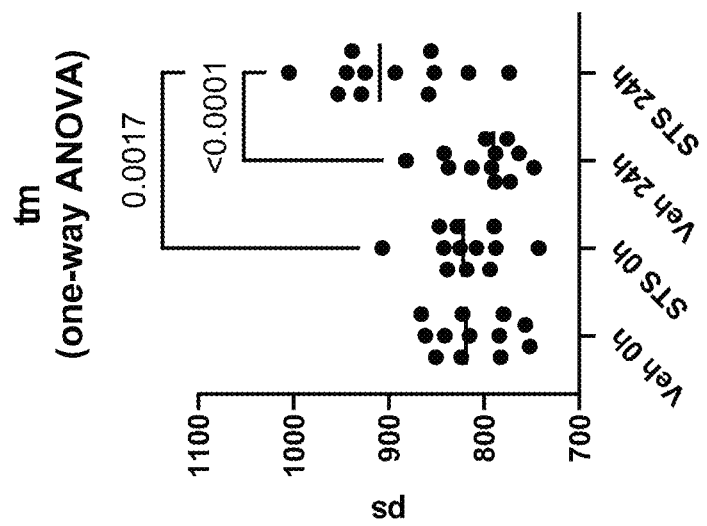
FIG. 23A shows the mean fluorescence lifetime (tm) in picoseconds (ps) of NAD(P)H in tissue fragments treated with vehicle (Veh) and staurosporine (STS), at 0 and 24 hours respectively.
Figures 23C, 23D:
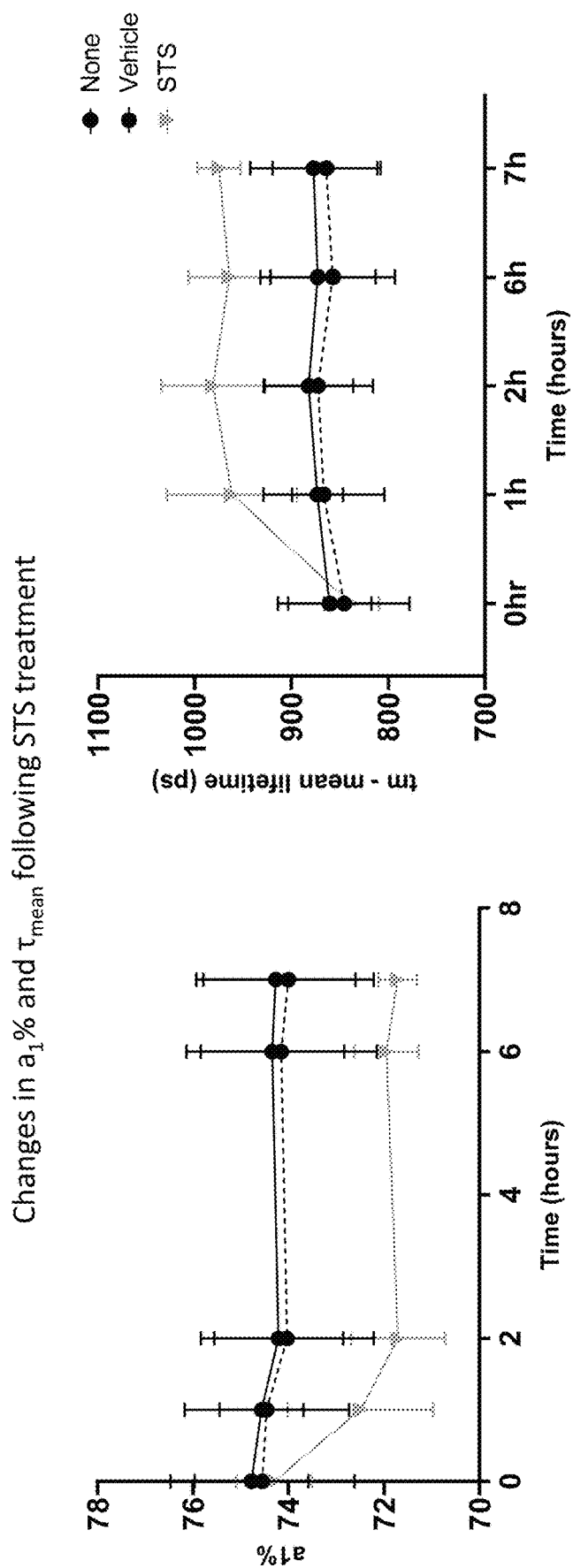
FIG. 23C shows the changes in the amplitude of the short lifetime component (a1 %) of NAD(P)H in tissue fragments, under conditions of no treatment (none), vehicle treatment (Veh), and staurosporine treatment (STS), from 0 to 7 hours.
FIG. 23D shows the changes in mean fluorescence lifetime (in ps) of NAD(P)H in tissue fragments, under conditions of no treatment (none), vehicle treatment (Veh), and staurosporine treatment (STS), from 0 to 7 hours.

In some embodiments, the step of measuring the ex vivo tissue parameter of the tissue fragments comprises measuring one or more of, the fluorescence emission intensity and the fluorescence lifetime of NAD(P)H and/or FAD. In some embodiments, the step of measuring the ex vivo tissue parameter of the tissue fragments comprises measuring the fluorescence emission intensity of one or more NAD(P)H populations distinguished by fluorescence lifetimes. In some embodiments, one NAD(P)H population is characterized by a shorter duration NAD(P)H fluorescence lifetime component whereas other NAD(P)H populations are characterized by longer duration NAD(P)H fluorescence lifetime components. In some embodiments, the measurement is a longitudinal measurement performed at multiple time points after the addition of the drug or the agent. In some embodiments, there is a decrease in the fluorescence emission intensity of the short lifetime component of NAD(P)H after drug addition (FIGS. 23B and 23C). In some embodiments, there is an increase in mean lifetime after drug addition (FIGS. 23A and 23D).

In some embodiments, the step of measuring the ex vivo tissue parameter comprises measuring one or more factors including but not limited to, interleukin-2 (Il-2), interleukin-4 (Il-4), interleukin-6 (Il-6), interleukin-10 (Il-10), interleukin-17A (Il-17A), Tumor necrosis factor alpha (TNF-α), soluble Fas (sFas), soluble Fas ligand (sFasL), interferon gamma (IFN-γ), granzyme A, granzyme B, perforin, granulysin, interleukin-8 (Il-8), iterferon gamma-induced protein 10 (IP-10), eotaxin, thymus and activation-regulated chemokine (TARC), monocyte chemoattractant protein-1 (MCP-1), RANTES, macrophage inflammatory protein (MIP)-1α, monokine induced by interferon-γ (MIG), epithelial-neutrophil activating peptide (ENA-78), MIP-3α, GROα, I-TAC, or MIP-1b. In some embodiments, the drug or the agent is an immunotherapeutic or immune modulating drug or agent.

In some embodiments, the step of determining the effect of the drug or the agent on the tissue fragments comprises performing one or more ex vivo measurements on the tissue fragments. The upfront determination of tumor content and/or cell viability aids or facilitates ex vivo drug response assessment in one or more ways. In some embodiments, data from the one or more ex vivo measurements (or the ex vivo tissue parameter data) is analyzed based on the estimated tumor content and/or the estimated cell viability. In some embodiments, the data from one or more ex vivo measurements performed on the tissue fragments is analysed if the estimated tumor content is equal to or greater than a tumor content cut-off and/or if the estimated cell viability is equal to or greater than a cell viability cut-off. For example, the data from one or more ex vivo measurements performed on a tissue fragment is analyzed if the tissue fragment is estimated to have tumor content and/or cell viability equal to or greater than the respective cut-off values. In other examples, when multiple tissue fragments are dispensed in a chamber, the data from the ex vivo measurements (performed on the tissue fragments in the chamber) is analyzed if a minimum number of tissue fragments within that chamber is estimated to have tumor content and/or cell viability equal to or greater than the respective cut-off values. In some embodiments, analyzing the data from the one or more ex vivo measurements comprises normalizing the data with respect to the estimated tumor content and/or the estimated cell viability. In some embodiments, the data from the one or more ex vivo measurements is normalized with respect to one or more of the estimated tumor content or cell viability.

In some embodiments, the step of determining the effect of the drug or the agent on the tissue fragments comprises inputting the ex vivo tissue parameter data into a predictive algorithm. In some embodiments, the step of determining the effect of the drug or the agent on the tissue fragments comprises comparing the ex vivo tissue parameter data with a control data. In some embodiments, the control data is a reference tissue parameter data, wherein the reference tissue parameter data is obtained from an ex vivo tissue parameter measurement performed on a reference tissue fragment, wherein the reference tissue fragment is not treated with the drug or the agent. In some embodiments, the control data is an ex vivo tissue parameter data obtained from an ex vivo tissue parameter measurement performed on tissue fragments at a timepoint t0, wherein t0 is a timepoint at the time of drug or other agent addition, a timepoint immediately before drug or the agent addition or a timepoint immediately after the drug or the agent addition. In some embodiments, the ex vivo tissue parameter data is obtained from an ex vivo tissue parameter measurement performed on the tissue fragments at one or more timepoints (tn) after the addition of the drug or the agent (such as at 12 hours (t12), 24 hours (t24), 36 hours (t36), 48 hours (t48), 72 hours (t72), 120 hours (t120) and so on). In some embodiments, the step of determining the effect of the drug or other agent on the tissue fragments comprises comparing the ex vivo tissue parameter data obtained at one or more timepoints tn, to the ex vivo tissue parameter data obtained at time t0. In some embodiments, the method further comprises estimating the tumor content of the tissue fragment at one or more timepoints (tn) after the addition of the drug or other agent. In some embodiments, the method of determining ex vivo drug or other agent response further comprises, normalizing the ex vivo tissue parameter data obtained from a tissue fragment at each timepoint tn to the estimated tumor content of the same tissue fragment. In some embodiments, the step of ex vivo tissue parameter measurement comprises imaging live tissue fragments. In some embodiments, the step of ex vivo tissue parameter measurement comprises imaging live tissue fragments without the addition of an exogenous agent.

Some embodiments relate to a method of predicting the clinical responsiveness of a subject to a drug or an agent, the method comprising: a) providing tissue fragments, wherein the tissue fragments are generated from a tissue which is obtained from a subject; b) imaging the tissue fragments to estimate one or more of tumor content or cell viability of the tissue fragments; c) adding a drug or an agent to the tissue fragments; d) performing one or more ex vivo measurements on the tissue fragments (that are treated with the drug or the agent); and e) predicting the clinical responsiveness of the subject to the drug or the agent based on data from the one or more ex vivo measurements performed on the tissue fragments. In some embodiments, the drug or the agent is added to the tissue fragments based on one or more of the estimated tumor content or cell viability. In some embodiments, the data from the one or more ex vivo measurements is analysed based on one or more of the estimated tumor content or cell viability.

The tissue fragments are live tissue fragments, and the step of estimating the tumor content or estimating the cell viability is performed on live tissue fragments. In some embodiments, the tissue fragments are imaged without the addition of an exogenous label. In some embodiments, the tissue fragments are generated by cutting the tissue with a cutting device. In some embodiments, the step of providing tissue fragments comprises sorting the tissue fragments based on an optical characteristic of the tissue fragments and dispensing the sorted tissue fragments into the chambers of a culture platform. The tissue fragments that are dispensed into the chambers of the culture platform are free of one or more of residual gel matrix, residual sacrificial casing, multiplets, tissue debris, disintegrated tissue fragments or tissue fragments not meeting a size criterion. In some embodiments, the tissue fragments that are dispensed into the chambers of the culture platform meet one or more criteria selected from size, integrity, absence of multiplets, and the absence of exogenous agents. In some embodiments, the tissue fragments are preserved at a temperature between about 0° C. and about −200° C. (preferably between about −120° C. and about −200° C.), and the step of providing tissue fragments further comprises thawing the tissue fragments prior to sorting. In some embodiments, the tissue fragments are cryopreserved at a temperature between about 0° C. and about −200° C. after being generated (such as by cutting) from the tissue.

In some embodiments, the step of imaging comprises imaging live tissue fragments using one or more of fluorescence emission, fluorescence lifetime, fluorescence lifetime composition or second harmonic generation, of one or more endogenous labels. In some embodiments, the method comprises, imaging the live tissue fragments without the addition of an exogenous label to obtain label-free, live tissue images and wherein the estimation of tumor content comprises a histologic assessment of the label-free, live tissue images, wherein the step of histologic assessment comprises identifying regions of tumor cells and normal cells. In some embodiments, the histologic assessment is performed with the help of a machine learning algorithm. In some embodiments (such as shown in FIG. 16 and described earlier in the specification) the machine learning algorithm is trained on a plurality of training tissue images comprising, label-free, live tissue images and matched, annotated, stained tissue images.

In some embodiments, a drug or an agent is added to a tissue fragment if the tissue or the tissue fragment is estimated to have a tumor content greater than a cut-off (such as tumor content cut-off). In some embodiments, the step of estimation of tumor content comprises quantifying the spatial distribution of an endogenous fluorophore (such as NAD(P)H) using one or more entropy parameters (FIG. 17C). In some embodiments, the step of estimation of tumor content comprises quantifying the mean lifetime of NAD(P)H and/or the mean amplitude of one or more populations of NAD(P)H distinguished by fluorescence lifetimes (FIG. 17A-B). In some embodiments, the populations of NAD(P)H are identified by a short fluorescence lifetime component (with lifetime between about 0.2 and 1 nanoseconds (ns)) and a long fluorescence lifetime component (with lifetime between about 1 and 5 ns). In some embodiments, the population of NAD(P)H is the short fluorescence lifetime component of NAD(P)H). In some embodiments, the step of imaging comprises second harmonic generation (SHG) imaging of a SHG structure such as collagen fibers, and wherein the step of estimation of tumor content comprises determination of a fiber parameter of the SHG structure (such as fiber width, straightness or average length) (FIG. 17D).

The tumor content cut-off can be a pre-defined cut-off or a user-defined cut-off. As described earlier, the tumor content cut-off can be a number or percentage of tumor cells or be based on a surrogate parameter of tumor content (such as an entropy parameter, ECM fiber parameter etc.). In some embodiments, the cut-off is at least 1% tumor cells within the tissue or the tissue fragment. In some embodiments, a drug or other agent is added to a tissue fragment if the estimated percentage of tumor cells within the tissue fragment is at least 1%.

In some embodiments, the method comprises performing a viability assessment of the tissue fragments to estimate the cell viability. In some embodiments, the step of performing the viability assessment comprises imaging the tissue fragments for determining the fluorescence emission intensity, the fluorescence lifetime and/or the fluorescence lifetime composition of an endogenous fluorophore, wherein the endogenous fluorophore is indicative of live cells. In some embodiments, the drug or the agent is added if the estimated cell viability is equal to or greater than a cut-off (cell viability cut-off). In some embodiments, the cell viability is determined from the fluorescence emission intensity of the endogenous fluorophore. In some embodiments, the drug or the agent is added if the fluorescence intensity of the endogenous fluorophore (such as NAD(P)H) is greater than an intensity threshold, wherein the intensity threshold is trained on a training set of tissue fragments labelled with an exogenous label (such as PI) that stains dead cells, wherein the intensity threshold of the endogenous fluorophore is trained on the intensity of the exogenous label. In some embodiments, the cell viability cut-off is provided by the intensity threshold of the endogenous fluorophore.

In some embodiments, the step of performing an ex vivo measurement on the tissue fragments comprises measuring an ex vivo tissue parameter. In some embodiments, the ex vivo tissue parameter is measured by imaging the tissue fragments. The step of ex vivo tissue parameter measurement of the tissue fragments is performed after treating the tissue fragments with the drug or other agent. The step of ex vivo measurement can be performed once or can be performed at multiple timepoints after drug or other agent treatment. In some embodiments, the step of measuring an ex vivo tissue parameter comprises measuring a cell parameter. In some embodiments, the step of measuring an ex vivo tissue parameter comprises measuring a plurality of cell parameters. In some embodiments, the step of measuring an ex vivo tissue parameter comprises measuring a cell parameter and an extracellular parameter. In some embodiments, the ex vivo tissue parameter measurement is performed on live tissue fragments. In some embodiments, ex vivo tissue parameter measurement is performed without the addition of an exogenous label. In some embodiments, the data from the one or more ex vivo measurements is analysed (for predicting the clinical responsiveness) only if one or more of the estimated tumor content or cell viability is equal to or greater than the respective cut-offs. In some embodiments, the data from the one or more ex vivo measurements is normalized with respect to one or more of the estimated tumor content or cell viability.

In some embodiments, the step of performing an ex vivo tissue measurement comprises imaging the tissue fragments to measure one or more of, the fluorescence emission intensity, the fluorescence lifetime of NAD(P)H or the fluorescence lifetime composition of NAD(P)H. In some embodiments, the step of performing an ex vivo measurement on the tissue fragments further comprises measuring factors including but not limited to Il-2, Il-4, Il-6, Il-10, Il-17A, TNF-α, sFas, sFasL, IFN-g, granzyme A, granzyme B, perforin, granulysin, Il-8, IP-10, eotaxin, TARC, MCP-1, RANTES, MIP-1α, MIG, ENA-78, MIP-3α, GROα, I-TAC, or MIP-1b.

In some embodiments, the step of predicting the clinical responsiveness based on the ex vivo measurement performed on the tissue fragments comprises obtaining a data from the ex vivo measurement (ex vivo tissue parameter data) and inputting the ex vivo tissue parameter data into a predictive algorithm.

In some embodiments, the step of predicting a clinical responsiveness based on the ex vivo measurement comprises obtaining an ex vivo tissue parameter data from the ex vivo measurement and comparing the ex vivo tissue parameter data with a control data. In some embodiments, the control data is a reference tissue parameter data, wherein the reference tissue parameter data is obtained from an ex vivo measurement performed on a reference tissue fragment, wherein the reference tissue fragment is not treated with the drug or other agent. In some embodiments, the reference tissue fragment is generated from the tissue obtained from the subject. In some embodiments, the control data is an ex vivo tissue parameter data obtained from an ex vivo measurement performed on tissue fragments at a timepoint (t0), wherein t0 is a timepoint at the time of drug or other agent addition, a timepoint immediately before drug or other agent addition or a timepoint immediately after drug or other agent addition. In some embodiments, the ex vivo tissue parameter data can be obtained from an ex vivo measurement performed on the tissue fragments at one or more time points (tn) after the addition of the drug or other agent (such as at 12 hours (t12), 24 hours (t24), 36 hours (t36), 48 hours (t48), 72 hours (t72), 120 hours (t120) and so on). In some embodiments, the step of predicting the clinical responsiveness comprises comparing the ex vivo tissue parameter data obtained from an ex vivo tissue parameter measurement performed on a tissue fragment at timepoint tn, to the ex vivo tissue parameter data obtained from an ex vivo tissue parameter measurement performed on the same tissue fragment at to.

According to some embodiments, a predictive algorithm is an algorithm that uses an ex vivo tissue parameter data as input and generates an output indicative of a predicted clinical responsiveness. In some embodiments, the output is a numerical value, and the predicted clinical responsiveness is based on the numerical value. In some embodiments, a numerical scale extends between complete response on one end and non-response on the other. The predicted clinical responsiveness can be that of predicted clinical response or predicted clinical non-response based on the relative position of the numerical value on the numerical scale. In some embodiments, the numerical value is compared to a cut-off. In some embodiments, the predicted clinical responsiveness is that of predicted clinical response if the numerical value is above the cut-off and that of predicted clinical non-response if the numerical value is below the cut-off, or vice versa. In some embodiments, the predicted clinical responsiveness is a binary prediction of either predicted clinical response or predicted clinical non-response. In some embodiments, the predicted clinical responsiveness can be a predicted complete response, a predicted partial response, a predicted stable disease or a predicted progressive disease. In some embodiments, the predicted clinical responsiveness is a continuous scale between a complete clinical response and a progressive disease.

Some embodiments relate to a computer-implemented method for generating a predictive algorithm of responsiveness to a drug or other agent, the method comprising: a) obtaining a set of training tissue parameter data generated from one or more ex vivo tissue parameter measurements performed on a set of tissue fragments treated ex vivo with a drug or an agent, wherein the set of tissue fragments are generated from tissues obtained from a training cohort of subjects; b) obtaining a set of training clinical parameter data generated from one or more clinical parameter measurements performed on the training cohort of subjects treated with the drug or the agent; and c) generating a predictive algorithm of responsiveness to the drug or the agent using the set of training tissue parameter data and the set of training clinical parameter data. In some embodiments, the method further comprises validating the predictive algorithm of responsiveness to the drug or other agent using a validation tissue parameter data and a validation clinical parameter data.

The validation tissue parameter data is generated from one or more ex vivo tissue parameter measurements performed on a tissue fragment treated ex vivo with a drug or the agent, wherein the tissue fragment is generated from a tissue obtained from a subject in a validation cohort. The validation clinical parameter data is generated from one or more clinical parameter measurements performed on said subject in the validation cohort, wherein the subject is treated with the drug or the agent. In some embodiments, the step of validating the predictive algorithm of responsiveness to the drug or the agent comprises, a) inputting the validation tissue parameter data into the predictive algorithm of responsiveness to the drug or the agent to generate a predicted clinical responsiveness for the subject in the validation cohort; and b) comparing the predicted clinical responsiveness to an actual clinical responsiveness, wherein the actual clinical responsiveness is determined from the validation clinical parameter data. In some embodiments, the step of validating the predictive algorithm of drug response comprises performing steps a) and b) for all the subjects in the validation cohort.

Some embodiments relate to a method of treatment of a subject, the method comprising: receiving a predicted clinical responsiveness of a subject to a drug or an agent and treating the subject based on the predicted clinical responsiveness, wherein the steps to generate a predicted clinical responsiveness of a subject to a drug or an agent comprises: a) generating tissue fragments from a tissue obtained from the subject; b) sorting the tissue fragments based on an optical characteristic of the tissue fragments; c) treating the sorted tissue fragments ex-vivo with a drug or an agent based on one or more of an estimated tumor content or an estimated cell viability of the tissue or the tissue fragments; d) obtaining an ex vivo tissue parameter data from an ex vivo tissue parameter measurement performed on the tissue fragments treated with the drug or the agent; and e) generating a predicted clinical responsiveness of the subject to the drug or the agent based on the ex vivo tissue parameter data.

The step of treating a subject based on a predicted clinical responsiveness of the subject to a drug or other agent comprises treating the subject with the drug or the agent if the subject is predicted to respond to the drug or the agent or treating the subject with an alternative treatment if the subject is predicted not to respond to the drug or the agent. In some embodiments, the method comprises receiving the predicted clinical responsiveness of the subject to a plurality of drugs or agents and treating the subject with the drug or other agent to which the subject is predicted to respond or the drug or other agent to which the predicted clinical responsiveness is the highest.

In some embodiments, the step of treating the tissue fragments ex vivo with a drug or an agent based on the estimated tumor content comprises adding a drug or an agent to the tissue fragments, if the estimated tumor content of the tissue or the tissue fragment is equal to or greater than a cut-off. In some embodiments, the step of treating the tissue fragments ex vivo with a drug or an agent based on the estimated cell viability comprises adding a drug or an agent to the tissue fragments, if the estimated cell viability of the tissue or the tissue fragments is equal to or greater than a cut-off. In some embodiments, the tumor content and cell viability are estimated by imaging the tissue fragments. In some embodiments, the step of imaging comprises imaging live tissue fragments (such as without fixing the tissue fragments) using one or more of fluorescence emission imaging, fluorescence lifetime imaging, or second harmonic imaging, of one or more endogenous labels.

In some embodiments, the method comprises, imaging the live tissue fragments without the addition of an exogenous label to obtain label-free, live tissue images and wherein the estimation of tumor content comprises a histologic assessment of the label-free, live tissue image, wherein the step of histologic assessment comprises identifying regions of tumor cells and normal cells. In some embodiments, the histologic assessment is performed with the help of a machine learning algorithm. In some embodiments (such as shown in FIG. 16 and described earlier in the specification) the machine learning algorithm is trained on a plurality of training tissue images comprising, label-free, live tissue images and matched, annotated, stained tissue images.

In some embodiments, the step of estimation of tumor content comprises quantifying the spatial distribution of an endogenous fluorophore (such as NAD(P)H) using one or more entropy parameters. In some embodiments, the step of estimation of tumor content comprises quantifying the mean lifetime of NAD(P)H and/or the mean amplitude of the short lifetime component of NAD(P)H. In some embodiments, the step of imaging comprises SHG imaging of SHG structures, and wherein the step of estimation of tumor content comprises quantifying a fiber parameter of the SHG structures (such as fiber width, length or straightness).

In some embodiments, the cell viability is determined from the fluorescence emission intensity of the endogenous fluorophore. In some embodiments, the drug or the agent is added if the fluorescence intensity of the endogenous fluorophore (such as NAD(P)H) is greater than an intensity threshold, wherein the intensity threshold is trained on a training set of tissue fragments labelled with an exogenous label (such as PI) that stains dead cells, wherein the intensity threshold of the endogenous fluorophore is trained on the intensity of the exogenous label. In some embodiments, the cell viability cut-off is provided by the intensity threshold of the endogenous fluorophore.

In some embodiments, the ex vivo tissue parameter measurement is performed on a live tissue fragment. The ex vivo tissue parameter measurement is performed on the tissue fragments after the step of addition of the drug or the agent. The ex vivo tissue parameter measurement on the tissue fragment can be performed once or multiple times after drug treatment (such as at any timepoint to after drug or other agent addition). In some embodiments, the step of generating a predicted clinical responsiveness comprises inputting the ex vivo tissue parameter data into a predictive algorithm. In some embodiments, the step of generating a predicted clinical responsiveness comprises comparing the ex vivo tissue parameter data with a control data. In some embodiments, the control data is a reference tissue parameter data, wherein the reference tissue parameter data is obtained from a reference tissue fragment, wherein the reference tissue fragment is not treated with the drug or other agent. In some embodiments, the reference tissue fragment is generated from the tissue obtained from the subject. In some embodiments, the control data is an ex vivo tissue parameter data obtained from the tissue fragment at a timepoint t0, wherein t0 is a timepoint at the time of drug or other agent addition, a timepoint immediately before drug or other agent addition or a timepoint immediately after the addition of the drug or other agent.

Some embodiments relate to a system comprising: a tissue cutting device configured to cut a tissue into tissue fragments; a sorter configured to sort the tissue fragments based on an optical characteristic and dispense the tissue fragments into chambers of a culture platform; an imaging system configured to image the tissue fragments; and an incubator configured to house the culture platform. In some embodiments, the system is a single, closed system. In some embodiments, the system comprises two closed subsystems comprising a) a first closed subsystem comprising: i) a tissue cutting device configured to cut a tissue into tissue fragments and ii) a sorter configured to sort the tissue fragments based on an optical characteristic and dispense the tissue fragments into chambers of a culture platform; and b) a second closed subsystem comprising: i) an imaging system configured to image the tissue fragments; and ii) an incubator configured to house the culture platform.

In some embodiments, the second closed subsystem further comprises a liquid handling system configured to add measured quantities of a drug to the tissue fragments. In some embodiments, the first and second subsystems are operatively connected. In some embodiments, the first subsystem is configured to be maintained at a temperature of 4° C. In some embodiments, the imaging system comprises one or more imaging modalities.

In some embodiments, the system comprises three closed subsystems comprising a) a first closed subsystem comprising of a tissue cutting device configured to cut a tissue into tissue fragments; b) a second closed subsystem comprising of a sorter configured to sort the tissue fragments based on an optical characteristic and dispense the tissue fragments into chambers of a culture platform; and c) a third closed subsystem comprising of i) an imaging system configured to image the tissue fragments; and ii) an incubator configured to house the culture platform.

EXAMPLES

The following examples are intended only to illustrate methods and embodiments in accordance with the invention, and as such should not be construed as imposing limitations upon the claims.

Example 1: Fragmentation Procedure

Excised tumor tissue samples were obtained from the vivarium and temporarily stored in Krebs-Henseleit Buffer supplemented with 10 mM HEPES and 1% penicillin/streptomycin stock solution (Pen/Strep), pH=7.40 (KHB) on ice. To cut the tissue into 100 µm×300 µm×300 µm fragments, the Compresstome® (Precisionary Instruments, USA) was used for cutting in the first dimension (100 µm) and McIlwain tissue chopper (Ted Pella, Inc. CA, USA) for the second and third dimensions (300 µm). To cut in the first dimension, the Compresstome® was prepared to cut 100 µm-thick fragments by mounting tissue samples onto the specimen tube using ethyl cyanoacrylate glue (Krazy Glue®) and embedding them in 3% agarose in KHB. The embedded tissue was cut into 100 µm sections (speed setting 1; frequency setting 7) in cold KHB. Following cutting, agarose was separated from the tissue fragments (cut in the first dimension) using forceps and the fragments were transferred into ice-cold KHB for temporary storage before cutting on the McIlwain tissue chopper.

After leveling the blade on the McIlwain tissue chopper and setting to 300 µm thickness, the tissue fragments (cut in the first dimension) were cut into fragments in the second and third dimensions. The 100 µm-thick fragments were laid flat on a polymethylmethacrylate (PMMA) disc, and excess fluid was removed by pipetting to prevent movement of tissue. After the first series of cuts, the disc was rotated by 90° and the cutting procedure was repeated. After cutting, the fragments were transferred to a dish using a pipette and ice cold KHB. Gentle pipetting was used to separate the fragments. Then the fragments were filtered through a 750 µm filter, followed by a 40 µm filter (Pluriselect, USA). Fragments of interest passed through the 750 µm filter and were retained on the 40 µm filter. Fragments were rinsed off the inverted 40 µm filter with ice cold KHB. After washing, the fragments of interest were temporarily stored in ice cold KHB in a 50 mL conical tube.

Example 2: Comparison of Cell Viability in Tumor Fragments Under Hypothermal (Cold) Preservation Condition and Cryopreservation Condition with Cell Viability in Fresh Tissue Fragments (without Storage/Preservation)

To determine the feasibility of transporting tissue fragments from one site (such as a source site, e.g., hospital) to another (such as a destination site, e.g., laboratory where the fragments are processed) viability was assayed after simulation of different transportation methods. A subcutaneous EMT6 mouse breast cancer tumor was harvested and cut into 100×300×300 µm fragments. First, the tumor was embedded in 3.5% agarose at 37° C. (A0576-100G; Sigma Aldrich), in the sample tube of Compresstome (VF-310-0Z; Precisionary Instruments, USA). Then the tumor samples were fragmented on the Compresstome under sterile conditions with oxygenated L15 medium on ice. The Compresstome created 100 µm thick tumor sections with a ring of solidified agarose. The agarose was gently removed using two sets of forceps. The tissue sections were further cut using a McIlwain tissue chopper (Ted Pella, Inc. CA, USA) fitted with a polymethyl methacrylate (PMMA) disk and set to cut 300 µm. After the first round of chopping, the McIlwain sample platform was rotated by 90 degrees and the platform reset to cut in the second dimension. PMMA disks were rinsed of the tissue fragments using ice cold L15 buffer and collected into a tube. Tissue fragments were next separated equally into 3 tubes to test the effect of the following conditions: i) fresh, ii) 24-hour cold transport, and iii) cryopreservation.

Fresh

Fragments were dispensed into a V-bottom 96-well plate (Thermo Fisher Scientific) using the COPAS sorter (Union Biometrica). A gate was applied to select fragments that were of a desirable size. The selection of this gate was done empirically as described elsewhere (Example 8). Ten tissue fragments were dispensed into each well of a well-plate, with 50 µl of PBS used as sheath fluid for the COPAS sorting. Fragments were centrifuged at 300×g for 5 minutes at ambient temperature. About 25 µl of PBS was removed from each well. Fragments were encapsulated using complete Iscove's Modified Dulbeco's Medium (IMDM phenol free 21056-023; Fisher Scientific), 10% fetal bovine serum (FBS, 16000-044; Thermo Fisher), 1% penicillin/streptomycin, (15140-122; Gibco), SP-111 hydrogel (Stempharm Inc.), sodium bicarbonate (55761-500G; Sigma Aldrich), and collagen (08-115; Sigma Aldrich). Three minutes of UV light was applied to the plate to solidify the hydrogel. Complete IMDM (37° C.) was added to each well. Fragments were cultured for 72 hours (37° C.; 5% $CO_2$).

Cold Transport (or Cold Preservation)

Fragments were pelleted by centrifugation and then resuspended in 5 ml HypoThermosol (101104; BioLife Solutions, WA, USA) in a 50 ml conical tube. The tube was then placed on ice and into a 5° C. refrigerator overnight. After 24 hours, fragments were dispensed into a V-bottom 96-well plate using the COPAS sorter. A gate was applied to select fragments that were of a desirable size. The selection of this gate was done empirically as described in Example 8. As described earlier, 10 fragments were dispensed into each of 10 wells, along with 50 µl of PBS used as sheath fluid for sorting. Fragments were centrifuged at 300×g for 5 minutes at ambient temperature. As mentioned before, 25 µl of PBS was removed from each well. Tissue fragments were encapsulated using complete Iscove's Modified Dulbeco's Medium (IMDM phenol free 21056-023; Fisher Scientific), 10% fetal bovine serum (FBS, 16000-044; Thermo Fisher), 1% penicillin/streptomycin, (15140-122; Gibco), 0.5×SP-111 hydrogel (Stempharm Inc.), sodium bicarbonate (55761-500G; Sigma Aldrich), and collagen (08-115; Sigma Aldrich). Three minutes of UV light was applied to the plate to solidify the hydrogel. Complete IMDM (37° C.) was added to each well. Fragments were cultured for 72 hours (37° C.; 5% $CO_2$).

Cryopreservation

Tissue fragments were pelleted by centrifugation and then resuspended in 1 ml of CS10 (210373 BioLife Solutions). Fragments were placed in a Cool Cell (Corning, USA) which was placed into a −80° C. freezer overnight. Fragments were moved to liquid nitrogen (LN2) and stored there for 2 days. Fragments were then thawed in a 37° C. water bath until only a small ice crystal remained Prewarmed complete IMDM was added dropwise. The fragments were then spun down and resuspended in complete IMDM. Fragments were dispensed into a V-bottom 96-well plate using the COPAS sorter.

A gate was applied to select fragments that were of a desirable size. The selection of this gate was done empirically as described elsewhere (Example 8). As described in the previous sections, 10 fragments were dispensed into each of 10 wells, with 100 µl of PBS used as sheath fluid. Fragments were centrifuged at 300×g for 5 minutes at ambient temperature. following which, 25 µl of PBS was removed from each well. Fragments were encapsulated in hydrogel as described in the previous sections and cultured for 72 hours.

3D CellTiter-Glo® Assay

After 72 hours in culture, tissue fragments in each group were assayed using 3D CellTiter-Glo® Luminescent Cell Viability Assay (3D CTG; G9683; Promega). Collagenase D (25 mg/ml) was added to each well containing tissue fragments. Plates were then placed on a shaker in an incubator for 4 hours (37° C.; 5% $CO_2$) to digest the encapsulant and fragments. Removal of the collagenase was performed by pelleting and washing with PBS. 3D CTG reagent was added to a final concentration of 1×. Plates were shaken at ambient temperature for 30 minutes to lyse cells and release ATP (37° C.; 5% $CO_2$). Luminescence was read using a plate reader (Perkin Elmer). Graphs and statistical analyses were done in GraphPad Prism. The results of this study are shown in FIG. 4A.

Flow Cytometry Assay

Viability after different simulated transportations were also assessed by flow cytometry. After culture for 72 hours, fragments were dissociated by collagenase into single cells. Cells were stained with Hoechst 33342 (Invitrogen) for all nuclei, and by propidium iodide (PI; Invitrogen) for the nuclei of dead cells. These cells were then run through a flow cytometer (Northern Lights, Cytek) to count cells, look for total nuclei, and for PI-positive nuclei. Gates were drawn to separate nucleated cells into 3 categories: Cells which had very low PI signal were classified as "alive", those which had a moderate level of PI signal were classified as "leaky" and those with the highest level of PI signal were classified as "dead". The results of this study are shown in FIG. 4B.

Example 3: Comparison of Cell Viability in Human Tissue Fragments Under Hypothermal (Cold) Preservation Condition and Cryopreservation Condition, with Cell Viability in Fresh Tissue Fragments (not Subjected to any Storage/Preservation)

To assess the feasibility of transporting tumors from the site of excision (source site) to a second site (destination site) for processing, different methods of tumor preservation were evaluated in primary human tumor tissue. Primary patient samples were obtained from the University of Wisconsin-Madison BioBank on the date of surgical excision (IRB approved). The tumor types from five individual patients were pancreato-biliary, urinary bladder, colorectal, renal, and bladder respectively. This tissue was then fragmented to 300 μm×300 μm with the thickness varying between 100 μm and 300 μm (but consistent for each patient sample) using a combination of Compresstome and McIlwain tissue chopper. Fragments were subjected to one of the three following conditions: i) placed into culture immediately (fresh); ii) placed in HypoThermosol for 24 hours (cold transport); iii) cryopreserved in CS10 (cryopreserved) and subsequently thawed prior to culture. The details of preservation conditions are provided in Example 2. To prepare for culture, fragments were sorted (Copas; Union Biometrica) to exclude incompletely cut fragments and debris, and the tissue fragments were dispensed into 96-well V-bottom plates (Thermo Fisher). Ten fragments were dispensed per well, into 10 wells per condition. For culture, fragments were encapsulated in a PEG-based hydrogel (SP-111) in complete IMDM, collagen, and sodium bicarbonate and overlaid with complete IMDM. The tissue fragments were cultured at 37° C. in 5% $CO_2$. After culture (24-72 hours; consistent for a patient sample), dissociation of hydrogel and fragments was performed using collagenase X and then 3D Cell Titer Glo (G9683 Promega) was used to assess ATP concentration using a luminescence readout. As shown in FIG. 4C, both methods of simulated transportation retained the viability of the fresh tissue. This suggests that either 24 hours of cold transport or cryopreservation are feasible methods for preservation of primary patient tissue for transportation to a processing site.

Figure 5A:
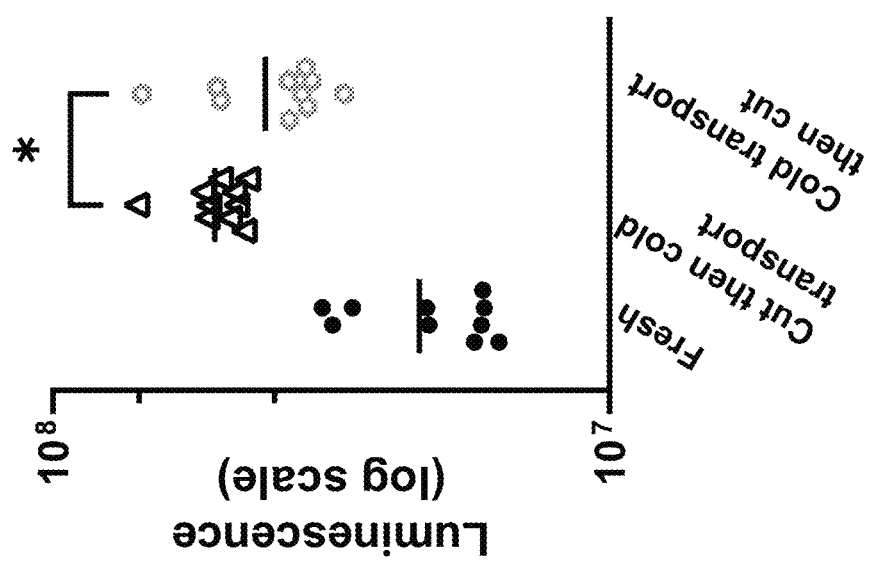
FIG. 5A shows comparison of cell viability under condition where tissue was cut into tissue fragments prior to cold transport (cut then cold transport) versus condition where tissue was subjected to cold transport conditions prior to cutting (cold transport then cut). The two conditions were further compared to fresh tissue fragments (fresh).

Example 4: Cutting Prior to Cold Transport Results in an Increase in Viability Compared to Cold Transport Prior to Cutting To assess whether cutting a tumor prior to cold transport altered the viability of the sample, a tumor was bisected, and simulation of cold transport was performed on an intact half of tumor and a pre-fragmented other half of the tumor. An EMT6 mouse breast cancer tumor was harvested from a mouse and bisected ex vivo. One half was immediately placed in ice cold HypoThermosol (101104; BioLife Solutions, WA, USA) and incubated for 24 hours on ice. The other half was fragmented immediately to 100 μm×300 μm×300 μm fragments using a Compresstome (Precisionary Instruments, USA) and McIlwain tissue chopper (TedPella, USA). These fragments were collected and separated into two groups. One group was placed into ice cold HypoThermosol and incubated for 24 hours on ice. The second group was immediately sorted (COPAS; Union Biometrica) to remove uncut fragments and debris and dispensed into a 96-well V-bottom plate. Ten wells of 10 fragments each were plated. Fragments were then encapsulated in a PEG-based hydrogel (complete IMDM, collagen, sodium bicarbonate, SP-111) and overlaid with complete IMDM. Fragments were cultured at 37° C. and 5% $CO_2$ for 96 hours. After culture, dissociation of hydrogel and fragments was performed using collagenase (I, II, III, IV; 10 mg/ml each). 3D Cell Titer Glo (G9683 Promega) was used to assess ATP concentration using a luminescence readout. Cutting before incubation on ice for 24 hours (resulted "cut then cold transport") in a significantly increased viability over transporting an intact tumor prior to cutting ("cold transport then cut") (FIG. 5A).

Group 1 (Fresh): These tissue fragments of dimension 100 μm×300 μm×300 μm (freshly cut from one half of the tumor) were sorted, encapsulated, and put into culture immediately for 96 hours.

Group 2 (Cut then cold transport): These tissue fragments of dimension 100 μm×300 μm×300 μm (freshly cut from one half of the tumor) were placed into HypoThermosol for 24 hours on ice. Following this incubation, they were sorted, encapsulated, and put into culture for 96 hours.

Group 3 (Cold transport then cut): This tumor half was placed immediately into HypoThermosol following bisection (without cutting the tumor half into fragments) and placed onto ice for 24 hours. Following this incubation, the tumor half was cut, sorted, encapsulated, and put into culture for 96 hours.

Example 5: Cutting Prior to Cryopreservation Results in Greater Viability Compared to Cutting after Cryopreservation To assess whether cutting a tumor prior to cryopreservation altered the viability of the sample, a tumor was bisected following which, both an intact half and a pre-fragmented half were cryopreserved. An EMT6 mouse breast cancer tumor was harvested from a mouse and bisected ex vivo. One half was immediately cryopreserved in CS10. The other half was fragmented immediately to 100 μm×300 μm×300 μm fragments using a Compresstome (Precisionary Instruments, USA) and McIlwain tissue chopper (TedPella, USA). These fragments were collected and separated into two groups. One group was cryopreserved using CS10. The second group was immediately sorted (COPAS; Union Biometrica) to remove uncut fragments and debris and dispensed into a 96-well V-bottom plate. Ten wells of 10 fragments each were plated. Fragments were then encapsulated in a PEG-based hydrogel (complete IMDM, collagen, sodium bicarbonate, SP-111) and overlaid with complete IMDM. Fragments were cultured at 37° C. and 5% $CO_2$ for 48 hours. After culture, dissociation of hydrogel and fragments was performed using collagenase (I, II, III, IV; 10 mg/ml each). 3D Cell Titer Glo was used to assess ATP concentration using a luminescence readout (G9683 Promega). Cutting before cryopreservation resulted in a significantly increased viability over cryopreservation of an intact tumor before cutting (FIG. 5B).

Group 1 (Fresh): These tissue fragments of dimension 100 μm×300 μm×300 μm (freshly cut from one half of the tumor) were sorted, encapsulated, and put into culture immediately for 48 hours.

Group 2 (Cut then cryo): These tissue fragments of dimension 100 μm×300 μm×300 μm (freshly cut from one half of the tumor) were cryopreserved in CS10. Following this incubation, they were thawed, sorted, encapsulated, and put into culture for 48 hours.

Group 3 (Cryo then cut): This tumor half was immediately cryopreserved in CS10 without cutting. This half was then thawed, cut, sorted, encapsulated, and put into culture for 48 hours.

Example 6: Oxygenation of Cutting Buffer During Tumor Cutting Increases Viability of Tumor Fragments To determine whether providing oxygen to tumors during the cutting process increased their viability, an EMT6 mouse breast cancer tumor was bisected. One half of the tumor was fragmented in the presence of excess oxygen and the other half was fragmented in the absence thereof. An EMT6 breast cancer tumor was excised and bisected ex vivo. One half was cut using a Compresstome while bubbling oxygen through the cutting medium, while the other half was cut using a Compresstome without additional oxygen. Both halves were cut on ice in L-15 buffer (L-15 medium, glutathione, HEPES) in a sterile environment. To prepare for culture, fragments were sorted (COPAS; Union Biometrica) to exclude incompletely cut fragments and debris and dispensed into 96-well V-bottom plates (Thermo Fisher). Ten fragments were dispensed per well into 10 wells per condition. For culture, fragments were encapsulated in a PEG-based hydrogel (SP-111 (StemPharm, WI, USA) in complete IMDM, collagen, sodium bicarbonate) and overlaid with complete IMDM. Culture was performed at 37° C. in normoxia with 5% $CO_2$. After 48 hours in culture, dissociation of hydrogel and fragments was performed using collagenase (I, II, III, IV; 10 mg/ml each). Then 3D Cell Titer Glo (G9683 Promega) was used to assess ATP using a luminescence readout. As shown in FIG. 6A, the tumor half that was fragmented in the presence of bubbled oxygen showed higher ATP after 48 hours of culture. This suggests that incorporating the oxygenation of cutting buffer improves viability of tumor fragments.

Example 7: Adding Glutathione and HEPES to Cutting Buffer Improves Fragment Viability Carbon dioxide independent L15 media with bubbled oxygen is used for cutting. To determine whether adding reduced glutathione as an antioxidant and HEPES to buffer pH would increase the viability of tumor fragments, an EMT6 tumor was cut with and without the addition of these two supplements. An EMT6 mouse breast cancer tumor was harvested from a mouse and bisected ex vivo. The tumor halves were each cut into 100 μm×300 μm×300 μm fragments using a Compresstome and McIlwain tissue chopper. Each tumor half was cut immediately on a Compresstome on ice, with oxygenation in a sterile environment. One half was cut in L15 buffer, while the other half was cut in L15 buffer containing glutathione (163 nM) and HEPES (25 mM). Cut fragments were sorted and dispensed as described above using a COPAS sorter. Ten fragments were deposited into each of ten wells per tumor half. Fragments were then encapsulated in a PEG-based hydrogel (SP-111 (StemPharm, WI, USA) in complete IMDM, collagen, sodium bicarbonate) and overlaid with complete IMDM. Fragments were cultured at 37° C. in 5% $CO_2$ for 48 hours. After culture, dissociation of hydrogel and fragments was performed using collagenases I, II, III, and IV (10 mg/ml each). 3D Cell Titer Glo was used to assess ATP concentration via a luminescence readout (G9683 Promega). Addition of supplements led to a moderate increase in the viability of tumor fragments after 48 hours in culture (FIG. 6B).

Example 8: Sorting Optimization Procedure

Arbitrary Gate R1
To dispense tissue fragments of interest into a well plate, a COPAS FP-1000 (Union Biometrica, USA) was used. Initially, an arbitrary gate R1 (see FIGS. 7A and B) based on time-of-flight (TOF) and extinction was set for capturing majority of the fragments. Using that gate, fragments were sorted and dispensed into 96-well plates. Bright-field images were taken for the dispensed fragments. For each fragment, the surface area and dimensions were measured using Fiji, an open-source software program for image analysis (Nat Methods. 2012 Jun. 28; 9(7):676-82). The tissue fragments that met the quality criteria (such as undamaged tissue fragments with sharp edges and desired size of approximately 300 μm in at least two of the three dimensions), were useable for downstream studies. These are shown in FIG. 7C. The tissue fragments not meeting the quality criteria or the undesired tissue fragments are shown in FIG. 7D. By mapping the measured fragments back to their original position in the dot plot of TOF versus extinction (FIG. 8A), an optimal gate R2 was empirically determined (as shown in FIG. 8B).

Gate R2
The refined gating R2 was performed using undesired reference fragments 2, 6, 7, and 10 as shown in FIG. 8C. This gate maximized the ideal fragment yield and excluded the majority of the fragments with undesired dimensions (FIG. 9A-C). The FIG. 9A shows the tissue fragments falling inside the gate and those falling outside the gate R2. With the optimized gate setting R2, 43% of the sorted fragments were cubes with sharp edges and the desired 300 μm size in two of the three dimensions, such as seen in FIG. 9C. Criteria for exclusion of fragments included fragments too small for analysis, severely damaged fragments, folded fragments, and multiple fragments that were piled on top of each other.

Gate R3
Further gating optimization was done to select an optimized gate setting R3, as shown in FIG. 10. The images of the fragments sorted with gate R2 are shown in FIGS. 10A and B. FIG. 10A shows the tissue fragments meeting the quality criteria. FIG. 10B shows the undesired tissue fragments. Using these tissue fragments as reference (as shown in FIG. 10C), a further refined gating R3 was selected (as shown in FIG. 10D). FIG. 10E shows that comparison between gate R2 and R3. Using gate setting R3, 63% of fragments were cubes with sharp edges and the desired 300 μm dimension (see FIG. 11A-C).

Gate R3 Compartmentalization
Further gating optimization was performed by subdividing gate R3 into smaller gates (see FIG. 12A). Fragments were dispensed for each gate which was refined based on the cutting quality and measurement of dispensed tissue fragments. The fragments meeting quality criteria or the useable tissue fragments are shown in FIG. 12B. The undesired fragments are shown in FIG. 12C. Based on the location of usable fragments (1, 2, 4, 6, 7, 8, 11, 12) as shown in FIG. 12D, the gates were refined by either shrinking and/or combining two gates together. For instance, R4 and R8 were refined and combined as refined R4A (FIG. 12E).

The refined comparted gates as shown in FIG. 12E were further optimized following the same procedures (see FIG. 13A-B). Useable fragments (B10, H9, B6, D12) and undesired fragments (B8, F10, H3) are shown in FIG. 13B-C. Based on the region where the majority of useable tissue fragments were located (FIG. 13D), the comparted gates were refined and combined into gate R11 (FIG. 13E). The useable tissue fragments had sharp and/or rough edges, two or more dimensions with desired size, were not mangled and were useable for downstream experiments.

Gate R11 Further gating optimization was performed to select an optimized gate setting R11, as shown in FIG. 14. Using gate setting R11, 68% of the fragments fell within gate R11 (FIG. 14A). Approximately 80% of the 96 fragments dispensed from gate R11 (FIG. 14B) were useable for downstream experiments (see FIG. 14C). FIG. 14D shows the undesired fragments. The gate was validated by sorting additional populations of fragments and verifying that the gate was providing a high yield of ideal fragments with desired fragment geometry.

Example 9: Tumor Slice Fragmentation and Sorting Procedure Preserves the Content of Tumor Infiltrating T-Lymphocytes (TIL)

Subcutaneous CT26 tumor was harvested from a mouse and cut into 100 μm thick slices. The slices were randomized into two equal groups of which one was set aside termed "Control" and the other was fragmented (300×300 μm) and sorted using tissue fragment based on pre-defined forward and side light scatter gate parameters (as described above in Example 8). Both preparations were then enzymatically digested, for 1.25 h, using Collagenase Type IV, 0.25 mg/mL, 40 U/mL/Hyaluronidase, 0.025 mg/mL/DNase I, 0.01 mg/mL. The cell suspensions were stained using Hoechst, propidium iodide and fluorescence-labeled antibodies specific for immune cell markers including CD3, CD4, CD8, CD45, CD25, CD69, OX-40 and ICOS. After washing, the cells were analyzed using a 3-laser Cytek Northern Lights flow cytometer followed by gating on live cells and CD45-positive and CD3-positive cells (T cells). Shown are representative dot-plots with respect to the CD4 and CD8 fluorescence intensities. Respective cell content is calculated in reference to the total live cell content. Notable is that the CD4+ and CD8+ content values in the control tumor preparation (sliced-only) are substantially similar to the respective content values in the fragmented and sorted tumor tissue preparation, signifying that the tumor fragmentation and sorting method favorably preserves TIL content (FIG. 15).

Example 10: MP-FLIM can Distinguish Tumor from Normal Tissue in Live Tissue Fragments without Extrinsic Labels Live EMT6 tumors and mammary fat pad were cut into tissue fragments that were then sorted and cultured in glass-bottomed multi-well plates. The structure and metabolic status of the live tissue fragments (LTFs) was imaged based on the intrinsically fluorescent metabolic co-factors nicotinamide dinucleotides and phosphorylated nicotinamide dinucleotides (NAD(P)H) fluorescence intensity and lifetime using multiphoton fluorescence lifetime imaging microscopy (MP-FLIM) by time-correlated single photon counting. The data was analyzed by fitting fluorescence decay curves in individual pixels with dual or triple exponents to generate images of lifetime parameters, including the mean and individual component lifetimes and amplitudes. FIG. 17A shows the intrinsic contrast from multiphoton imaging revealing cellular and tissue structures. Shown in the figure is the amplitude of NAD(P)H short lifetime component (a1). FIG. 17B shows analysis of the image in FIG. 17A indicating the mean lifetime (tm) and short lifetime component (a1) of NAD(P)H in tumor and normal tissue, showing the differences in tm (mean) and a1 (mean) between tumor tissue and normal tissue. Notable is the distinction between tumor versus normal in the mean NAD(P)H fluorescence lifetime (tm) and in the percentage of the short lifetime component (a1), which are two key NAD(P)H fluorescence lifetime metrics. In particular, the tumor is characterized by tm (<1000 ps) that is of smaller value than that of the normal (>1000 ps). Looking at the short lifetime amplitude, a1, the tumor is characterized by mean a1 values (73.7%) that are greater than those of the normal (59.6%).

For entropy analysis of NAD(P)H fluorescence intensity, a spatially moving entropy calculation was performed across the image. A entropy value was calculated from the fluorescence intensity counts within a moving circular region (kernel), and the distribution of all overlapping (per central pixel) were generated and analyzed. The size of the moving circular region was tested for increasing sizes (diameter 14 μm, 28 μm, and 42 μm) with 14 μm diameter found to highlight more information content in the resultant distribution. A range of 14 μm to 42 μm was chosen in relation to approximate cell to cell length scale up to fat cell size respectively. The distribution metrics (median, std dev, skew and kurtosis) of entropy values calculated from all pixels (circular regions centered at each pixel) in the image. FIG. 17C shows the spatial heterogeneity of NAD(P)H fluorescence intensities, quantified utilizing entropy parameters (also called entropy metrics) including median entropy and entropy skew. The median entropy was higher, and entropy distribution negatively skewed, for EMT6 tumor tissue compared to the corresponding normal tissue of origin, mouse mammary fat pad ($p<0.01$) (FIG. 17C, Table 1). There was also a difference in kurtosis, with tumor being closer to a Gaussian distribution and normal tissue having a higher kurtosis (Table 1).

TABLE 1

Entropy metrics between tumor and normal (t-Test: Two-Sample Assuming Unequal Variances)

| | Tumor | Normal |
|---|---|---|
| A) Median entropy | | |
| Mean | 5.794442519 | 5.366590411 |
| Variance | 0.109197403 | 0.057091904 |
| Observations | 9 | 11 |
| Hypothesized Mean Difference | 0 | |
| df | 14 | |
| t Stat | 3.250718722 | |
| P(T <= t) one-tail | 0.002902199 | |
| t Critical one-tail | 1.761310136 | |
| P(T <= t) two-tail | 0.005804397 | |
| t Critical two-tail | 2.144786688 | |
| B) Entropy skewness | | |
| Mean | −0.02005 | 0.089766 |
| Variance | 0.000795 | 0.002959 |
| Observations | 9 | 11 |
| Hypothesized Mean Difference | 0 | |
| df | 16 | |
| t Stat | −5.80945 | |
| P(T <= t) one-tail | 1.33E−05 | |
| t Critical one-tail | 1.745884 | |
| P(T <= t) two-tail | 2.66E−05 | |
| t Critical two-tail | 2.119905 | |
| C) Kurtosis | | |
| Mean | 0.090647 | 0.257586 |
| Variance | 0.00344 | 0.014368 |
| Observations | 9 | 11 |
| Hypothesized Mean Difference | 0 | |
| df | 15 | |
| t Stat | −4.06265 | |
| P(T <= t) one-tail | 0.00051 | |
| t Critical one-tail | 1.75305 | |
| P(T <= t) two-tail | 0.001021 | |
| t Critical two-tail | 2.13145 | |

As shown in FIG. 17D, a second harmonic generation imaging of tumor versus normal tissue of origin was performed. As seen in the image and quantified in the graph (FIG. 17E) using CT-FIRE V2.0 and GraphPad Prism softwares, the collagen fibers in tumor have narrower width compared to collagen fibers in normal tissue ($p<0.0011$).

Example 11: Label-Free Imaging of NAD(P)H Fluorescence Intensity Enables Distinction of Live from Dead Cells in Cultured Tumor Fragments Live EMT6 tumors were cut into tissue fragments, which were then sorted and cultured in glass-bottomed multi-well plates. To induce cancer cell death, LTFs were treated with the alkylating agent, cisplatin, for 24 h. After treatment, LTF structure and metabolic status were imaged based on the fluorescent metabolic co-factors, reduced nicotinamide dinucleotides (NAD(P)H) fluorescence intensity and lifetime using MP-FLIM. As a ground truth viability reference, the same LTFs were stained using nuclear cell viability probe propidium iodide (PI). FIG. 18A, shows the NAD(P)H fluorescence intensity image. FIG. 18B shows the PI fluorescence intensity image on the same tissue image. In FIG. 18C, cell and cell nuclei shapes were segmented based on the combined signals. FIG. 18D shows PI fluorescence intensities of each cell central regions plotted as function of NAD(P)H intensities on a cell-by-cell basis. Notable is clear distinction of cells expressing high NAD(P)H intensities from cells with high PI intensities. In order to determine a NAD(P)H threshold, first, the threshold of PI nuclear intensity was set based on the nuclear segmentation, indicated by the horizontal line, thereby identifying the PI-high cells above the PI threshold. Then, the threshold of NAD(P)H intensity was determined such that >90% of the PI-high cells (identified by the PI threshold) are excluded by the NAD(P)H threshold. This is termed the PI-trained NAD(P)H intensity threshold. The percentages of cells that exhibited a particular combination of PI high or low signals and NAD(P)H high or low signals was calculated based on the number of cells in each quadrant, determined by the combination of the PI and NAD(P)H thresholds. Notable was that most PI-high cells exhibited low NAD(P)H signals and vice versa, most NAD(P)H-high cells exhibited low PI signals.

Example 12: Hyperoxia During Culture Leads to Decreased Fragment Viability

Oxygenation during cutting was shown to improve tumor fragment viability. To test whether increasing oxygen levels during culture also increases viability, EMT6 tumor fragments were cultured either at ambient oxygen, or in an incubator containing 80% oxygen. An EMT6 tumor was cut to produce fragments of 100 μm×300 μm×300 μm dimension using Compresstome and McIlwain tissue chopper. The Compresstome was used in a sterile environment on ice containing L15 media with glutathione and HEPES, and with oxygen bubbling. Cut fragments were sorted and dispensed as described above using a COPAS sorter. Ten fragments were deposited into each of ten wells into two polystyrene 96-well plates. Fragments were then encapsulated in a PEG-based hydrogel (SP-111 (StemPharm, WI, USA) in complete IMDM, collagen, sodium bicarbonate) and overlaid with complete IMDM. Both plates were cultured at 37° C. for 72 hours. One plate was placed in an incubator with 5% $CO_2$ and ambient $O_2$ (21%), while one plate was placed in an incubator with 5% $CO_2$ and 80% $O_2$. After culture, dissociation of hydrogel and fragments was performed using collagenases I, II, III, and IV (10 mg/ml each). 3D Cell Titer Glo was used to assess ATP concentration via a luminescence readout (G9683 Promega). Culturing tumor fragments in 80% oxygen led to a significant decrease in viability compared to culturing them at ambient oxygen (FIG. 19A).

Example 13: Hypoxia During Culture Increases Fragment Viability

Since many tumors are reported to have low levels of intratumoral oxygen, hypoxia during culture was tested. To test whether decreasing oxygen levels during culture increases viability, we cultured EMT6 tumor fragments at either ambient oxygen, or in an incubator containing 5% oxygen. An EMT6 tumor was fragmented at 100 μm×300 μm×300 μm using the Compresstome and McIlwain tissue chopper. The Compresstome was used in a sterile environment on ice containing L15 media, supplemented with glutathione and HEPES and further with oxygen bubbling. Cut fragments were sorted and dispensed as described above using a COPAS sorter. Ten fragments were deposited into each of ten wells into two polystyrene 96-well plates. Fragments were then encapsulated in a PEG-based hydrogel (SP-111 (StemPharm, WI, USA) in complete IMDM, collagen, sodium bicarbonate) and overlaid with complete IMDM. Both plates were cultured at 37° C. for 72 hours. One plate was placed in an incubator with 5% $CO_2$ and ambient $O_2$ (21%), while one plate was placed in an incubator with 5% $CO_2$ and 5% $O_2$. After culture, dissociation of hydrogel and fragments was performed using collagenase D (25 mg/ml). Cells from fragments were stained with Hoechst33342 and propidium iodide (PI) and assayed by flow cytometry (Cytek, USA). Culturing fragments in 5% $O_2$ lead to an increase in the number of live cells, and a decrease in the percentage of PI-positive cells (FIGS. 19B and 19C). Thus, hypoxia increases viability in EMT6 tumor fragments.

Example 14: Tumor Fragment Viability is Retained Over 7 Days in Culture

To understand tumor fragment viability over time, 3D Cell Titer Glo was performed from 3-7 days post processing on tumor fragments from the same tumor. An EMT6 tumor was fragmented at 100 μm×300 μm×300 μm using the Compresstome and McIlwain tissue chopper. The Compresstome was used in a sterile environment on ice containing L15 media, supplemented with glutathione and HEPES and further with oxygen bubbling. Cut fragments were sorted and dispensed as described above using a COPAS sorter. Ten fragments were deposited into each of ten wells into five polystyrene 96-well V-bottom plates. Fragments were then encapsulated in a PEG-based hydrogel (SP-111 (StemPharm, WI, USA) in complete IMDM, collagen, sodium bicarbonate) and overlaid with complete IMDM. All plates were cultured at 37° C. and 5% $CO_2$. Starting after 72 hours (3 days), 3D Cell Titer Glo was used to assess ATP concentration from one plate of fragments each day for the next 5 days (G9683 Promega). Fragments were dissociated using collagenase D (25 mg/ml) prior to 3D Cell Titer Glo assay. Viability was maintained over time in culture and was significantly higher after 7 days as compared to 3 days (FIG. 20). This indicates that tumor fragments may be growing during the 3 to 7 day culture period.

Example 15: Recovery of Tissue Fragments in Culture

Fresh EMT6 tumor was cut into 100×300×300 μm sized tissue fragments. Ten wells were filled with 10 fragments into each of two v-bottom plates. In the first plate, collagenase (I, II, III, IV; 10 mg/ml each) was added and the fragments were dissociated prior to running the 3D Cell Titer Glo assay to determine ATP concentration. The second plate of fragments were then encapsulated in a PEG-based hydrogel (SP-111 (StemPharm, WI, USA) in a complete combination of DMEM, MEM, and RPMI media) and overlaid with complete combination medium (DMEM, MEM, RPMI). This plate was cultured for 72 hours (37° C.; 5% $CO_2$). After culture, collagenase (I, II, III, IV; 10 mg/ml each) was added and the fragments were dissociated prior to running the 3D Cell Titer Glo assay to determine ATP concentration. ATP concentration was higher after 3 days of culture than directly after processing (FIG. 21A). This supports the idea that the fragments recover over time in culture.

A flow cytometry analysis of the fragments confirmed the higher number of live cells and lower percentage of dead cells after 3 days of culture than directly after processing (FIG. 21B-C). To determine the recovery of fragments over time by flow cytometry, CT26 fragments were cut into 100×300×300 μm fragments using the Compresstome and McIlwain chopper. For the day 0 sample set, 100 fragments were sorted into a 1.5 ml tube and digested with collagenase D (0.2 mg/ml). These cells were stained with Hoechst 33342 and propidium iodide (PI) and sent through a flow cytometer. For the day 3 sample set, ten wells of a 96-well U-bottom low adherence plate were filled with 10 fragments each. Complete IMDM media was added to these fragments, which were then cultured for 3 days (37° C.; 5% $CO_2$). After culture, the fragments were pooled into a single tube and digested with collagenase D (0.2 mg/ml). These cells were stained with Hoechst 33342 and propidium iodide (PI) and sent through a flow cytometer. For both groups, PI-low cells were considered alive, while PI-high cells were considered dead. After 3 days in culture, the total number of live cells increased (FIG. 21B) and the percentage of dead cells decreased (FIG. 21C). This suggests that fragments recover and grow during time in culture.

Figure 22A:
FIG. 22A-B show the kinetics of diffusion of small molecules (doxorubicin) and large molecules (anti-CD45 antibody) into the tissue fragments.
Figure 22B:
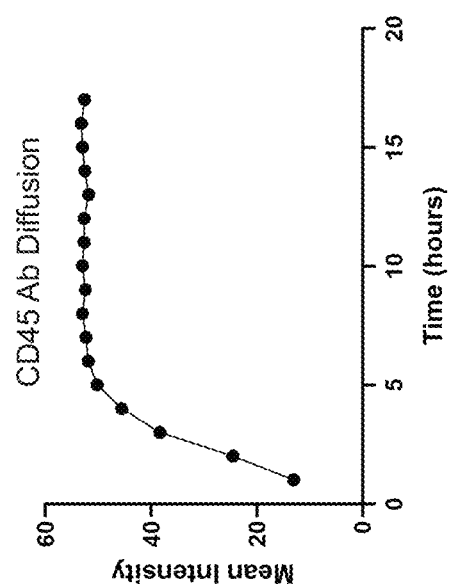

Example 16: Diffusion of a Small Molecule Chemotherapy Drug and an Antibody into a Live Tumor Fragment As shown in FIG. 22A, a live tumor fragment was cultured at 37° C. and imaged before the addition of doxorubicin followed by imaging at 15 min, and 2 h after that. Notable was gradual appearance of doxorubicin-characteristic fluorescence first in the periphery of tissue fragment at 15 minutes followed by full-thickness staining of the entire fragment area at 2 hours. As shown in FIG. 22B, the kinetics of diffusion of fluorescently labelled anti-CD45 antibody was quantified as a function of the elapsed time, starting from the time of addition to the culture media. Notable is plateau staining within about 5 h. As noted by this experiment, both small molecule drugs and large antibodies diffused into the live tissue fragments.

Example 17: Label-Free Microscopy Detects Cytotoxic Agent-Induced Death of Cultured Tumor Fragments Live EMT6 tumors were cut into tissue fragments that were then sorted and cultured in glass-bottomed multi-well plates. To induce cancer cell death, one group was treated with the multi-kinase inhibitor, staurosporine (STS), and the control group was treated with the vehicle (Veh). Before (0 h) and after treatment (24 h), the structure and metabolic status of tumor fragments were imaged based on the intrinsically fluorescent metabolic co-factor nicotinamide dinucleotides (NAD(P)H) fluorescence intensity and lifetime using MP-FLIM by time-correlated single photon counting. The data was analyzed by fitting fluorescence decay curves with dual exponents. As shown in FIG. 23A, the mean lifetimes (tm), and as shown in FIG. 23B, the short lifetime amplitudes (a1), were measured for the tissue fragment regions of interest. Each dot represents one fragment. Notable is a statistically significant increase in the whole fragment mean lifetime (tm, p<0.002) and concomitant decrease in the short lifetime component ($\alpha 1$, p<0.002) at 24 hours of staurosporine exposure. FIG. 23C shows the time course of the short lifetime component, al, and FIG. 23D shows the time course of the mean lifetime in the tissue fragments upon addition of Vehicle or Staurosporine, or in untreated tissue fragments (none).

Figure 24:
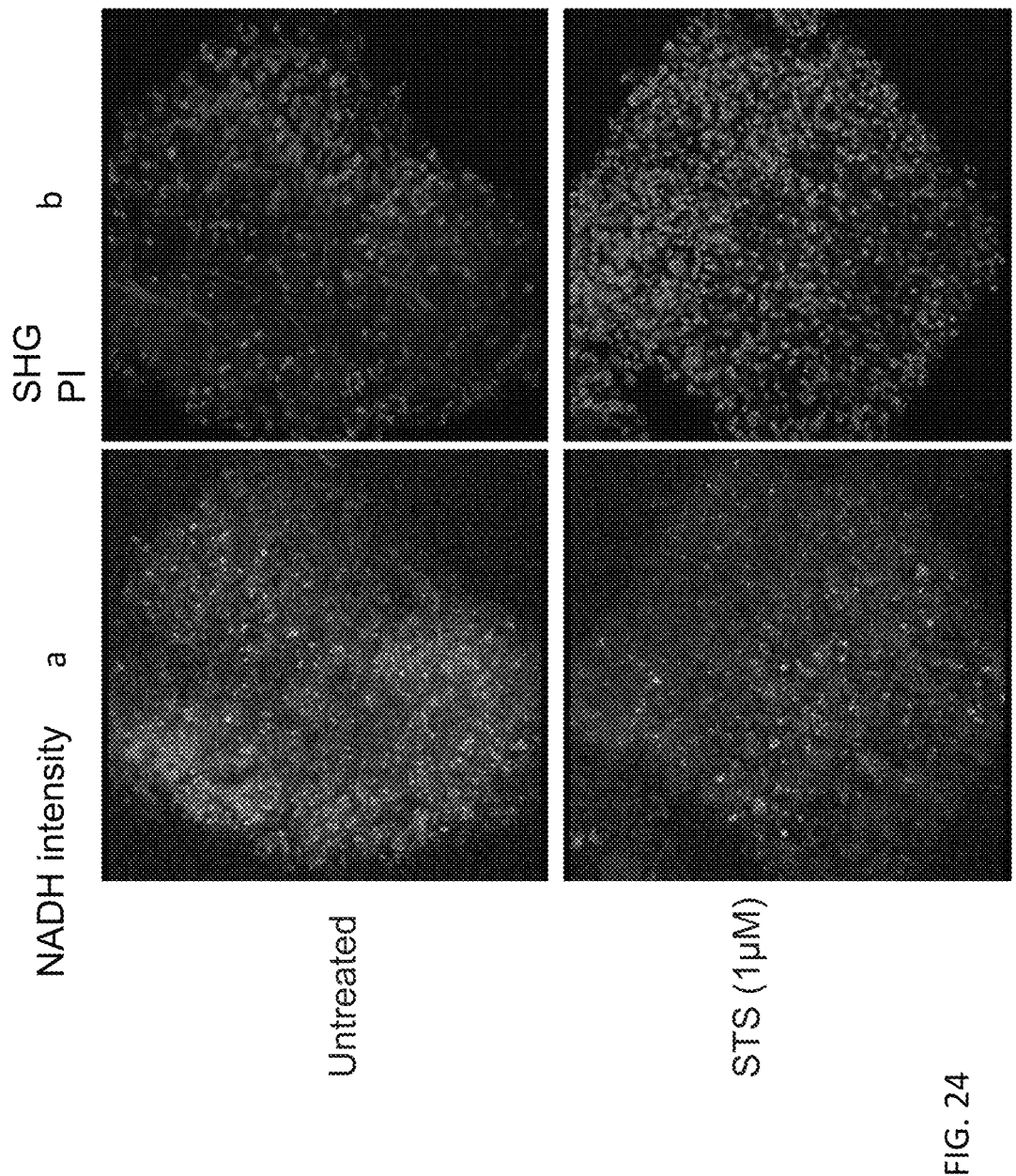
FIG. 24 shows the comparison of label-free NAD(P)H microscopy with the cellular viability ground truth (PI fluorescence) in cultured tumor fragments, which are untreated or staurosporine (STS) treated. Panel (a) shows NAD(P)H fluorescence (indicative of live cells) which is higher in untreated compared to STS treated fragment. Panel (b) shows PI fluorescence (indicative of dead cells) which is higher in STS treated fragment compared to untreated fragment.

Example 18: Comparison of Label-Free NAD(P)H Microscopy with the Cellular Viability Ground Truth in Cultured Tumor Fragments Live EMT6 tumors were cut into tissue fragments that were then sorted and cultured in glass-bottomed multi-well plates. To induce cancer cell death, one group was treated with the multi-kinase inhibitor, staurosporine (STS), and the control group was untreated. After 24 h, the structure and metabolic status of tumor fragments were imaged based on the intrinsically fluorescent metabolic co-factor nicotinamide dinucleotides (NAD(P)H) fluorescence intensity using multiphoton microscopy with 720 nm excitation. FIG. 24, panel (a) shows the NAD(P)H intensity in untreated and STS treated fragments respectively. As shown in FIG. 24, panel (b), the same fragments were re-imaged after staining with the nuclear dye propidium iodide (PI) that stains the nuclei of dead cells (red). For structural reference, the second harmonic generation was also imaged (blue). Staurosporine treatment resulted in increased numbers of PI-stained nuclei consistent with cell death (panel b, STS treated versus untreated). This effect was accompanied by a loss of NAD(P)H intensity (panel a, STS treated versus untreated).

Example 19: Detection of Secreted Immune Regulatory Factors by Live Tumor Fragments in Response to Treatment with Immunotherapy Drug Anti-PD1 or Anti-PD1 Combination with Anti-CTLA4

Figure 25A:
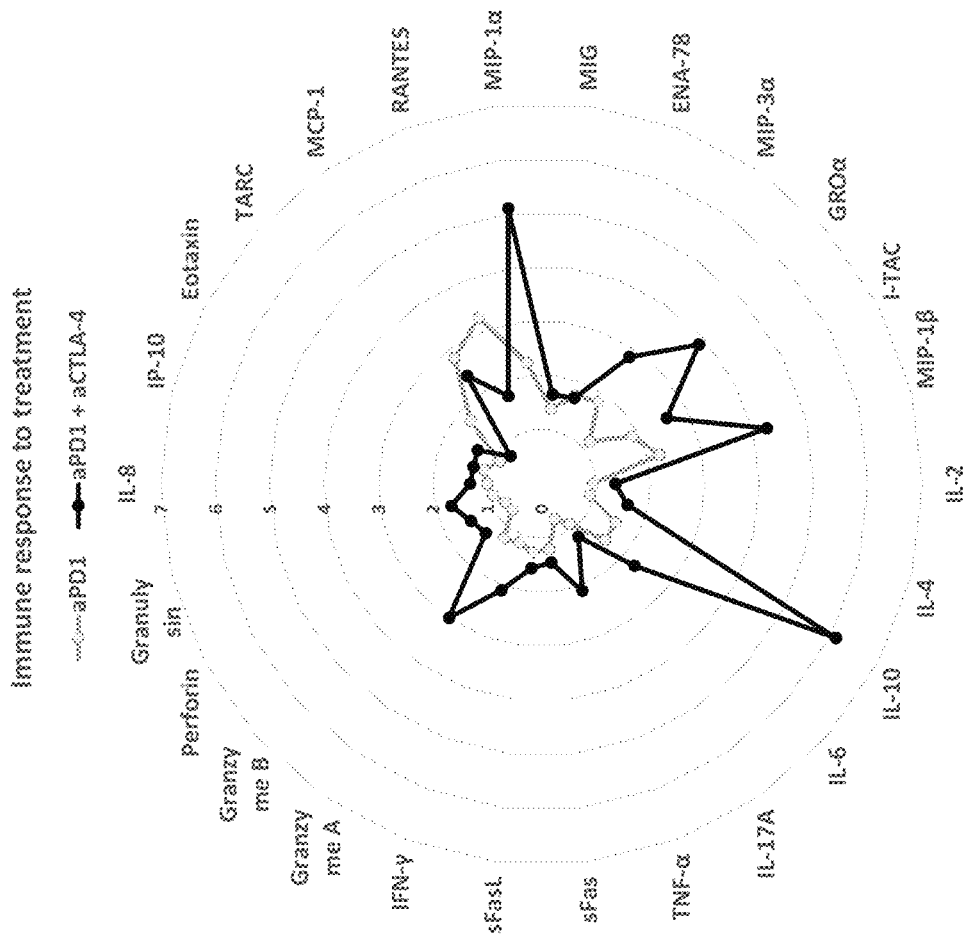
FIG. 25A shows immune response in human tissue fragments in response to treatment with immunotherapy drug anti-PD1 and combination of anti-PD1 and anti-CTLA4 expressed as a fold increase of supernatant secreted factor concentrations in relation to the untreated tissue fragments.
Figure 25B:
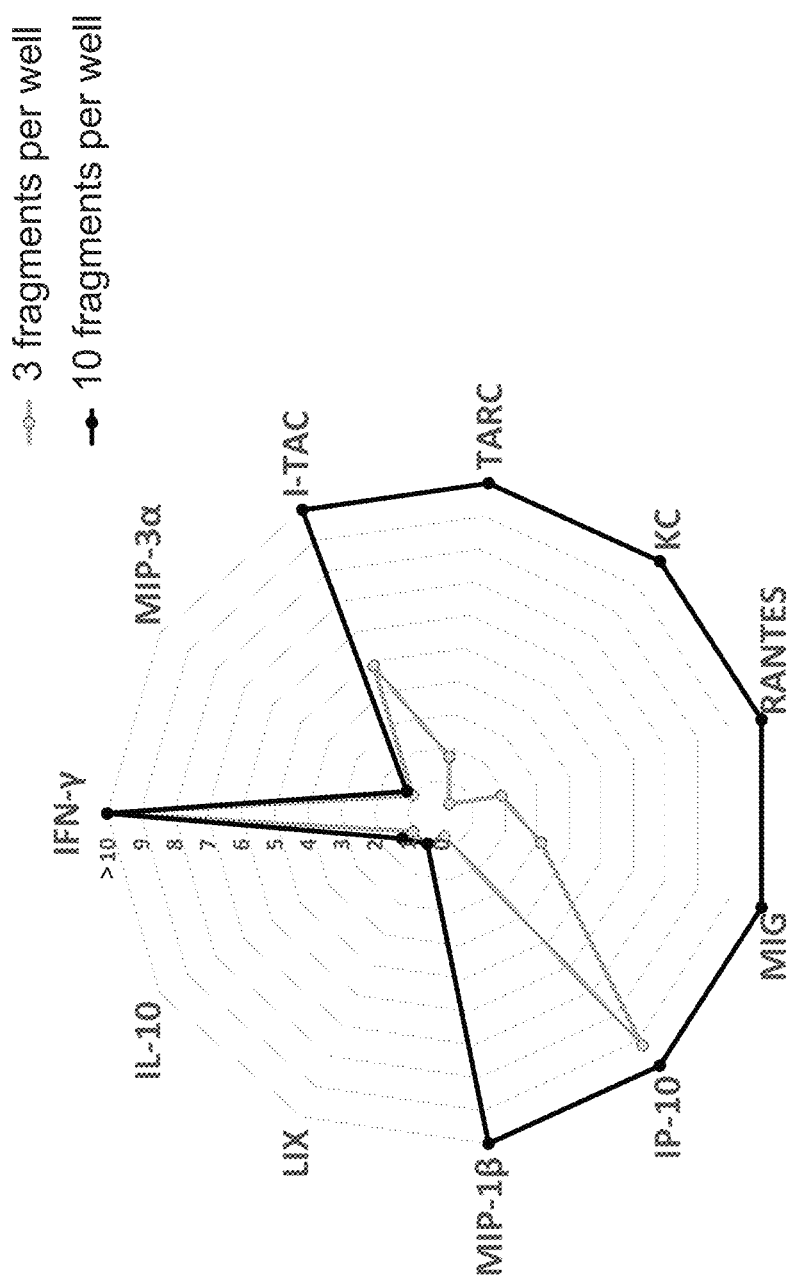
FIG. 25B shows immune response in mouse tissue fragments in response to treatment with a combination of immunotherapy drugs anti-PD1 and anti-CTLA4 treatment expressed as a fold increase of supernatant secreted factor concentrations in relation to the untreated tissue fragments.

Human tumor excisions were obtained from the University of Wisconsin (Institutional Review Board (IRB) approved) and CT26 tumors were grown in mice. Tumor excisions were cut into 300×300 μm live tumor fragments of 100-300 μm thickness, sorted into multi-well plates, and cultured for 48 or 72 h in the presence or absence of anti-PD1 (nivolumab or mouse equivalent), anti-PD1 plus anti-CTLA4 (ipilimumab or mouse equivalent), or concanavalin A (ConA) as a positive control. Cell viability was ascertained by ATP luminescence assay or flow cytometry (not shown). Supernatant cytokines were measured using LEGENDPlex bead immunoassay. In human samples, found was the greater presence of IFN-γ and 16 cytokines associated with immune activation in both the ConA (not shown) and anti-PD1 treated samples relative to the untreated control (FIG. 25A). In human LTFs, cytokine panel upregulation was observed for anti-PD1, expressed in terms of fold increase relative to an untreated. control (p=1.1e-5). Furthermore, treatment with anti-PD1 plus anti-CTLA4 resulted in overall greater degree of cytokine upregulation (in terms of fold increase over the untreated control) than the treatment with anti-PD1 alone (p=3.7e-9). In FIG. 25B, likewise, in mouse specimens, found was a greater presence of IFN-γ and 10 cytokines associated with immune activation in anti-PD1 treated samples in terms of a fold increase in relation to the untreated control. The presence of cytokines was greater in wells with 10 fragments than in wells with 3 fragments, indicating suitability of culture conditions.

We claim:

1. A method of predicting the clinical responsiveness of a subject to a potential anticancer drug or agent, the method comprising:
   i. sorting tissue fragments containing or suspected of containing tumor cells into desirable fragments and undesirable fragments based on an optical characteristic, and dispensing a controlled number of desirable tissue fragments into chambers of a culture platform, wherein the tissue fragments are generated from a tissue obtained from a subject having or suspected of having cancer;
   ii. adding a potential anticancer drug or agent to the desirable tissue fragments dispensed into the chambers of the culture platform and culturing the desirable tissue fragments in presence of the potential anticancer drug or agent;
   iii. performing one or more ex-vivo measurements on the desirable tissue fragments; and
   iv. predicting the clinical responsiveness of the subject to the potential anticancer drug or agent based on data obtained from the one or more ex-vivo measurements.

2. The method of claim 1, wherein the tissue fragments are sorted by automatically utilizing pre-defined gate settings based on one of more parameters of the tissue fragments selected from size, integrity, absence of multiplets, or absence of exogenous agents.

3. The method of claim 2, wherein the size of each tissue fragment is between about 50 microns and about 500 microns in at least two dimensions.

4. The method of claim 1, wherein the step of culturing the desirable tissue fragments in presence of the potential anticancer drug or agent comprises culturing the desirable tissue fragments in presence of the potential anticancer drug or agent for a period of about 24 hours to about 7 days.

5. The method of claim 4, wherein the desirable tissue fragments are cultured under conditions of hypoxia.

6. The method of claim 4, wherein the step of performing one or more ex vivo measurements on the desirable tissue fragments comprises imaging live tissue fragments.

7. The method of claim 6, wherein the step of imaging the live tissue fragments comprises performing longitudinal measurements on the desirable tissue fragments treated with the potential anticancer drug or agent during the period of culture to determine the change in fluorescence lifetime of an endogenous fluorophore and/or the fluorescence emission intensity of one or more populations of the endogenous fluorophore distinguished by fluorescence lifetimes.

8. The method of claim 7, wherein the endogenous fluorophore is NAD(P)H.

9. The method of claim 1, wherein the potential anticancer drug or agent is an immunotherapy drug or agent.

10. The method of claim 9, wherein the step of performing one or more ex vivo measurements on the desirable tissue fragments comprises measuring one or more factors selected from a panel consisting of Il-2, Il-4, Il-6, Il-10, Il-17A, TNF-α, sFas, sFasL, IFN-g, granzyme A, granzyme B, perforin, granulysin, Il-8, IP-10, eotaxin, TARC, MCP-1, RANTES, MIP-1a, MIG, ENA-78, MIP-3α, GROα, I-TAC and MIP-1b.

11. The method of claim 1, wherein the step of predicting the clinical responsiveness of the subject to the potential anticancer drug or agent comprises inputting the data obtained from the one or more ex-vivo measurements into a predictive algorithm.

12. The method of claim 11, wherein the steps to generate the predictive algorithm comprises:
   a) obtaining a set of training tissue parameter data generated from one or more ex-vivo tissue parameter measurements performed on a set of tissue fragments treated ex-vivo with a drug or an agent, wherein the set of tissue fragments are generated from tissues obtained from a training cohort of subjects;
   b) obtaining a set of training clinical parameter data generated from one or more clinical parameter measurements performed on the training cohort of subjects treated with the drug or the agent; and
   c) generating a predictive algorithm of responsiveness to the drug or the agent, using the set of training tissue parameter data and the set of training clinical parameter data.

13. The method of claim 1, further comprising imaging the tissue fragments to estimate one or more of tumor content or cell viability of the tissue fragments prior to addition of the drug or the agent, wherein i) the drug or the agent is added to the desirable tissue fragments based on one or more of the estimated tumor content or the cell viability, and/or wherein ii) the data from the one or more ex-vivo measurements is analysed based on one or more of the estimated tumor content or cell viability.

14. The method of claim 1, wherein the tissue fragments are generated from the tissue by cutting the tissue in an oxygenated cutting medium.

15. The method of claim 14, wherein the tissue fragments are preserved under hypothermic preservation and/or cryopreservation condition after being cut from the tissue.

16. The method of claim 15, wherein the tissue fragments are cryopreserved and wherein the method further comprises thawing the cryopreserved tissue fragments prior to sorting.

* * * * *